US012236199B2

(12) United States Patent
Tunstall-Pedoe et al.

(10) Patent No.: US 12,236,199 B2
(45) Date of Patent: Feb. 25, 2025

(54) COMPUTER IMPLEMENTED METHOD FOR THE AUTOMATED ANALYSIS OR USE OF DATA

(71) Applicant: UNLIKELY ARTIFICIAL INTELLIGENCE LIMITED, Cambridgeshire (GB)

(72) Inventors: William Tunstall-Pedoe, Cambridgeshire (GB); Finlay Curran, Cambridgeshire (GB); Harry Roscoe, Cambridgeshire (GB); Robert Heywood, Cambridgeshire (GB)

(73) Assignee: UNLIKELY ARTIFICIAL INTELLIGENCE LIMITED, Cambridgeshire (GB)

( * ) Notice: Subject to any disclaimer, the term of this patent is extended or adjusted under 35 U.S.C. 154(b) by 0 days.

(21) Appl. No.: 18/410,038

(22) Filed: Jan. 11, 2024

(65) Prior Publication Data
US 2024/0184993 A1    Jun. 6, 2024

Related U.S. Application Data

(63) Continuation of application No. 18/469,128, filed on Sep. 18, 2023, which is a continuation of application (Continued)

(30) Foreign Application Priority Data

Aug. 24, 2020 (GB) ...................................... 2013207
Sep. 21, 2020 (GB) ...................................... 2014876
Dec. 18, 2020 (GB) ...................................... 2020164

(51) Int. Cl.
*G06F 17/00*       (2019.01)
*G06F 16/242*     (2019.01)
(Continued)

(52) U.S. Cl.
CPC ............ *G06F 40/35* (2020.01); *G06F 16/243* (2019.01); *G06F 16/322* (2019.01);
(Continued)

(58) Field of Classification Search
None
See application file for complete search history.

(56) References Cited

U.S. PATENT DOCUMENTS 4,974,191 A    11/1990   Amirghodsi et al.
5,386,556 A     1/1995   Hedin et al.
(Continued)

FOREIGN PATENT DOCUMENTS

AU    2003266850 B2    11/2007
CA       3095725 A1    10/2019
(Continued)

OTHER PUBLICATIONS

"CYC Knowledge Base," [online] en.wikipedia.org/wiki/cyc; published in 2019.
(Continued)

*Primary Examiner* — Satwant K Singh
(74) *Attorney, Agent, or Firm* — Saul Ewing LLP

(57) ABSTRACT

A computer implemented method for the automated analysis or use of data is implemented by a voice assistant. The method comprises the steps of: (a) storing in a memory a structured, machine-readable representation of data that conforms to a machine-readable language ('machine representation'); the machine representation including representations of user speech or text input to a human/machine interface; and (b) automatically processing the machine representations to analyse the user speech or text input.

30 Claims, 9 Drawing Sheets

Related U.S. Application Data

No. 18/088,574, filed on Dec. 25, 2022, now Pat. No. 11,763,096, which is a continuation of application No. 18/001,368, filed as application No. PCT/GB2021/052196 on Aug. 24, 2021.

(51) Int. Cl.

| | | |
|---|---|---|
| *G06F 16/31* | (2019.01) | |
| *G06F 16/3329* | (2025.01) | |
| *G06F 16/951* | (2019.01) | |
| *G06F 40/123* | (2020.01) | |
| *G06F 40/126* | (2020.01) | |
| *G06F 40/20* | (2020.01) | |
| *G06F 40/205* | (2020.01) | |
| *G06F 40/211* | (2020.01) | |
| *G06F 40/226* | (2020.01) | |
| *G06F 40/242* | (2020.01) | |
| *G06F 40/279* | (2020.01) | |
| *G06F 40/30* | (2020.01) | |
| *G06F 40/35* | (2020.01) | |
| *G06F 40/45* | (2020.01) | |
| *G06F 40/47* | (2020.01) | |
| *G06F 40/58* | (2020.01) | |
| *G06N 3/0442* | (2023.01) | |
| *G06N 3/0455* | (2023.01) | |
| *G06N 3/0499* | (2023.01) | |
| *G06N 3/08* | (2023.01) | |
| *G06N 5/02* | (2023.01) | |
| *G06Q 10/1053* | (2023.01) | |
| *G06Q 30/0251* | (2023.01) | |
| *G06Q 30/0601* | (2023.01) | |
| *G10L 15/16* | (2006.01) | |
| *G10L 15/18* | (2013.01) | |
| *G10L 15/22* | (2006.01) | |
| *G10L 15/26* | (2006.01) | |
| *G10L 25/63* | (2013.01) | |
| *G16H 10/60* | (2018.01) | |
| *H04L 51/02* | (2022.01) | |
| *G06N 3/091* | (2023.01) | |
| *G10L 15/08* | (2006.01) | |

(52) U.S. Cl.
CPC ........ *G06F 16/3329* (2019.01); *G06F 16/951* (2019.01); *G06F 40/123* (2020.01); *G06F 40/126* (2020.01); *G06F 40/20* (2020.01); *G06F 40/205* (2020.01); *G06F 40/211* (2020.01); *G06F 40/226* (2020.01); *G06F 40/242* (2020.01); *G06F 40/279* (2020.01); *G06F 40/30* (2020.01); *G06F 40/45* (2020.01); *G06F 40/47* (2020.01); *G06F 40/58* (2020.01); *G06N 3/0442* (2023.01); *G06N 3/0455* (2023.01); *G06N 3/0499* (2023.01); *G06N 3/08* (2013.01); *G06N 5/02* (2013.01); *G06Q 10/1053* (2013.01); *G06Q 30/0255* (2013.01); *G06Q 30/0257* (2013.01); *G06Q 30/0631* (2013.01); *G10L 15/16* (2013.01); *G10L 15/1815* (2013.01); *G10L 15/22* (2013.01); *G10L 15/26* (2013.01); *G10L 25/63* (2013.01); *G16H 10/60* (2018.01); *H04L 51/02* (2013.01); *G06N 3/091* (2023.01); *G10L 2015/088* (2013.01)

(56) References Cited

U.S. PATENT DOCUMENTS

| | | |
|---|---|---|
| 6,085,186 A | 7/2000 | Christianson et al. |
| 6,246,977 B1 | 6/2001 | Messerly et al. |
| 7,085,708 B2 | 8/2006 | Manson |
| 7,231,633 B2 | 6/2007 | Grassens |
| 7,418,443 B2 | 8/2008 | Yoshimura et al. |
| 7,636,697 B1 | 12/2009 | Dobson et al. |
| 7,725,307 B2 | 5/2010 | Bennett |
| 8,352,474 B2 | 1/2013 | Pickens et al. |
| 8,620,872 B1 | 12/2013 | Killalea |
| 8,818,862 B2 | 8/2014 | Sweeney |
| 8,838,659 B2 | 9/2014 | Tunstall-Pedoe |
| 8,924,928 B1 | 12/2014 | Belovich |
| 9,286,910 B1 | 3/2016 | Li et al. |
| 9,355,358 B1 | 5/2016 | Kramer |
| 9,368,105 B1 | 6/2016 | Freed et al. |
| 9,436,681 B1 | 9/2016 | Tunstall-Pedoe et al. |
| 9,489,418 B2 | 11/2016 | Brodsky et al. |
| 9,646,260 B1 | 5/2017 | Tunstall-Pedoe et al. |
| 9,659,052 B1 | 5/2017 | Glennon et al. |
| 9,697,255 B2 | 7/2017 | Schöning |
| 9,734,242 B2 | 8/2017 | Millington |
| 9,762,637 B2 | 9/2017 | Bullotta et al. |
| 9,876,673 B2 | 1/2018 | Margalit et al. |
| 9,928,015 B2 | 3/2018 | Eda et al. |
| 10,068,174 B2 | 9/2018 | Aili et al. |
| 10,192,546 B1 | 1/2019 | Piersol et al. |
| 10,303,798 B2 * | 5/2019 | Stubley ............... G06F 16/3329 |
| 10,326,863 B2 | 6/2019 | Muthyala et al. |
| 10,380,708 B1 | 8/2019 | Wong et al. |
| 10,387,575 B1 | 8/2019 | Shen et al. |
| 10,410,107 B2 | 9/2019 | Romero |
| 10,460,729 B1 | 10/2019 | Sun et al. |
| 10,515,125 B1 | 12/2019 | Lavergne |
| 10,535,003 B2 | 1/2020 | Parker et al. |
| 10,552,543 B2 * | 2/2020 | Hirzel ............... G06F 16/24522 |
| 10,565,509 B2 | 2/2020 | London |
| 10,581,765 B2 * | 3/2020 | Koukoumidis ....... G06F 16/248 |
| 10,679,001 B2 | 6/2020 | Rogynskyy et al. |
| 10,747,801 B2 | 8/2020 | Accardo et al. |
| 10,748,546 B2 | 8/2020 | Kim et al. |
| 10,755,177 B1 | 8/2020 | Dabney et al. |
| 10,783,159 B2 | 9/2020 | Boston et al. |
| 10,866,989 B1 | 12/2020 | Chandler et al. |
| 10,872,083 B2 | 12/2020 | Lin et al. |
| 10,885,285 B2 | 1/2021 | Och et al. |
| 10,902,210 B2 | 1/2021 | Arvela et al. |
| 11,023,468 B2 | 6/2021 | Weyerhaeuser et al. |
| 11,043,208 B1 | 6/2021 | Michelin et al. |
| 11,043,222 B1 | 6/2021 | Eagan et al. |
| 11,055,027 B1 | 7/2021 | Lee |
| 11,055,305 B1 | 7/2021 | Petricek et al. |
| 11,069,353 B1 | 7/2021 | Gao et al. |
| 11,080,304 B2 | 8/2021 | Jain et al. |
| 11,087,759 B2 | 8/2021 | Lemay et al. |
| 11,132,504 B1 | 9/2021 | Mont-Reynaud et al. |
| 11,200,075 B2 | 12/2021 | Jung et al. |
| 11,281,863 B2 | 3/2022 | Keskar et al. |
| 11,301,811 B2 | 4/2022 | Marom et al. |
| 11,301,814 B2 | 4/2022 | Radzewsky et al. |
| 11,302,310 B1 | 4/2022 | Gandhe et al. |
| 11,410,128 B2 | 8/2022 | Radzewsky et al. |
| 11,423,885 B2 | 8/2022 | Sharifi et al. |
| 11,442,992 B1 | 9/2022 | Moon et al. |
| 11,487,520 B2 | 11/2022 | Creel et al. |
| 11,501,255 B2 | 11/2022 | Mann et al. |
| 11,657,094 B2 | 5/2023 | Moon et al. |
| 11,657,233 B2 | 5/2023 | Keskar et al. |
| 11,748,577 B1 | 9/2023 | Aberle |
| 11,763,096 B2 | 9/2023 | Tunstall-Pedoe et al. |
| 11,769,017 B1 | 9/2023 | Gray et al. |
| 11,829,725 B2 | 11/2023 | Tunstall-Pedoe et al. |
| 11,840,258 B2 | 12/2023 | Shalev-Shwartz et al. |
| 2002/0087313 A1 | 7/2002 | Lee et al. |
| 2002/0173971 A1 | 11/2002 | Stirpe et al. |
| 2003/0130976 A1 | 7/2003 | Au |

(56) References Cited

U.S. PATENT DOCUMENTS

| | | |
|---|---|---|
| 2004/0054626 A1 | 3/2004 | Fuentes |
| 2004/0078756 A1 | 4/2004 | Napper et al. |
| 2004/0117189 A1 | 6/2004 | Bennett |
| 2004/0174976 A1 | 9/2004 | Elliott |
| 2005/0197825 A1 | 9/2005 | Hagerman et al. |
| 2005/0261889 A1 | 11/2005 | Iwakura |
| 2007/0043708 A1 | 2/2007 | Tunstall-Pedoe |
| 2007/0055656 A1 | 3/2007 | Tunstall-Pedoe |
| 2007/0094224 A1 | 4/2007 | Au |
| 2007/0136222 A1 | 6/2007 | Horvitz |
| 2007/0197882 A1 | 8/2007 | Smith et al. |
| 2008/0033987 A1 | 2/2008 | Carter |
| 2008/0046250 A1 | 2/2008 | Agapi et al. |
| 2008/0065974 A1 | 3/2008 | Campbell |
| 2008/0097748 A1 | 4/2008 | Haley et al. |
| 2008/0319735 A1 | 12/2008 | Kambhatla et al. |
| 2009/0024590 A1 | 1/2009 | Sturge et al. |
| 2009/0106612 A1 | 4/2009 | Pandey et al. |
| 2009/0192968 A1 | 7/2009 | Tunstall-Pedoe |
| 2010/0054154 A1 | 3/2010 | Lambert et al. |
| 2010/0088686 A1 | 4/2010 | Langworthy et al. |
| 2010/0121839 A1 | 5/2010 | Meyer et al. |
| 2010/0174692 A1 | 7/2010 | Meyer et al. |
| 2010/0205167 A1 | 8/2010 | Tunstall-Pedoe et al. |
| 2010/0228724 A1 | 9/2010 | Petri et al. |
| 2010/0235162 A1 | 9/2010 | Faddoul et al. |
| 2010/0306054 A1 | 12/2010 | Drake et al. |
| 2011/0093500 A1 | 4/2011 | Meyer et al. |
| 2011/0238408 A1 | 9/2011 | Larcheveque et al. |
| 2011/0301941 A1 | 12/2011 | De |
| 2011/0307435 A1 | 12/2011 | Overell et al. |
| 2011/0320187 A1 | 12/2011 | Motik et al. |
| 2012/0069131 A1 | 3/2012 | Abelow |
| 2012/0259621 A1 | 10/2012 | Anisimovich et al. |
| 2012/0259891 A1 | 10/2012 | Edoja |
| 2013/0013580 A1 | 1/2013 | Geller et al. |
| 2013/0042000 A1 | 2/2013 | Machida |
| 2013/0125102 A1 | 5/2013 | Kimura |
| 2013/0145288 A1 | 6/2013 | Zadeh et al. |
| 2013/0246322 A1 | 9/2013 | De Sousa Webber |
| 2013/0254182 A1 | 9/2013 | Tunstall-Pedoe |
| 2013/0332147 A1 | 12/2013 | Corfield |
| 2014/0032219 A1 | 1/2014 | Lerner et al. |
| 2014/0046891 A1 | 2/2014 | Banas |
| 2014/0108313 A1 | 4/2014 | Heidasch |
| 2014/0143533 A1 | 5/2014 | Ganong et al. |
| 2014/0150117 A1 | 5/2014 | Yamahara |
| 2014/0156614 A1 | 6/2014 | Krappe |
| 2014/0258261 A1 | 9/2014 | Singh et al. |
| 2014/0351281 A1 | 11/2014 | Tunstall-Pedoe |
| 2014/0359554 A1 | 12/2014 | Ritter et al. |
| 2014/0372119 A1 | 12/2014 | Parada et al. |
| 2015/0019462 A1 | 1/2015 | De et al. |
| 2015/0052138 A1 | 2/2015 | Sutton et al. |
| 2015/0066475 A1 | 3/2015 | Azzam et al. |
| 2015/0142704 A1 | 5/2015 | London |
| 2015/0205942 A1 | 7/2015 | Yang et al. |
| 2015/0220515 A1 | 8/2015 | Anisimovich et al. |
| 2015/0261744 A1 | 9/2015 | Suenbuel et al. |
| 2015/0271229 A1 | 9/2015 | Bullotta et al. |
| 2015/0347274 A1 | 12/2015 | Taylor et al. |
| 2016/0098387 A1 | 4/2016 | Bruno et al. |
| 2016/0171050 A1 | 6/2016 | Das |
| 2016/0179934 A1 | 6/2016 | Stubley et al. |
| 2016/0191513 A1 | 6/2016 | Tomlinson et al. |
| 2016/0196162 A1 | 7/2016 | Raman et al. |
| 2016/0203327 A1 | 7/2016 | Akkiraju et al. |
| 2016/0224541 A1 | 8/2016 | Yakovlev et al. |
| 2016/0246777 A1 | 8/2016 | Moldoveanu |
| 2016/0294755 A1 | 10/2016 | Prabhu |
| 2016/0357731 A1 | 12/2016 | Zorzin |
| 2017/0060831 A1 | 3/2017 | Smythe et al. |
| 2017/0061248 A1 | 3/2017 | Ryan et al. |
| 2017/0085595 A1 | 3/2017 | Ng et al. |
| 2017/0124220 A1 | 5/2017 | Krueger et al. |
| 2017/0125013 A1 | 5/2017 | Yan |
| 2017/0132019 A1 | 5/2017 | Karashchuk et al. |
| 2017/0140007 A1 | 5/2017 | Agarwal et al. |
| 2017/0148430 A1 | 5/2017 | Lee |
| 2017/0161279 A1 | 6/2017 | Franceschini et al. |
| 2017/0220929 A1 | 8/2017 | Rozen et al. |
| 2017/0235783 A1 | 8/2017 | Chen et al. |
| 2017/0242886 A1 | 8/2017 | Jolley et al. |
| 2017/0242899 A1 | 8/2017 | Jolley et al. |
| 2017/0243107 A1 | 8/2017 | Jolley et al. |
| 2017/0289305 A1 | 10/2017 | Liensberger et al. |
| 2017/0300831 A1 | 10/2017 | Gelfenbeyn et al. |
| 2017/0345420 A1 | 11/2017 | Barnett |
| 2017/0371861 A1 | 12/2017 | Barborak et al. |
| 2018/0011838 A1 | 1/2018 | Beller et al. |
| 2018/0011843 A1 | 1/2018 | Lee et al. |
| 2018/0032930 A1 | 2/2018 | Kolb et al. |
| 2018/0060823 A1 | 3/2018 | Garimella et al. |
| 2018/0068031 A1 | 3/2018 | Hewavitharana et al. |
| 2018/0075084 A1 | 3/2018 | Hunicken et al. |
| 2018/0075359 A1 | 3/2018 | Brennan et al. |
| 2018/0089281 A1 | 3/2018 | Li et al. |
| 2018/0137155 A1 | 5/2018 | Majumdar |
| 2018/0150739 A1 | 5/2018 | Wu |
| 2018/0154899 A1 | 6/2018 | Tiwari et al. |
| 2018/0157720 A1 | 6/2018 | Bhave et al. |
| 2018/0157960 A1 | 6/2018 | Holmes et al. |
| 2018/0189385 A1 | 7/2018 | Sun et al. |
| 2018/0196873 A1 | 7/2018 | Yerebakan et al. |
| 2018/0217981 A1 | 8/2018 | Rakshit |
| 2018/0276718 A1 | 9/2018 | Thomas et al. |
| 2018/0288104 A1 | 10/2018 | Padilla et al. |
| 2018/0330589 A1 | 11/2018 | Horling |
| 2018/0336183 A1 | 11/2018 | Lee et al. |
| 2018/0336356 A1 | 11/2018 | Papaxenopoulos et al. |
| 2018/0349158 A1 | 12/2018 | Swersky et al. |
| 2018/0366118 A1 | 12/2018 | Lovitt et al. |
| 2018/0376003 A1 | 12/2018 | Shinseki |
| 2019/0018839 A1 | 1/2019 | Ge et al. |
| 2019/0034792 A1 | 1/2019 | Kataria et al. |
| 2019/0087417 A1 | 3/2019 | Wang et al. |
| 2019/0095428 A1 | 3/2019 | Asano et al. |
| 2019/0114593 A1 | 4/2019 | Champaneria |
| 2019/0115008 A1 | 4/2019 | Jiang et al. |
| 2019/0138606 A1 | 5/2019 | Tu et al. |
| 2019/0156818 A1 | 5/2019 | Piersol et al. |
| 2019/0206400 A1 | 7/2019 | Cui et al. |
| 2019/0208024 A1 | 7/2019 | Jablonski |
| 2019/0236085 A1 | 8/2019 | Galitsky |
| 2019/0236464 A1 | 8/2019 | Feinson et al. |
| 2019/0258461 A1 | 8/2019 | Li et al. |
| 2019/0266250 A1 | 8/2019 | Toplyn |
| 2019/0294672 A1 | 9/2019 | Matskevich et al. |
| 2019/0295440 A1 | 9/2019 | Hadad |
| 2019/0295547 A1 | 9/2019 | Gandhi et al. |
| 2019/0303442 A1 | 10/2019 | Peitz et al. |
| 2019/0325068 A1 | 10/2019 | Lai et al. |
| 2019/0340291 A1 | 11/2019 | Raman et al. |
| 2019/0342339 A1 | 11/2019 | Nanda et al. |
| 2020/0004831 A1 | 1/2020 | Burceanu et al. |
| 2020/0013393 A1 | 1/2020 | Huang et al. |
| 2020/0065377 A1* | 2/2020 | Hirzel ............... G10L 15/22 |
| 2020/0065769 A1 | 2/2020 | Gupta et al. |
| 2020/0073983 A1 | 3/2020 | Sen et al. |
| 2020/0081882 A1 | 3/2020 | Cheriton |
| 2020/0104288 A1 | 4/2020 | Tao et al. |
| 2020/0134067 A1 | 4/2020 | Villard et al. |
| 2020/0134263 A1 | 4/2020 | Oh et al. |
| 2020/0151773 A1* | 5/2020 | Peppel ............ G06Q 30/0271 |
| 2020/0184158 A1 | 6/2020 | Kuczmarski et al. |
| 2020/0184963 A1 | 6/2020 | Joseph et al. |
| 2020/0184966 A1 | 6/2020 | Yavagal |
| 2020/0193264 A1 | 6/2020 | Zavesky et al. |
| 2020/0219495 A1 | 7/2020 | Alkan et al. |
| 2020/0233927 A1 | 7/2020 | Berger et al. |
| 2020/0242142 A1* | 7/2020 | Connell, II ......... G06F 16/3329 |
| 2020/0257988 A1 | 8/2020 | Creel et al. |
| 2020/0264900 A1 | 8/2020 | Cheriton |
| 2020/0267160 A1 | 8/2020 | Lees et al. |

(56) References Cited

U.S. PATENT DOCUMENTS

| | | |
|---|---|---|
| 2020/0272485 A1 | 8/2020 | Karashchuk et al. |
| 2020/0272915 A1 | 8/2020 | Tata et al. |
| 2020/0285968 A1 | 9/2020 | Tse et al. |
| 2020/0311146 A1 | 10/2020 | Guo et al. |
| 2020/0320082 A1 | 10/2020 | Schwing et al. |
| 2020/0320130 A1 | 10/2020 | Korpman et al. |
| 2020/0334580 A1* | 10/2020 | Sheopuri ............... G06F 40/56 |
| 2020/0372218 A1 | 11/2020 | Ukrainets et al. |
| 2020/0380889 A1 | 12/2020 | Fitzpatrick et al. |
| 2020/0387677 A1 | 12/2020 | Kim et al. |
| 2020/0394190 A1 | 12/2020 | Chaudhuri et al. |
| 2020/0395005 A1 | 12/2020 | Zheng et al. |
| 2020/0401766 A1 | 12/2020 | Brinig et al. |
| 2021/0011673 A1 | 1/2021 | Masai |
| 2021/0027770 A1 | 1/2021 | Olabiyi et al. |
| 2021/0042824 A1 | 2/2021 | Tarler et al. |
| 2021/0056113 A1 | 2/2021 | Mac An Tsaoir et al. |
| 2021/0056950 A1 | 2/2021 | Niehaus et al. |
| 2021/0056970 A1 | 2/2021 | Jain et al. |
| 2021/0065126 A1 | 3/2021 | Bykov et al. |
| 2021/0065685 A1 | 3/2021 | Hwang |
| 2021/0065693 A1 | 3/2021 | Sharifi et al. |
| 2021/0081814 A1 | 3/2021 | Sidorkin et al. |
| 2021/0089703 A1 | 3/2021 | Misawa et al. |
| 2021/0104100 A1 | 4/2021 | Whitney et al. |
| 2021/0104220 A1 | 4/2021 | Mennicken et al. |
| 2021/0117553 A1 | 4/2021 | Shpurov et al. |
| 2021/0120206 A1 | 4/2021 | Liu et al. |
| 2021/0134268 A1 | 5/2021 | Huang et al. |
| 2021/0144107 A1* | 5/2021 | Liang .................. G06N 5/04 |
| 2021/0150138 A1 | 5/2021 | Lanphear et al. |
| 2021/0173718 A1 | 6/2021 | Patel et al. |
| 2021/0174794 A1 | 6/2021 | Mont-Reynaud |
| 2021/0191988 A1 | 6/2021 | Galitsky |
| 2021/0192321 A1 | 6/2021 | Zhang |
| 2021/0192412 A1 | 6/2021 | Krishnaswamy |
| 2021/0193121 A1 | 6/2021 | Li |
| 2021/0201110 A1 | 7/2021 | Qin |
| 2021/0209070 A1 | 7/2021 | Latorre et al. |
| 2021/0224486 A1 | 7/2021 | Stabler et al. |
| 2021/0241381 A1 | 8/2021 | Neumann |
| 2021/0256049 A1 | 8/2021 | Byron et al. |
| 2021/0256375 A1 | 8/2021 | Menick et al. |
| 2021/0279621 A1 | 9/2021 | Lin et al. |
| 2021/0294977 A1 | 9/2021 | Soryal et al. |
| 2021/0303562 A1 | 9/2021 | Ludwig et al. |
| 2021/0319344 A1 | 10/2021 | Tang et al. |
| 2021/0342785 A1 | 11/2021 | Mann et al. |
| 2021/0350915 A1 | 11/2021 | Letinic |
| 2021/0365773 A1 | 11/2021 | Subramanian et al. |
| 2021/0367961 A1 | 11/2021 | Kuppa et al. |
| 2021/0375272 A1 | 12/2021 | Madwed et al. |
| 2021/0390553 A1 | 12/2021 | Brinig et al. |
| 2021/0406840 A1 | 12/2021 | Deluca et al. |
| 2021/0409283 A1 | 12/2021 | Smith et al. |
| 2022/0035881 A1 | 2/2022 | Levy et al. |
| 2022/0036153 A1 | 2/2022 | O'Malia et al. |
| 2022/0043702 A1 | 2/2022 | Haines |
| 2022/0050840 A1 | 2/2022 | Parravicini et al. |
| 2022/0060565 A1 | 2/2022 | Cherry et al. |
| 2022/0067283 A1 | 3/2022 | Bellegarda et al. |
| 2022/0067520 A1 | 3/2022 | Dalli et al. |
| 2022/0067540 A1 | 3/2022 | Ferrucci et al. |
| 2022/0075944 A1 | 3/2022 | Du et al. |
| 2022/0114361 A1 | 4/2022 | Kale et al. |
| 2022/0115008 A1 | 4/2022 | Pust et al. |
| 2022/0132179 A1 | 4/2022 | Bennett-James et al. |
| 2022/0138849 A1 | 5/2022 | Henson et al. |
| 2022/0148741 A1 | 5/2022 | Griffor et al. |
| 2022/0180060 A1 | 6/2022 | Jain et al. |
| 2022/0237368 A1 | 7/2022 | Tran |
| 2022/0261817 A1 | 8/2022 | Ferrucci et al. |
| 2022/0270597 A1 | 8/2022 | Qiu et al. |
| 2022/0292092 A1 | 9/2022 | Brown et al. |
| 2022/0326880 A1 | 10/2022 | Cook |
| 2022/0328039 A1 | 10/2022 | Avijeet |
| 2022/0342932 A1 | 10/2022 | Monk et al. |
| 2022/0382995 A1 | 12/2022 | Lee et al. |
| 2022/0398827 A1 | 12/2022 | Lewis |
| 2022/0405852 A1 | 12/2022 | Fohr et al. |
| 2023/0020886 A1 | 1/2023 | Mahapatra et al. |
| 2023/0074406 A1 | 3/2023 | Baeuml et al. |
| 2023/0083512 A1 | 3/2023 | Newman et al. |
| 2023/0206002 A1 | 6/2023 | Tunstall-Pedoe et al. |
| 2023/0311335 A1 | 10/2023 | Hausman et al. |
| 2023/0315983 A1 | 10/2023 | Seth et al. |
| 2023/0316006 A1 | 10/2023 | Tunstall-Pedoe et al. |

FOREIGN PATENT DOCUMENTS

| | | |
|---|---|---|
| WO | 2019148108 A1 | 8/2019 |
| WO | 2021089129 A1 | 5/2021 |
| WO | 2023278135 A2 | 1/2023 |

OTHER PUBLICATIONS

"CYC Technology Overview," [online] www.cyc.com, published in 2019.

Amorim et al., Proceedings of the 10th Acm Sigplan Intl. Conf. on Software Language Engineering, "Deep priority conflicts in the wild: a pilot study," pp. 55-66 (2017).

Chakraborty, et al., "Introduction to neural network based approaches for question answering over knowledge graphs," arXiv preprint arXiv: 1907.09361, pp. 1-34 (2019).

Chung, et al., "Parallel natural language processing on a semantic network array processor," IEEE Transactions on Knowledge and Data Engineering 7.3, pp. 391-405 (1995).

Fedus, et al., "Switch transformers: scaling to trillion parameter models with simple and efficient sparsity," https:// arxiv.org/abs/2101.03961v1; published in Jan. 2021.

Grimm, S., "Knowledge representation and ontologies," Scientific data mining and knowledge discovery: principles and foundations, Berlin, Heidelberg: Springer Berlin Heidelberg, pp. 111-137 (2009).

He, Di, et al., "Decoding with value networks for neural machine translation," Advances in Neural information processing systems 30 (2017).

Kmail, Aseel, et al., "An automatic online recruitment system based on exploiting multiple semantic resources and concept-relatedness measures," 2015 IEEE 27th Intl. Conf. on Tools with Artificial Intelligence (ICTAI), IEEE (2015).

Korney, "Knowledge Graphs in End-User Products: From Cyc to AI Assistants," published Feb. 25, 2020.

Leach et al., "RFC 4122: A universally unique identifier (Uuid) Urn namespace" pp. 1-32 (2005).

Mabbu, "A Semantic Knowledge engine Using Automated Knowledge Extraction from World Wide Web," Wichita State University, pp. 1-51 (2015).

Mochalova, Anastasia, "Search for Answers in Ontological-Semantic Graph", pp. 174-180; Retrieved from the Internet: URL: https://www.fruct.org/publications/ain1-abstract/files/Moc.pdf [retrieved on Dec. 10, 2021, Jan. 1, 2015.

Segaert, Katrien, et al., "Shared syntax in language production and language comprehension—an fMRI stydy," Cerebral Cortex 22.7, 1662-1670 (2012).

Sharma, et al., "Simulation-based approach to efficient commonsense reasoning in very large knowledge bases," Proc. of the AAAI Conf. on Artificial Intelligence, vol. 33, No. 1 (2019).

Shi, Chen, et al., "Knowledge-based semantic embedding for machine translation," Proc. of the 54th Annual Mtg of the Assoc. for Computational Linguistics, vol. 1: Long Papers; (2016).

Slonneger et al., title={Formal syntax and semantics of programming languages}, vol. 340, pp. 2-19 (1995).

Song, Linfeng, et al., "Semantic neural machine translation using AMR," Transactions of the Assoc. for Computational Linguistics 7, 19-31 (2019).

Sowa, John F., "Conceptual graphs for representing conceptual structures," Conceptual Structures in Practice, pp. 119-154 (2016).

(56) References Cited

OTHER PUBLICATIONS

Tunstall-Pedoe, W. , "True knowledge: Open-domain question answering using structured knowledge and inference," AI Magazine, pp. 80-92 (2010).
Weiss , et al., "Sequence-to-Sequence Models Can Directly Translate Foreign Speech," (arXiv: 1703.08581v2[cs.CL] Jun. 12, 2017).
Yang , et al., "Towards Making the Most of BERT in Neural Machine Translation," arXiv: 1908.05672 [cs. CL], pp. 1-10 (2019).
Zhang, Jiajun , et al., "Deep Neural Networks in Machine Translation: An Overview," IEEE Intell. Syst. 30.5, 16-25 (2015).

\* cited by examiner a    I think these are a great match!

"7 years experience of C++"
"at least five years experience of programming a major object-oriented language My explanation for this is that:

I've worked out that 7 years is within the range at least 5 years
I know that C++ is a programming language
I know that C++ is a major object-oriented programming language
Therefore, experience of C++ implies experience programming a major object-oriented programming language
Therefore, 7 years experience of C++ implies at least five years experience of programming a major object-oriented programming language b    Detailed explanation:

I know that 7 is greater than 5
Therefore, 7 is within the range at least 5
Therefore, 7 years is within the range at least 5 years
I know that C++ is a programming language
I know that C++ is a major object-oriented programming language
Therefore, programming C++ implies programming a major object-oriented programming language
Therefore, experience programming C++ implies experience programming a major object-oriented programming language
Therefore, experience of C++ implies experience programming a major object-oriented programming language
Therefore, 7 years experience of C++ implies at least five years experience of programming a major object-oriented programming language

FIGURE 7

COMPUTER IMPLEMENTED METHOD FOR THE AUTOMATED ANALYSIS OR USE OF DATA

CROSS-REFERENCE TO RELATED APPLICATIONS

This application is a continuation of U.S. application Ser. No. 18/469,128, filed on Sep. 18, 2023, which is a continuation of U.S. application Ser. No. 18/088,574, filed on Dec. 25, 2022, which is a continuation of U.S. application Ser. No. 18/001,368, filed on Dec. 9, 2022, which claims the priority of International Application No. PCT/GB2021/052196, filed on Aug. 24, 2021, which claims priority to GB Application No. GB 2013207.2, filed on Aug. 24, 2020; GB Application No. GB 2014876.3, filed Sep. 21, 2020; and GB Application No. 2020164.6, filed on Dec. 18, 2020, the entire contents of which are fully incorporated herein by reference.

BACKGROUND OF THE INVENTION

1. Field of the Invention

The field of the invention relates to a computer implemented method for the automated analysis or use of data; one implementation is a voice assistant that is able to analyse, interpret and act on natural language spoken and text inputs.

2. Technical Background

Natural language (NL) is language evolved for humans such as the English language. Although significant advances have been made in computers' ability to process natural language, computers are still not able to deeply understand the meaning of natural language and use that meaning internally.

For this reason most computer applications typically use structured data to store information that they need for processing—e.g. a relational database: designing the schema, populating the database and writing code to process the fields in the database.

Use of structured data can work well if the application has limited requirements for the type of data required. However, some applications naturally require an extremely broad, heterogeneous collection of data to work well. This means that the schema required would have to be enormous, making building and coding for such an application impractical. We refer to such applications herein as HUB applications (Heterogeneous and Unreasonably Broad).

Examples of HUB applications include an application for managing a person's general health data where there are thousands of tests, thousands of medical conditions and thousands of symptoms. Another related application could be a nutrition tracking application where there are many thousands of substances and foods that can be ingested, each with different metabolic effects on the body.

Another example is an application to match the résumé of potential candidates with a job specification: in principle such an application would need structured data to represent every skill that might be of value to any role, every type of experience, every type of previous job.

Accounting is another application where vast heterogeneous data would be valuable: the perfect accounting application would represent every type of contract, every type of service.

In practice some of these applications, where they exist, work with a limited schema that doesn't cover the full range of their ideal properties. Health applications for example, typically work like this ignoring many types of data that they do not cover and instead end up being narrow—limiting the application to only certain verticals within health.

Applications may also use natural language or augment a limited schema with natural language—such as with current résumé matching applications which might represent a few key skills in a structured form but rely largely on keyword searching or statistical natural language processing (NLP) techniques on written résumés otherwise.

In the case of accounting, transactions are represented with limited structured data—debits and credits on virtual ledgers with natural language names. The meaning of the natural language names and thus what these transactions represent is generally opaque to the application. Virtual ledgers often group different types of transaction together but fail to represent semantic differences which may be important.

There is no exact threshold for when an application becomes a HUB application but the difficulty of building an application with a hand created schema grows more than linearly with the number of tables as managing these tables as well as the code that maintains them becomes increasingly difficult to do.

These issues could be addressed if there existed a language or way of representing data that computers could fully process and understand but that also had an extremely broad scope.

In conventional Artificial Intelligence (AI), statistical Machine Learning (ML)—particularly Deep Learning (DL)—has been widely used. This has provided significant progress with many problems. Despite the progress, the results cannot be explained in a way that makes sense to human users as the solutions are the result of a calculation that may involve billions of weights. It can also be argued that the system lacks 'real' understanding of the data or at least that the understanding is very different from the way a human user would understand it.

3. Discussion of Related Art

The Wikipedia page about Cyc, of 18 Jul. 2019, states that Cyc is the world's longest-lived artificial intelligence project, attempting to assemble a comprehensive ontology and knowledge base that spans the basic concepts and "rules of thumb" about how the world works (think common sense knowledge but focusing more on things that rarely get written down or said, in contrast with facts one might find somewhere on the internet or retrieve via a search engine or Wikipedia), with the goal of enabling AI applications to perform human-like reasoning and be less "brittle" when confronted with novel situations that were not preconceived.

The Wikipedia page about Cyc, of 18 Jul. 2019, states that the objective of the Cyc project was to codify, in machine-usable form, the millions of pieces of knowledge that compose human common sense; this entailed, along the way, (1) developing an adequately expressive representation language, CycL, (2) developing an ontology spanning all human concepts down to some appropriate level of detail, (3) developing a knowledge base on that ontological framework, comprising all human knowledge about those concepts down to some appropriate level of detail, and (4) developing an inference engine exponentially faster than those used in then-conventional expert systems, to be able to infer the same types and depth of conclusions that humans are capable of, given their knowledge of the world.

The Wikipedia page about Cyc, of 18 Jul. 2019, states that most of Cyc's knowledge, outside math and games, is only true by default; for example, Cyc knows that as a default parents love their children, when you're made happy you smile, taking your first step is a big accomplishment, when someone you love has a big accomplishment that makes you happy, and only adults have children; when asked whether a picture captioned "Someone watching his daughter take her first step" contains a smiling adult person, Cyc can logically infer that the answer is Yes, and "show its work" by presenting the step by step logical argument using those five pieces of knowledge from its knowledge base: these are formulated in the language CycL, which is based on predicate calculus and has a syntax similar to that of the Lisp programming language.

The Wikipedia page about Cyc, of 18 Jul. 2019, states that the Cyc project has been described as "one of the most controversial endeavors of the artificial intelligence history"; Catherine Havasi, CEO of Luminoso, says that Cyc is the predecessor project to IBM's Watson; machine-learning scientist Pedro Domingos refers to the project as a "catastrophic failure" for several reasons, including the unending amount of data required to produce any viable results and the inability for Cyc to evolve on its own; Robin Hanson, a professor of economics at George Mason University, gives a more balanced analysis: "Of course the CYC project is open to criticism on its many particular choices. People have complained about its logic-like and language-like representations, about its selection of prototypical cases to build from (e.g., encyclopedia articles), about its focus on answering over acting, about how often it rebuilds vs. maintaining legacy systems, and about being private vs. publishing everything. But any large project like this would produce such disputes, and it is not obvious any of its choices have been seriously wrong. They had to start somewhere, and in my opinion they have now collected a knowledge base with a truly spectacular size, scope, and integration. Other architectures may well work better, but if knowing lots is anywhere near as important as Lenat thinks, I'd expect serious AI attempts to import CYC's knowledge, translating it into a new representation. No other source has anywhere near CYC's size, scope, and integration."

The True Knowledge system provided open-domain question answering using structured knowledge and inference. In the True Knowledge system, knowledge in the knowledge base was represented in a single unified format: named relations between pairs of named entities referred to as "facts." Facts, and the relations themselves, were first-class entities so facts about facts and facts about the properties of relations were fully supported (Tunstall-Pedoe, W. (2010). True Knowledge: Open-Domain Question Answering Using Structured Knowledge and Inference. AI Magazine, 31(3), 80-92. https://doi.org/10.1609/aimag.v31i3.2298).

SUMMARY OF THE INVENTION

According to a first aspect of the invention, a computer implemented method for the automated analysis or use of data, comprises the steps of:
(a) storing in a memory a structured, machine-readable representation of data that conforms to a machine-readable language ('machine representation'); the machine representation including representations of user speech or text input to a human/machine interface;
(b) automatically processing the machine representations to analyse the user speech or text input.

In a second aspect, a computer-based system configured to analyse data, the system is configured to:
(a) store in a memory a structured, machine-readable representation of data that conforms to a machine-readable language; the structured, machine-readable representation of data including representations of user speech or text input to a human/machine interface;
(b) automatically process the structured representations to analyse the user speech or text input to a human/machine interface.

These aspects of the invention may be implemented in a voice assistant or chatbot; the technical advantage achieved is to enable more extensive and faster scaling of the voice assistant or chatbot's capabilities; the invention enables voice assistants and chatbot to be able to answer a broader range of questions, and to do so more accurately; the invention makes it easier for the voice assistant or chatbot to work with large numbers of different natural languages.

One point of interpretation: the conjunction 'or' should not be narrowly construed to indicate mutual exclusivity but to cover inclusivity too. Hence, the phrase 'user speech or text input' means 'user speech on its own, or user text on its own, or both user speech and also user text'. When the conjunction 'or' is meant exclusively, the phrase 'either . . . or' is used.

The machine-readable language is extremely expressive yet also extremely simple; simplicity requires less computer processing and thus delivers faster performance. Further details of the invention are in the appended Claims.

According to a further aspect of the invention, there is provided a computer system including a processor and a memory, the processor configured to answer a question, the processor configured to use a processing language in which semantic nodes are represented in the processing language, the semantic nodes including semantic links between semantic nodes wherein the semantic links are themselves semantic nodes, in which each semantic node denotes one specific meaning, in which a combination of semantic nodes defines a semantic node, in which expressions in the processing language may be nested, in which the question is represented in the processing language, in which reasoning steps are represented in the processing language to represent semantics of the reasoning steps, in which computation units are represented in the processing language, wherein the memory is configured to store the representations in the processing language, and wherein the processor is configured to answer the question using the reasoning steps, the computation units and the semantic nodes, and to store an answer to the question in the memory.

An advantage is that because semantic links between semantic nodes are themselves semantic nodes, semantic links and semantic nodes do not need to be processed in a distinctly different way, which simplifies processing, which speeds up response times, which is a technical effect.

An advantage is that because semantic nodes are very widely used in the processing language, processing of the processing language is speeded up, which speeds up response times, which is a technical effect.

The technical effect operates at the level of the architecture of the computer system; that is to say the effect is produced irrespective of the data being processed.

The technical effect results in the computer system being made to operate in a new way, because the computer finds answers to questions faster than using prior art approaches, because semantic nodes are very widely used in the processing language, which means that processing of the processing language is speeded up.

The processing language contributes to the technical character of the invention because it produces a technical effect: a processor processing the processing language has the effect that the computer finds answers to questions faster than using prior art approaches, because semantic nodes are very widely used in the processing language, which means that processing of the processing language is speeded up.

The computer system may be configured to output the answer to the question.

The computer system may be configured to output the answer to the question to a display device.

The computer system may be one wherein expressions in the processing language may be nested with no limit inherent to the processing language.

The computer system may be one wherein the semantic nodes each includes a unique identifier.

The computer system may be one wherein the computation units are semantic nodes.

The computer system may be one wherein the question is represented in the processing language with a passage comprising a semantic node that identifies the passage as a question, a list of zero, one or more semantic nodes representing unknown entities being asked about and at least one further passage which represents the semantics of the question in the context of the zero, one or more unknown entities.

The computer system may be one wherein the processing language is universal language.

The computer system may be one wherein the processing language is not a natural language.

The computer system may be one wherein the question relates to search and analysis of documents or web pages, wherein the sematic nodes include representations of at least parts of the documents or the web pages stored in a document store.

The computer system may be one wherein the question relates to a location-based search, using mapping data represented as semantic nodes in the processing language.

The computer system may be one wherein the question relates to a search for defined advertisements or news, wherein the semantic nodes include representations of advertisements, news articles or other information items.

The computer system may be one wherein the question relates to a request for a summary of a news topic, wherein the semantic nodes include representations of news from multiple sources, e.g. to provide a summary or aggregation of the news.

The computer system may be one wherein the question relates to a request for a compatibility match between persons, wherein the semantic nodes include representations of personal information defining one or more attributes of a person, for a plurality of people.

The computer system may be one wherein the question relates to compliance with requirements preventing abusive or illegal social media postings, wherein the semantic nodes include representations of social media postings.

The computer system may be one wherein the question relates to analysing customer reviews, wherein the semantic nodes include representations of customer reviews.

The computer system may be one wherein the question relates to a user's product request, wherein the semantic nodes include representations of product descriptions and user product requests.

The computer system may be one wherein the question relates to a job search, wherein the semantic nodes include representations of job descriptions and job applicants' skills and experience, to determine which job applicants match a job description, or to determine which job descriptions match a job applicant's skills and experience.

The computer system may be one wherein the question relates to health of an individual, wherein the sematic nodes include health data relating to the individual, and health data relating to human beings.

The computer system may be one wherein the question relates to nutrition, wherein the sematic nodes include nutritional data for foods and drinks.

The computer system may be one wherein the question relates to accounting or finance, wherein the sematic nodes include representations of financial or accounting information.

The computer system may be one wherein the question is received by a voice assistant or chatbot, wherein the semantic nodes include representations of user speech input to a human/machine interface and include representations of the human/machine interface itself.

According to a further aspect of the invention, there is provided a computer-implemented method, the method using a computer system including a processor and a memory, the processor configured to use a processing language in which semantic nodes are represented in the processing language, the semantic nodes including semantic links between semantic nodes wherein the semantic links are themselves semantic nodes, in which each semantic node denotes one specific meaning, in which a combination of semantic nodes defines a semantic node, in which expressions in the processing language may be nested, in which the question is represented in the processing language, in which reasoning steps are represented in the processing language to represent semantics of the reasoning steps, in which computation units are represented in the processing language, wherein the memory is configured to store the representations in the processing language, the method including the steps of:

(i) the processor answering the question using the reasoning steps, the computation units and the semantic nodes, and (ii) the processor storing an answer to the question in the memory.

Advantages include the advantages of the previous aspect of the invention.

The method may be one wherein the question is represented in the processing language with a passage comprising a semantic node that identifies the passage as a question, a list of zero, one or more semantic nodes representing unknown entities being asked about and at least one further passage which represents the semantics of the question in the context of the zero, one or more unknown entities.

The method may be one wherein the unknowns in the question are identified and the passage making up the body of the question is selected for further analysis; processing begins on a list of passages from the body of the question and the selected unknowns; a first passage in the list of passages is selected for processing; processing a single passage comprises three methods: using statically stored processing language passages, utilising computation units and utilising processing language generated from reasoning:

in which the first method is to lookup in the passage store if there are any passages that can be directly mapped with the passage being processed; if the passage is exactly the same structure as a passage in the passage store, with all nodes matching other than the unknowns, then the values the unknowns match against are valid results;

the second method is to check if any results can be found by executing computation units; it is checked if this passage matches against any passages in a computation unit description; all non-unknown nodes in the passage being processed must match the same nodes in the corresponding position in the computation description or align with a computation input unknown; the unknowns being processed must align to output unknowns in the description; the computation unit is then called to get valid output values for the processed passage's unknowns;

the third method is to see if this passage can be proved by applying any reasoning steps;

reasoning steps are searched for where a passage in the second half of the reasoning passage can be unified with the passage being processed; all nodes and structure must be equal between the two passages, other than unknowns in the focus passage or the reasoning passage; if a reasoning passage like this is found it means that this reasoning step could be used to prove the passage being processed; a multi-stage process is used to first find any mappings for unknowns in the processed passage when matching with the reasoning passage; secondly, mappings for unknowns used in the reasoning passage are found by mapping with the passage being processed; this mapping can then be applied to the front half of the reasoning passage to generate a list of passages that, if they can be matched with known or generated processing language and mappings found for them, will prove and find valid mappings for the focus passage; solutions for the list of passages can then be found recursively.

The method may use a computer system of any aspect of the previous aspect of the invention.

Aspects of the invention may be combined.

BRIEF DESCRIPTION OF THE FIGURES

Aspects of the invention will now be described, by way of example(s), with reference to the following Figures, in which:

FIG. 7 shows examples of explanations generated. (a) shows examples of simplified explanations; (b) shows an example of a detailed explanation.

DETAILED DESCRIPTION

Figure 1:
FIG. 1 shows example screen output for a notification of a job match.

Examples of the present invention include systems and methods for creating and using a structured representation of data that is aimed to be as expressive as natural language in terms of breadth but which also can be processed and understood by automated systems. The representation referred to herein as UL (for universal language) is a preferred example. Examples of the invention include systems and methods relating to specific HUB and other applications as well as systems and methods which process, store and utilize UL.

Use of UL also brings with it other advantages beyond the delivery of HUB applications. For example, UL can be used as a way for an automated system to understand the world and as a way for an automated system to reason. As the reasoning steps are recorded in language, such systems can also fully explain themselves in language to human users. Requirements for a software system can be written in UL (referred to herein as 'tenets') and examples of the present invention can directly use these tenets to decide on actions for itself, rather than having its detailed actions determined by program code with a human programmer trying to anticipate all possible scenarios and code them in advance.

Representation of Language: UL

An aim of UL is in principle to be able to represent anything expressible in any natural language. An additional aim is for anything expressed in natural language to thus be translatable into UL. The purpose of UL is to enable use by machines so this representation of data must therefore be fully processable and understandable by automated systems. Although an aim, examples of the present invention may not fully deliver these aims whilst still having significant advantages over the prior art.

There are many different properties of natural language that make getting a computer to understand and process it extremely hard. These include polysemy—the fact that words in natural language often have many meanings or senses, some related and overlapping and some completely different and that context, years of experience with the natural language and common sense knowledge is needed by people to understand which meaning is intended. For example, the English word "pen" can mean a writing implement, an enclosure for farm animals, a female swan or a prison (short for "penitentiary") among other meanings. As a verb it also has a number of related and different meanings. Despite this complexity human beings can naturally infer the intended sense of the word using context, real world experience and common sense knowledge when it appears, but this is extremely hard for a machine, which lacks the necessary skills.

Ambiguity and flexibility in the word ordering is another issue that makes natural language processing extremely hard for machines. Even simple sentences can be phrased in literally dozens of ways which convey the same meaning. Humans naturally understand these numerous phrasings but this is not easy to represent in an algorithm. Clauses and words within a sentence modify and attach to other parts of the sentence changing their meaning in ways that humans can naturally understand but which follow no clear rules that a machine can follow. Natural languages also use techniques like anaphora to refer back to entities referenced in earlier speech and avoid saying them again (e.g. in English with pronouns and words such as "he", "hers", "it", "this" etc.). Humans naturally understand what is being referred to but this is not so obvious for a machine. Ambiguity can even result from where the boundaries exist in a compound noun—for example the use of the compound noun "fruit flies" in the sentence "Fruit flies like a banana" compared with the sentence "Time flies like an arrow".

UL is designed to overcome all these issues and create a language which can be parsed, understood and processed by a machine and which thus can store an extremely broad range of information in a way that a machine can understand, process and explain.

Semantic Nodes

A key component of UL is what we call herein a semantic node. A semantic node is intended to be the broadest conceivable definition of a 'thing' that can be defined—anything there is a word for can have a semantic node in UL as well as things which have no natural language name.

In various examples, semantic nodes can include every specific human being, the concept of human being (of which any specific human being is a member), every file, every web page, every audio recording or video, specific relationships (including the relationship that links any specific human being to the concept of human being), attributes, specific types of language nuance and every row and item in a relational database table.

A semantic node once defined has an identifier so it can be referred to within UL. In a preferred example the ID is a 128-bit version 4 UUID (RFC 4122) with hyphenated lower-case syntax. For example: b1c1cb5f-248f-4871-a73f-900d29066948. A preferred example also allows Unicode strings in double quotes to be their own ID—the string itself is the ID for the semantic node for that specific string. For example, "Piña colada" is a valid semantic node representing only the string, not the concept of the drink. In other examples, a UUID or other identifier could be used for strings to simplify the syntax further, but requiring additional language to express the link between the identifier and the string it represents.

In an example, a simple grammar for UL is thus:
<passage>::=<128 bit UUID>
<passage>::="<Unicode string>"
<passage>::=(<passage><passage>*)

Where <passage>* is zero, or more further <passage> and double quotes within the Unicode String are escaped \"

In an example, a semantic node may be represented by a 128 bit UUID or a string;
a passage may be either (a) a semantic node or (b) two or more other passages in brackets.

In another example, the minimum number of passages that can be grouped within parentheses is two so the third line of the above grammar would be <passage>:= (<passage><passage><passage>*)

In a preferred example a given semantic node typically denotes one specific thing or one specific meaning. Although polysemy is permissible in a preferred example, with an essentially unlimited pool of UUIDs available there is no reason to overload a node with more than one meaning and in practice all the possible senses of a word in a natural language will be given different semantic nodes. Closely related senses of a word can also be given different semantic nodes too and their relationship described with passages. This use of unique semantic nodes for every possible sense overcomes the complexity and ambiguity from determining sense in natural languages.

The use of semantic nodes also avoids any ambiguity that comes from concepts being denoted with multiple words in natural languages. In a preferred example, compound nouns, verb phrases, prepositional verbs etc. do not generally exist—each such concept has a single node and there are no challenges for the machine in deciding where the boundaries of the representation lie.

Node Agreement

Herein we use the term "user" to mean any human, organisation or machine user of an example of the present invention. A user could be any computer system that uses an example of the invention or any human being or organisation that makes use of UL. It can also be subsystems of larger computer systems.

In a preferred example if two semantic node identifiers are different, they may or may not be the same concept—as two different users of the invention may have chosen two different IDs for the same thing. If two identifiers are the same, by design in a preferred example they must denote the same things, defined in the same way. Thus, UL becomes useful for communication when agreement happens on semantic nodes and these are adopted across different systems. UL may become understandable to human users when enough is known about semantic nodes to be able to express them in natural language and generate natural language that has similar meaning to the UL.

In a preferred example, the meaning of a semantic node comes only from other UL that represents things that have been said about the node. Sometimes this may represent the UL expressed knowledge that the semantic node corresponds exactly to a word or sense of a word in a named natural language. For example, the Spanish drink Sangria may be represented as a6ba9f28-b54d-4c4a-8cf8-ad4c07659004. Pen in the sense of a writing implement may be represented as c092849c-80ed-4a69-9a4e-2704780f0cea but the concept of a pen in the sense of an enclosure for farm animals would have a completely different node such as ba9b43a3-540d-44ff-b6fe-62dcfb9dda1c. Although these meanings may be documented somewhere for human users, passages of UL would define and semantically link these concepts to other concepts giving them meaning. For example in the case of the Sangria concept, passages may assert that it is kind of drink, that is alcoholic, that it originates in Spain. Passages may further define the ingredients or other information relevant to the machine understanding of what it is.

As used herein a "shared ID" is an ID used by more than one user of various examples of the invention. Typically, one user has created and used the ID and a second, or more users, has decided that this ID represents a concept they also want to use and has then started using it too. A "private ID" or "local ID" is similarly an ID used by only one user and is not published or exposed to other users. A "public ID" is an ID that a user has used in UL that can be seen by every user, whether it is shared or not depends on whether any other client entity has started using it. According to various examples, IDs can be shared between multiple users without being made fully public.

To express this in other words, any user of an example of the present invention can coin their own semantic nodes with their own local meaning by picking an unused identifier. For example, an application could assign a semantic ID to the rows of a particular local database table. Any number of different IDs can represent the same thing. When semantic nodes are shared, however, their meaning is shared. If another user were to then use those IDs elsewhere, they would mean the same thing and denote the same thing. In a preferred example with a 128-bit address space, selecting an ID randomly from that space has an essentially zero probability of a collision if one was not intended, enabling local IDs to be coined and used without having to undergo any kind of registration process or communication or coordination with any other user. In another example string identifiers could be used and users could include a unique substring in their own local identifiers using it e.g. as a prefix. For example, an organisation may choose a unique prefix like "unlikelyai719" and then name all its nodes starting with this e.g. "unlikelyai781_sangria"—with a unique prefix it can ensure that its local ids are not duplicated by any other user. Other examples may use a smaller address space and have a more centralised approach possibly including registration.

Strings

As previously mentioned, in a preferred example, Unicode strings also represent semantic nodes. Their meaning is strictly the string itself only. Any natural language meaning contained within the string is not part of the meaning of these IDs. i.e. "sangria" means strictly the sequence of letters s . . . a . . . n . . . g . . . r . . . i . . . a—not the concept of the drink. Following the principle of node agreement discussed above it is also possible for a string to be represented by an ID as an additional identifier. For example, the string "sangria" could be additionally represented as fc570fba-cb95-4214-bc45-8deb52d830a5 and this represented in a passage or otherwise. This can be used for very large strings. Following the same design principle, two identical strings used as semantic nodes have universal meaning as that string.

Combination Nodes

Combining semantic nodes also defines a semantic node. Shared rules around the meaning of shared nodes or shared classes to which nodes belong define further shared meaning from the combination. For example, semantic nodes within an infinite class can be represented by combining one or more nodes that define the class with one or more strings where there is a common internationally recognised representation in string form. e.g. integers can be defined this way. (<id for integer>"5"). Another example of a combination node with more than two nodes within it is (<id for group><id for Chicago><id for New York City><id for London>) which is a single semantic node representing a collection of three cities regarded as a single entity. Combination nodes can contain any finite number of semantic nodes and the semantic nodes within them can also be combination nodes creating any level of nesting.

Nesting

UL syntax allows for expressions to be nested indefinitely. This allows the user to define a concept, coupled with contextual information about the concept, as a hierarchy of UL expressions under the same parent UL expression or with the same central expression or passage. Context can be used to provide nuance, source, belief, temporal validity etc. For example, starting with a passage (HoldsOffice JoeBiden UsPresident)(where HoldsOffice JoeBiden and UsPresident are human readable "nicknames" for IDs—described further below) another passage that states when it is true could be (HasTemporalValidity (HoldsOffice GeorgeWBush UsPresident)(DateIsoFormat "2021-07-23"))—which says that Joe Biden held the office of US President on the 23$^{rd}$ of July 2021. Further expressions around this passage could assert that this statement had come from a particular source or had a certain degree of reliability etc.

Combination Agreement

In a similar way to the principle of node agreement where use of the same semantic node by the same or different entities implies identical meaning between usages, the meaning that comes from combining shared semantic nodes is also universal. Any client entity that chooses to create passages that use shared semantic nodes is also expressing the same meaning by combining them. Similarly, any client entity is free to define its own meaning to combinations of semantic nodes that are not used elsewhere.

In other words, further meaning comes from combining semantic nodes. Again, if semantic nodes are shared then the meaning that comes from combining them is also shared. In a preferred example, semantic nodes can be combined in any numbers and at any level of nesting and no further syntax is required. Other examples may include additional syntax. The combining and nesting herein and in a preferred example is done with round brackets when UL is displayed. However, various examples and implementations of examples may represent the combining of nodes in other ways. For example, the syntax could group nodes with different characters than round parentheses, there could be special function words such as "query" in the syntax that are not semantic nodes but which define different types of passage or there could be special syntax for certain types of node such as unknown values or booleans or integers.

The combinations in UL in a preferred example are expressed directly with brackets. There is no ambiguity in how the nodes are grouped or any assumed grouping when brackets are absent. This syntax thus avoids the ambiguity that is extremely common in natural languages where clauses and words group and modify other parts of a sentence in ways that are extremely hard for a machine to determine. For example, the English sentence "The police arrested the demonstrators because they feared violence" is ambiguous about whether "they feared violence" applies to the demonstrators or the police. Natural language has no rigorous grouping syntax meaning that this type of ambiguity is common. Human beings armed with considerable experience of the world can infer from common sense and their world knowledge that it is more likely to apply police in this case. Unambiguous grouping in UL ensures that a machine can always get it right.

UL Syntax

A UL expression is either a semantic node or a passage. Both variations are atomic, complete pieces of valid UL. Semantic nodes are defined fully above, and include either a UUID or a Unicode string. A passage is any combination of nodes, and it is the sole nesting construct of UL.

Passages may be anything from a single semantic node to a complex hierarchy representing an entire book.

A simple, more formal, grammar for UL in the preferred example could thus be:

universal_language
=ul_element*
|EOF
ul_element
=semantic_node
|passage
semantic_node
=version_4_uuid
|string_literal
passage='('ul_element+')'

The above grammar uses the symbols (and) to denote grouping, and omits implementation-specific details such as character escapes within string_literal nodes.

Various examples of this invention may extend or change the above grammar to suit their needs. Possible extensions include additional syntax for specific types of node: for example, integers, real numbers, points in time, unknowns. Possible other extensions include comments, ignored by any UL parser, and "named passages". Named passages could represent a way to link passages to a nickname in a human-readable language, such as English. Nicknames are further described in the following section.

Note that a preferred example uses this extremely simple syntax without extension and there is no special additional syntax for different types of passage—meaning comes purely from the choice of semantic nodes and how they are grouped both in terms of grouping and ordering. Being able to express everything with such a simple representation has significant advantages over alternatives which use more complicated syntax or use special additional syntax for particular things. These advantages include the simplicity and generality of implementation which can result in significant speed improvements when processing the language. It also greatly simplifies the storage of UL and the ability to search and process it. With more complicated syntax, different code needs to handle each of the different types of syntax. Storage is greatly complicated too. The more complicated storage also adds to the complexity of the code that needs to access it and the speed it can be accessed.

Nicknames

To make UL more understandable to humans, various examples have a 'nickname' scheme where shorter natural language labels are associated with a UL expression and those names are used when presenting UL to humans. These labels may be used as alternatives to raw UUIDs when displaying UL to humans. In a preferred example, any number of nickname schemes can be defined, enabling users familiar with different natural languages to access meaning in UL. The example nickname scheme used herein is termed English1. In some examples (but not a preferred example) these nicknames may be used as the identifier. In a preferred example, these nicknames are not identifiers but merely a way of presenting identifiers to humans.

As an example of UL representation, this is a valid passage:

(03d206a2-52ca-49e1-9aeb-86364e2dead6 cb75d6f8-16d9-4a36-8c16-7195182d4057 (d1fd5662-c88e-4d94-b807-5310483df8cd (30847a3d-e43c-4229-993e-20ad01adc126 5a533842-bcd8-4125-8b39-2b1caa643593)))

The meaning of this passage corresponds to the English "Brie is a creamy, French cheese".

Assigning these nicknames to the semantic nodes within this passage like so:
IsA=03d206a2-52ca-49e1-9aeb-86364e2dead6
Brie=cb75d6f8-16d9-4a36-8c16-7195182d4057
Cheese=d1fd5662-c88e-4d94-b807-5310483df8cd
Creamy=30847a3d-e43c-4229-993e-20ad01adc126
French=5a533842-bcd8-4125-8b39-2b1caa643593
means the above passage can be displayed in a more human readable form thus:
(IsA Brie (Cheese (Creamy French)))

Creamy and Cheese are semantic nodes that are properties or attributes of other semantic nodes. This concept (given the nickname Attribute) is a semantic node that corresponds to a class of such nodes and is shared. Part of the shared meaning in a preferred example is that two or more attributes combined make a new attribute where all the constituent attributes apply so (Creamy French) is itself an attribute meaning in English "creamy and French".

Cheese is a class meaning things which are cheeses. Another shared meaning from Class and Property is that combining a class with a property gives the class of all things in that class which have that property so (Cheese (Creamy French)) is the class of all creamy, French cheeses—"creamy, French cheese" in English.

IsA is a semantic node which has shared meaning from combining a semantic node with a class meaning the node is a member of that class so (IsA Brie (Cheese (Creamy French))) can be translated to English with "Brie is a creamy, French cheese".

Again, in a preferred example, the choice of English1 nickname is chosen to be helpful by choosing a name that corresponds to English language that approximates the meaning of the node. However, the meaning of the node only comes from its usage in the system.

Negation

To say something is not true the semantic node Not in combination with another relationship node defines a relationship node which is true whenever the original relationship is false.

e.g.
((Not IsA) Bat Bird)
is a true statement.

Questions

Questions can be represented in UL by combining a node that identifies the passage as a question with a list of zero or more unknowns and a further passage or passages which represent the semantics of the question using the zero or more unknowns. In a preferred example, the passage of UL is of the form ((Question <unknowns>)(<passage>)) where Question is a semantic node and <unknowns> is a list of zero, one or more semantic nodes representing unknown values (similar in meaning to letters of the alphabet in algebra) and where <passage> is where the unknowns are used to express what is being asked about. In a preferred example, these unknowns are simply semantic nodes, members of the class Unknown—other than their meaning they have no special status. Herein we use Unknown1, Unknown2, X etc. as nicknames for members of this class. Note that questions in a preferred example are UL passages like any other: the syntax of UL has not been extended or changed in any way to support questions.

e.g.
(Question Unknown1)((HasAttribute Unknown1 Alcoholic)(IsA Unknown1 Drink))
translates into English as "What drinks are alcoholic?" or "List alcoholic drinks")
Yes/No questions have zero unknowns so both
((Question)((IsA Sangria Drink)(HasAttribute Sangria Spanish)))
((Question)((IsA Sangria (Drink Spanish))))
translate as "Is Sangria a Spanish drink?"
Another example is:
((Question)(WithinRange (Integer "7")(AtLeast (Integer "5"))))
which is asking "Is 7 within the range 'at least 5'?" The question passage is made up of a head passage—in this case just (Question)—and a tail of other passages—in this case just (WithinRange (Integer "7")(AtLeast (Integer "5"))). The head part's first element will always be the Question node, followed by any number of unknowns that can be used to signify the outputs of the question if it is not a simple yes or no question. Only the unknowns used for outputs need to be specified here. Unknowns are just semantic nodes in the class Unknown.

An example question that uses unknowns (to be mapped to the outputs) is:
((Question Unknown1)(IsA Unknown1 (Cheese Creamy)))
Which is asking "What are the creamy cheeses?"/"List creamy cheeses?" The unknown Unknown1 is used in the question and any nodes that can be correctly mapped to Unknown1 from other things represented in UL are returned as appropriate outputs for the question.

An example of a UL question that would give No as an answer is:

((Question)(HasAttribute Cheddar Creamy))

Which is asking "Is cheddar creamy?". In examples where it is known that A. Cheddar is a hard cheese and B. that hard cheeses are not creamy the system can prove that cheddar is not creamy and will return a 'No' result.

Reasoning

Reasoning is where UL is generated from other UL. A reasoning passage is a bit of UL that represents how new UL can be generated from other UL—for example a logical consequence or giving meaning to other nodes or a combination of nodes. e.g. the English "if something originates from France then it is French" translates to a reasoning passage in UL.

Reasoning steps are represented as passages which represent the semantics of the step. Note that in a preferred example reasoning passages are represented in UL like anything else. There is no special syntax or content that extends or changes UL to support reasoning. For example:

(ConsequenceOf (IsA X (Cheese Hard))((Not HasAttribute) X Creamy))

Which says that "If X is a hard cheese then X is not creamy." In the preferred example, these reasoning steps begin with a ConsequenceOf semantic node. This is then followed by a passage which represents the conditions that need to hold for this step to be used (the 'if' passage). This can be just one passage like in this example, or it can be a passage that contains other passages which would all need to hold. The third element is a passage that is true if the conditions are met (the 'then' passage). This can also be a passage of passages, in which case all of the passages contained would be true if the conditions are met.

Some more examples of reasoning steps:
(ConsequenceOf (IsIn X Y)(IsA Y GeographicalArea)) in English is "If X is in Y then Y is a location" (IsIn represents geographical location)
(ConsequenceOf (IsA X Continent))((IsIn X Earth)) in English means "If X is a continent then X is in Earth"

Computation Units

Computation units are a way of allowing examples of the present invention to represent and make use of computation required for reasoning and other purposes. Any automatic process that calculates something or returns a result can be supported with this technique. Various examples also allow them to support actions such as completing a transaction, turning on a light, playing music etc.

As a simple example, according to various examples a computation unit might allow UL to answer questions such as "Is 7 greater than 5?" Clearly explicitly having to enter the passages for every combination of two integers would be impractical. In a preferred example, the computation unit can be thought of as a semantic node which is an example of the class ComputationUnit. We can then add passages that represents details for this unit needed to select and run it: what it can do, how to run it and how to interpret the results.

For example, here is an example computation unit for addition:

(ComputationLocalJavaLocation AdditionComputationUnit "ai.unlikely.questionprocessor.computation.Arithmetic$Addition")
(ComputationInputs AdditionComputationUnit InputOne InputTwo) (ComputationDescription AdditionComputationUnit ((Question Unknown1)((Equal (RealNumber Unknown1)(Add (RealNumber InputOne)(RealNumber InputTwo))))))
(ComputationDescription AdditionComputationUnit ((Question Unknown1)((Equal (Add (RealNumber InputOne)(RealNumber InputTwo))(RealNumber Unknown1)))))

In this case there are two passages which describe the computation unit. Description passages have a head node, ComputationDescription, followed by the node for the unit they are describing, and then a passage for the class of UL questions they can help to answer. We also have a passage for the computation unit that describes its inputs, in this case we are saying that the function to compute addition requires two inputs. The description passage uses these inputs to describe where they appear in the question. The final passage we need for the computation unit to work is one that gives the location. In this case, we use ComputationLocalJavaLocation at the head of the passage which means that we are describing a Java class that is locally available to the question processor to use at runtime. With all this information, the system can realise when computation is needed and lookup the best way to get an answer for it and compute it. A preferred example represents many ways to invoke computation units. Each method can be described with a passage similar to this one but with a new head node and a different way to describe the location and way to invoke the computation. For example, if we were to add a computation engine that utilises Lua scripts we could add a passage such as:

(ComputationLuaScript AdditionComputationUnit "a,b=io.read('*n','*n')\nio.write(a+b)")

to help the engine to compute the unit in this way. Another example is the use of an API endpoint and specifying a URL that will return the result with a GET request.

Other examples of computation units are described here to further illustrate the concept:

(IsA GreaterThanOrEqualComputationUnit ComputationUnit)
(ComputationLocalJavaLocation GreaterThanOrEqualComputationUnit "ai.unlikely.questionprocessor.computation.Comparison$GreaterThanOrEqual")
(ComputationInputs GreaterThanOrEqualComputationUnit InputOne InputTwo) (ComputationDescription GreaterThanOrEqualComputationUnit ((Question) ((GreaterThanOrEqual (RealNumber InputOne)(RealNumber InputTwo))))) for greater than or equal comparisons and:
(IsA EqualComputationUnit ComputationUnit)
(ComputationLocalJavaLocation EqualComputationUnit "ai.unlikely.questionprocessor.computation.Comparison$Equal")
(ComputationInputs EqualComputationUnit InputOne InputTwo) (ComputationDescription EqualComputationUnit ((Question)((Equal (RealNumber InputOne)(RealNumber InputTwo)))))
for equality comparisons on real numbers.

Validating that UL is Meaningful/Validation Passages

Just as it is possible to write words in a natural language which have no meaning (such as nonsense verse) it is possible to write syntactically correct UL in a way that is not meaningful. According to various examples it is possible to define clear rules which identify meaningful and non-meaningful UL syntax and for these rules to be applied automatically to determine invalid passages. Note that invalidity is different from truth. A passage can be valid yet still represent something which is untrue.

For example the IsA semantic node that was described earlier requires two additional nodes in order to form a passage where the second node has to represent a class to be meaningful. (IsA Brie GatwickAirport) for example is not meaningful as GatwickAirport is not a class (this passage would translate into English as "Brie is a Gatwick Airport". (IsA Brie Cheese OriginatesFrom) is also not meaningful as IsA is followed by three nodes instead of two.

Validation can be done by any machine-readable description of these constraints which can be read and checked automatically. In a preferred example these are naturally done with other UL passages that describe these constraints called Validation Passages herein. Typically these constraints would be provided by the business, organisation or person that defined the key node in the passage. When validating a passage, examples of the present invention can look at each passage and sub-passage and search for validation passages that apply based on the semantic nodes in these passages. By checking these validation rules against the examined passage a view can be determined as to whether the passage is invalid.

An example of a validation passage on the node IsA is (Validation (IsA Unknown1 Unknown2) (IsA Unknown2 Class)) which says that given a passage in the form (IsA <node1><node2>), (Question)(IsA <node2> Class) should return Yes (or not return No). If it returns No, the passage is invalid. To constrain the number of nodes that can follow a named node a passage like (ValidationCount IsA (Integer "2")) says that IsA nodes must have exactly two semantic nodes following them to be meaningful. Variations of these examples can define further constraints on meaningful passages. In another example, (HasSchema ExpressedInEnglish (Schema ExpressedInEnglish Node String)) is an alternative way of expressing that ExpressedInEnglish passages expect two additional nodes, the first in the class Node (any node) and the second in the class String.

Validation can be used to check or select valid UL that has been generated during statistical methods of translation that may not always generate valid UL (as described herein) and to check UL that has been entered by humans. It can also be used to find contradictions or other logical inconsistencies in passages. For example, using a passage that asserted that another relation had similar or related semantics to IsA might be in conflict with validation passages that described different expectations of the semantic nodes that can be grouped with this relation.

UL Variations

Many variations on the definition of UL are possible for those skilled in the relevant art. Variations can include choice of syntax, choice of representation and selection of many of the other details of the representation and implementation. As used herein and where appropriate 'UL' is intended to cover not only a preferred example described herein but all these similar UL-like representations and variations.

Methods for Answering Questions

In a preferred example the unknowns in the question are identified and the passage making up the body of the question is selected for further analysis. The nodes following the Question node in the head of the question passage are the unknowns that we are trying to find mappings for, such that they satisfy the body of the question. Successfully satisfying the body with UL which is believed to be true is the path to answering the question.

In an example, processing begins on the list of passages from the body of the question and the selected unknowns. The first passage in the list is selected for processing. This processing aims to find all possible mappings for the unknowns that can be true for the passage selected.

In an example, processing a single passage comprises three methods using statically stored UL passages, utilising computation units and utilising UL generated from reasoning:

The first method is to lookup in the passage store if there are any passages that can be directly mapped with the passage being processed. If the passage is exactly the same structure as a passage in the passage store, with all nodes matching other than the unknowns, then the values the unknowns match against are valid results.

The second method is to check if any results can be found by executing computation units. We check if this passage matches against any passages in a computation unit description. All non-unknown nodes in the passage being processed must match the same nodes in the corresponding position in the computation description or align with a computation input unknown. The unknowns being processed must align to output unknowns in the description. The computation unit can then be called to get valid output values for the processed passage's unknowns.

The third method is to see if this passage can be proved by applying any reasoning steps. We look for any reasoning steps where a passage in the second half of the reasoning passage can be unified with the passage being processed. All nodes and structure must be equal between the two passages, other than unknowns in the focus passage or the reasoning passage. If a reasoning passage like this is found it means that this reasoning step could be used to prove the passage being processed. A multi-stage process is used to first find any mappings for unknowns in the processed passage when matching with the reasoning passage. Secondly, mappings for unknowns used in the reasoning passage are found by mapping with the passage being processed. This mapping can then be applied to the front half of the reasoning passage to generate a list of passages that, if they can be matched with known or generated UL and mappings found for them, will prove and find valid mappings for the focus passage. Solutions for this list of passages can then be found recursively using the methods we are currently describing. In some examples we track the reasoning depth currently being processed (i.e. the number of reasoning passages applied) and impose a maximum depth limit to how far we explore for latency reasons.

These three methods may happen in any order and are not dependent on each other.

When a list of valid mappings has been found for the first passage in the list, we must then look at the rest of the list. If the list contains only one passage then the mappings returned are all valid. Otherwise, we look at each solution returned and apply it to the remainder of the list before it is processed. This will return a set of mappings that can then be combined with the mappings given for the head to give a final complete mapping.

Some questions are Yes/No questions and have no unknowns that we are trying to find mappings for. These questions are processed slightly differently. Initially they are processed in the same way in order to see if we have passages, reasoning steps or computation units that can prove the question passage to be true. If this returns a successful result, we can return a Yes result. If no successful result is returned, we look at all passages in the question and negate them using the Not node. Each of these negated passages is then processed to see if we can prove the negative of the original question. If one of these returns a successful result, then a No result can be returned. If none of the initial processing or negated passages processing returns a successful result, that means we cannot show if a question is either true or false. Therefore, we can only return a DontKnow result.

Question Processing Example

To further explain this process, the following is a walk-through of how this method achieves a result for a simple example. For this example, all nicknames used are valid and the relevant UL passages stored are these which exist within a trusted UL store believed to only contain true factual statements:
(IsA X Unknown)
(IsA A Unknown)
(IsA B Unknown)
(IsA Cheddar Cheese)
(IsA Brie Cheese)
(OriginatesFrom Brie France)
(ConsequenceOf (OriginatesFrom X France)(HasAttribute X French))
(ConsequenceOf ((IsA X A)(HasAttribute X B))(IsA X (A B)))
The question is ((Question X)(IsA X (Cheese French)))
This translates to English as "List French cheeses".

X is identified as an unknown which needs a mapping and the passages to process is the list (shown here within square brackets) [(IsA X (Cheese French))]. From now we will show this as [(IsA X (Cheese French))]—X (IsA X (Cheese French))—X is processed. It cannot be matched directly with any passages or match any computation units. However, it might be proved by the reasoning passage (ConsequenceOf ((IsA X A)(HasAttribute X B)) (IsA X (A B))) as it matches with the second half. The mapping is applied and processing continues e.g. recursively.

[(IsA X Cheese), (HasAttribute X French)]—X is processed. The first passage is selected.

(IsA X Cheese)—X is processed. It can be matched with two passages to give the mappings X→Brie, X→Cheddar. No computation units or reasoning passages can be applied.

These mappings are then applied to the rest of the list in turn. This causes the following passages to be processed:
(HasAttribute Brie French)—Only the reasoning passage (ConsequenceOf (OriginatesFrom X France)(HasAttribute X French)) can be applied
(OriginatesFrom Brie France) This completely matches with a trusted passage in the passage store, so we know that this is true. Therefore, (HasAttribute Brie French) is also true.

This combines with the mapping the level above to give X→Brie as a valid result.
Then:
(HasAttribute Cheddar French)—Only the reasoning passage (ConsequenceOf (OriginatesFrom X France) (HasAttribute X French)) can be applied
(OriginatesFrom Cheddar France) This cannot be proved by any means. Therefore, (HasAttribute Cheddar French) cannot be proved.

This therefore results in no result.

The complete process thus gives a single valid mapping of X→Brie, which in turn gives Brie as a final answer.

In various examples, the steps that answer the question are recorded to provide an explanation. The raw output from an example that does this, for this question is here:
Outcome: Yes
Solution: X→Brie
Explanation:
(IsA Brie (Cheese French))
Known: (IsA Brie Cheese)
(HasAttribute Brie French)
Known: (OriginatesFrom Brie France)

The approach outlined above for processing questions may also be used to solve crossword clues, in contrast to conventional AI which is unsuitable for this task. For example, "Creamy French cheese" could be a crossword clue and the approach described above enables the solving of that crossword clue or the definition part of cryptic crossword clues; the clue could generate the answer "Brie".

The approach outlined above is the general process used in some examples for processing questions, however further examples have improvements that can be made to this system for the benefit of reducing latency.

One of these improvements is that an in-memory "dynamic programming" cache can be used to store the resulting mapping of any passage with unknowns that is calculated during the processing of a question. Due to the nature of the question processing, exploring different branches of reasoning can lead to the same passage, and pattern of unknowns, being processed. This cache means that each of these sub questions only needs to be processed once, with subsequent attempts returning the mappings stored in the cache.

A purely recursive approach means that all data fetching from our database systems must happen sequentially just before that data is needed, with all further processing having to wait. To reduce this bottleneck, the system can be modified into two ways. These modifications allows as much data fetching and processing to happen asynchronously and in parallel as possible before a final processing step explores the data and builds the results.

When looking at a passage with unknowns, the three stages outlined above (matching with passages in the store, fetching and execution of computation units and fetching reasoning passages) can be processed in parallel, with data fetching being done asynchronously so that the processing thread is not blocked. The reasoning passage step will then return other passages with unknowns that need to be processed, the results of which can be used to give results for the initial passage. This tree of connection can be stored and the processing of these sub questions that occur from reasoning can happen in parallel, allowing data fetching and exploration of reasoning to be parallelized.

Once all passages are processed up to the given maximum reasoning depth, a second non parallelised step can be used to walk through this tree of processed passages and unknown mappings to find valid answers. When looking at a list of passages, where each passage now has its valid mappings from the passage store and computation, a valid mapping for that list is one where all unknowns have a value and there are no contradicting mappings between passages in the list. This step can recursively look through the data and find all valid mappings for the initial question which can be returned as the answer.

Various examples may selectively store at least some of the passages that have been generated from reasoning or computation making these available in the future for faster processing. The history of these generated passages is also stored in various examples so that changes to the trust in the passages that were used to generate them can be extended to the trust given to these new generated passages.

Priority Queue Example

An alternative example to the recursive system outlined above is to utilise a priority queue to control the order that sub queries are processed in. This alternative uses the same three steps for processing a given query passage but differs in the way that these passages are selected for processing and the way that sub queries are stored. All query passages uncovered during processing are stored with any solutions discovered for that query in a map. This data can then be looked up by the shape of the query passage. The shape of a query passage is defined such that all unknowns are treated as equal, so that the queries (IsA X Cheese) and (IsA Y Cheese) are considered to have the same query shape and be the same sub query.

Alongside this map we also maintain an ordered priority queue of the sub queries left to process. Query passages that we wish to process are first run through our prioritisation method, outlined below, to calculate a priority value for that sub query. They are then placed on the priority queue such that the subqueries with the highest priorities are at the front of the queue. Initially the only query passages added to the map and priority queue are the passage in the body of the incoming question. Processing begins by taking the highest priority query from the queue and processing following the three steps outlined above.

The third step of processing a sub query will output new reasoning steps based on the reasoning passage in the data, which can be used to find solutions for the query. For example, the sub query (IsA X (Cheese Creamy)) and the reasoning passage (ConsequenceOf ((IsA X Y)(HasAttribute X Z))(IsA X (Y Z))) can lead to the reasoning step:

if passages: (IsA X Cheese)(HasAttribute X Creamy)
then passage: (IsA X (Cheese Creamy))

These reasoning steps are stored so that, when combined with the query map the reasoning tree for a question can be explored. The if passages generated from this new reasoning step can then be added to the query map (if not already present) as well as be prioritised and added to the priority queue for processing.

With this example, when new solutions for a sub query are found during processing they are added to the data in the query map. When this occurs we also look at the stored reasoning steps to see if any solutions can be propagated towards the root of the reasoning tree. For example, if we already know that X has the solutions {Brie} for the query (IsA X Cheese), and we discover the solutions X={Brie, MashedPotato} while processing the query (HasAttribute X Creamy) we can look back at the reasoning step above. If we can find a value for X which satisfies both if passages, then we know it is a solution for the then passage. In this example, the solution X=Brie is a solution for both if passages, so it can be added to the solutions for the then passage, (IsA X (Cheese Creamy)), in the query map.

Optimisations

It is possible to place limits on how much work is done processing a question in order to control latency by limiting the number of sub queries that are processed. This can be done as well as or instead of a depth limit.

This example allows for flexible parallelisation of query processing. Rather than processing one query from the queue at a time, the system can use multiple threads to process multiple queries simultaneously. Each thread can independently remove the next query to process from the queue, process it, prioritise any resulting sub queries and insert them into the queue. The thread can then take the next query to process from the queue.

Prioritisation Method:

Multiple methods of query prioritisation are possible, the simplest being to prioritise queries based on their depth within the search tree. The depth value of a query passage increases by one for each reasoning step it is away for the initial question. Using this prioritisation causes the system to follow a breadth first search pattern, processing all queries at a given depth before looking at those the next step down the tree.

Alternative examples can take into account a number of factors including the depth, the reasoning passage used to create the reasoning step, the position of this passage within the reasoning step, and any solutions already discovered for the parent passage or sibling if passages within the reasoning step. This can allow for a "best first" exploration of the search space, with the goal of exploring areas most likely to provide solutions as soon as possible. This is beneficial as it can lead to faster processing of yes/no questions and improved processing ability when constrained by a query processing limit.

With this prioritisation scheme the priorities of queries might change due to solutions found elsewhere in the reasoning tree. Therefore when new solutions are discovered and added to the query map, we must trigger a reprioritisation of all children of the query in question by looking at the reasoning steps uncovered by the "then passage" (the passage that describes the consequence of the reasoning step).

Complex Reasoning Steps:

Some queries can result in sub queries which contain more than one unknown, for example (IsA X Y). These queries can return many solutions, depending on the data, and can result in slow processing times. We call reasoning steps which contain these types of queries complex reasoning steps. To overcome this issue we use an optimisation for complex reasoning steps where initially only the if passages containing one unknown are processed. Any solutions found for this unknown can then be substituted into the complex reasoning step to create simple reasoning steps, with one unknown, which can be processed as normal.

For example, take the query (IsA X Food) and the reasoning passage (ConsequenceOf ((IsA X Y)(IsSubclassOf Y Z))(IsA X Z)).

This results in the complex reasoning step:
if passages: (IsA X Y)(IsSubclassOf Y Food)
then passage: (IsA X Food)

The first passage contains more than one unknown so is not added to the priority queue for processing, however the second if passage can be processed. When this second passage is processed we may find the solutions for X of {Cheese, Nut}. The solutions are substituted into the reasoning step to create new simple reasoning steps. Here we use the result Cheese as an example but this can be done with all solutions for X.

if passages: (IsA X Cheese)
then passage: (IsA X Food)

We can now treat this new reasoning step as normal and prioritise and process the query passage (IsA X Cheese).

Thinking Results

Question answering in various examples has already been described. Some questions can potentially require significant reasoning effort to answer and various examples may choose to limit the amount of reasoning done for specific applications in order to return results within a reasonable time. This can be done, for example, by limiting the number of subqueries performed for a particular question.

When answering questions, the same question may be asked again in the future, and various examples may choose to store the results of queries so that the same question can be answered more quickly next time. Various examples may also extend this approach to subqueries—saving the results to questions that the question processor is asking during reasoning.

In an example, it may be chosen to save these results during responses to user questions or to save them only during an offline process where deep processing of questions can take place without keeping any user waiting and the results stored for use in online queries. These questions can be questions that have previously been seen during online processing or where analysis of logs shows that they are frequently asked. This offline-only approach is the approach taken by a preferred example.

Questions are answered by executing a series of subqueries generated by reasoning that allow us to eventually find passages that answer the question. Certain subqueries appear frequently when processing different questions. Remembering these subqueries and processing them more deeply offline allows us to answer questions more quickly in general, and to return better results (because we've reasoned more deeply about the subqueries, giving us an opportunity to find more solutions). We call the output of this processing thinking results.

In an example, we store two types of information during the thinking results process: the thinking results themselves (i.e. solutions to questions), and metadata about the thinking results which comprises a record that we thought about the question at all and how often the results are used.

Thinking Results Storage

As previously described, question processing uses three methods: direct lookup of passages that can be unified with the current subquery; use of computation units; and reasoning. We store thinking results by storing the intermediate passages that are derived during reasoning, which can then in future be found by direct lookup.

For example, if we ask ((Question X)(IsA X Aerodrome)), we might answer X=Gatwick based on the following reasoning:

(IsA GatwickAirport Aerodrome)
Reasoning passage: (ConsequenceOf ((IsA A B)(IsSubclassOf B C))((IsA A C))) (IsA GatwickAirport Airport)
Reasoning passage: (ConsequenceOf ((IsA A B)(IsSubclassOf B C))((IsA A C)))
Known: (IsA GatwickAirport InternationalAirport)
Known: (IsSubclassOf InternationalAirport Airport)
Known: (IsSubclassOf Airport Aerodrome)

We would store (IsA GatwickAirport Airport) and (IsA GatwickAirport Aerodrome)(both the final answer and the intermediate passage) as though they were normal passages entered by a user or otherwise learned. If we are later asked the same question, the answer can come from a direct look up of (IsA X Aerodrome) without requiring any reasoning. This also works for subqueries: if some other question reasons to the subquery (IsA X Aerodrome) or (IsA X Airport) then we can use thinking results directly rather than further reasoning.

Thinking results, while simply passages like any other, may be stored in their own passage store, separate from other passages, so they can be easily identified and handled—including appropriately expiring.

Along with each new passage stored in thinking results, we may also store the explanation. This is useful in order to preserve the steps used to arrive at the result. Without this, the explanation of X=Gatwick to the above question would simply be Known: (IsA GatwickAirport Aerodrome). Finally, we may also store the dependent passages: these are the passages (reasoning or otherwise) that were used to arrive at the answer. If any of these passages are updated or deleted, we delete the thinking result, as it may no longer be valid.

In examples, we also take care to appropriately store passages for only as long as they can reasonably be expected to be valid. Some passages are only true momentarily—for example the price of an actively traded commodity—or the local time at a particular location; some passages have a far longer half-life of validity, such as a political office-holder, and some passages stay true indefinitely.

Question Answering with Thinking Results

To incorporate the above thinking results into our question answering process we query the thinking results passage store when looking for passages that can be directly unified with the current subquery, as already described above. However, nothing as described currently prevents the system from continuing to reason about the subquery, including potentially reasoning to exactly the same results as the thinking results provide. We may need to know that we've thought about this subquery before, so that we can avoid reasoning about it again. This is why it is preferred to also store metadata about the thinking results.

Metadata

As well as storing a passage such as (IsA GatwickAirport Aerodrome), we also record that we've thought about (IsA X Aerodrome). We check this set of subqueries we've thought about prior to doing any reasoning about them. If we find that we've previously thought about them, we disable reasoning for the subquery, and attempt only direct unification. To speed things up further, we may also record the number of solutions produced by processing the subquery. If this is zero, we can avoid searching for passages that unify with the current subquery: we know there are none.

Offline Process

In a preferred example, an offline process runs questions using a very high reasoning effort and stores the resulting thinking results in the manner already described. The metadata is stored in a distributed in-memory cache; we store that the question has been processed, along with when, and the number of solutions generated. Subqueries generated while reasoning are also added to the distributed cache.

The offline process may run continuously, choosing questions to process based on their hit count (see below) and how long ago we last processed that question. Questions with low hit counts that were processed some time ago are removed from the cache—or where there is evidence that the results may have expired.

Online Question Answering

Before answering a top level question outside of the offline process (i.e. a question that must be answered quickly), a preferred example consults the distributed cache to see if the question has been processed with thinking results, and processed recently enough. If so, we process the question with no reasoning (i.e. we use the thinking results). If the cache tells us the question led to no thinking results, we return immediately, without querying for the thinking results. In this case, we return almost instantly with high quality results.

If thinking results are not available (either we've not processed the question before, or we did so too long ago) we proceed as normal (i.e. with reasoning until we hit the reasoning effort threshold or terminate for some other reason). We continue to consult the cache for subqueries and do no reasoning for any subqueries that are in the cache (and entirely avoid database lookups if the cache tells us there are no results). We don't adjust our reasoning budget in any way if we find such cache hits for subqueries. In this case, thinking results do not improve performance, but they may improve result quality significantly (if there are thinking results for subqueries).

Whenever we consult the cache, we record a hit on that query. If the query doesn't exist yet in the cache, we add it with a hit count of 1.

Various examples may choose to periodically remove thinking results which are insufficiently or infrequently used or never used, even if still considered valid, for space reasons.

According to various examples including a preferred example the metadata may include all the stored passages including reasoning passages that were used to generate the result. In examples where passages may subsequently be discovered to be untrue, invalid, or to have changed, this metadata enables thinking results that rely on this invalid passage to be immediately removed. If a thinking result uses another thinking result to generate a result, then the dependent passages for the used thinking result are included in the dependencies of the new thinking result.

Auto-Curation

Various examples may utilise a process of automated curation to determine the value of passages stored in a passage store. The benefit of this technique is to scalably maintain a vast amount of information represented in UL without the need or with less of a need for human curation. The value of a passage determined with this process is then used by the reasoning engine in the question processor to determine whether or not it should use the passage. This enables passages to be sourced from low-quality or unknown quality sources knowing that bad passages will eventually be switched off or no longer used. Put differently, it enables the system to learn which of its stored passages are useful, true or otherwise valuable and which are not.

When a new passage is added to the store by a person it is assigned a low initial trust value when added by a normal user. A privileged user or a user that the system has learned to trust may result in a higher starting value. The reasoning engine can then be instructed to be more experimental when processing questions which means that it can try to use less valued passages to answer the question. The answers provided by an experimental reasoning engine are then monitored for any signals that would indicate whether the low-value passage had a positive or negative effect on the answers. This information then feeds back into the auto-curation process which reevaluates the value of the passage with the new signal.

Examples of signals used include the results of test questions with known good answers: passages which support or are compatible with these when used produce a positive signal for that passage, while those that result in wrong results or which substantially slow the production of good results result in a negative signal. Signals can also come from real-world results. Information from a user that the system has produced something valuable will send a positive signal to all passages of all kinds that were used to generate that result. Similarly feedback that the result is bad will taint all the used passages. Some good passages may be tainted unfairly but over time they will also receive positive signal and it will be possible to determine constituent passages that are consistently the source of negative results.

Value Vector

According to various examples, the overall value of a passage is a combination of factors that can change depending on the system or process that wants to use it and the context. For this reason, passages may be assigned a vector of values where each number represents a different quality of the passage. This allows us to have a different dimension for veracity, usefulness, and efficiency. Then the process that uses the passages just has to utilise a priorities vector with numbers at each index that indicate how much they prioritise that value and the overall value of the passage to that process can then be obtained from the dot product of the two vectors.

However, it is sometimes useful to use the values individually in certain contexts, where knowledge of that score's applicability to that context can be used to optimise our use of the passage. For example, allocating reasoning budget in the question processor can be based primarily on the efficiency score.

Offline Processing and Experimentation

A further method for auto-curation is to run a continuous process that reprocesses questions it has seen in production with a higher experimentation level to test whether any low-value passages might have been helpful for finding more answers. Any low-value passages that do help provide further answers can then be boosted with a positive signal. According to other examples, an offline process can run test questions with known answers using the passage being tested and see if it causes wrong or extraneous answers to be found or to otherwise have an unacceptable impact on the performance of the system (such as poorer latency). This can be used to verify passages containing information and can be used for passages such as reasoning passages. Passages determined to be detrimental from this test process can be ignored for production use.

Learning

Examples of the present invention including examples implementing any of the applications described herein or other applications can learn, representing what they have learned in UL (or similar) and then utilising that stored UL to improve their performance. The learned passages are stored in long or short-term memory and utilised in delivering the application.

This approach contrasts with what is commonly referred to as machine-learning in the prior art where what is learned are parameters or weights which allow a model to perform statistically better at a classifications, regressions or other tasks. Examples can also combine the language-based learning described herein with statistical machine-learning.

The learning described herein are not weights but concepts and ideas expressed in language and translatable into natural language enabling examples of the present invention to reason with what they have learned and explain what they have learned to human users. The learning also enables conversation in text or spoken language with users in a way that weights in a statistical model do not.

Sources/methods for learning in examples of the present invention include:
 (a) learning from conversation or other natural language provided by users: by translating natural language provided by users in spoken or written form into UL and storing it, the concepts, ideas and knowledge represented in the stored UL is learned and can be utilised.
 (b) learning from reasoning: UL that is generated from a chain of reasoning, can be stored and utilised. The reasoning may be directed to a particular goal such as answering a question or the result of undirected thinking designed to find ideas that may be useful.
 (c) learning from other natural language. By translating all or parts of documents such as web pages, scientific papers or other articles into UL, the resulting UL can be utilised by applications as described herein. Other sources of natural language can include audio recordings or videos containing human speech where speech recognition technology is first utilised to create a text transcription of the recordings of voice which are then translated into UL. In some examples a neural network may be trained end-to-end to turn audio data directly into UL. For video, examples may combine knowledge of what is shown in the video, for example as described by a machine-learning model designed to analyse the content of the video with the simultaneous audio to better translate the audio or to augment the audio with additional information which is recorded in the learned UL.

(d) learning from structured data. Structured data such as the content of a table found in a document or on the web, a spreadsheet or the contents of a relational, graph or other database. Structured data also includes formats such as JSON which may be the output of automated systems. Structured data can be turned into UL by assigning semantic nodes to the identifiers in the structured data or relations corresponding to the relations in a relational database and generating UL that corresponds to the meaning of the structured data.

(e) learning from analysis of other data. Examples of the present invention may analyse data, processing the data with an algorithm and express the results of that analysis in UL. By storing the resulting UL the analysis and derived data is available to the system in a form that can be processed and reasoned with as described herein. In some examples the analysis can be done with a machine-learning model.

Distributed Use. Semantic Node Resolution.

As previously described a preferred example enables any user of UL to use any new ID for any node—essentially a private ID. However, if that entity is being used elsewhere it may make sense for that user to use a shared ID for the node.

To enable this to happen, a service of a preferred example is providing a shared ID to a node from a description of the node. This is referred to herein as Semantic Node Resolution (SNR).

To enable this service it requires information about the existing semantic nodes that the service may return represented in UL. For shared nodes this information will typically be public but may also be based on additional private information about the node. When the SNR service is called, the caller provides a description, giving information about the entity for which a semantic node is requested. In various examples, this caller's description might be in UL or it might be a natural language description—or a combination of the two.

The SNR service then compares the known information about the described entity with the description it has about existing nodes to see whether it can confidently match the new node with a known node and thus provide a shared ID.

To do this the SNR considers potential matches and then tries to estimate the probability that these are two different nodes. Beyond a certain threshold probability, e.g. 0.999, the shared node is provided. In various examples, possible matches might be returned with their probabilities enabling the caller to decide for themselves whether to use the shared ID or a new one.

The probability calculation is used by combining probabilities from various parts of the description.

For example, supposing the unknown node is a human being, with first name "William" and last name "MacDonald" and with a date of birth 1953-04-02 and country of birth Ireland. With just a date of birth matching, the resolution could not happen as many tens of thousands of people share the same date of birth but combining it with a shared country of birth and shared name the probability that they are the same node becomes very high and using the shared ID becomes reasonable. The implementation of this for humans would include heuristics and data to estimate the probability of any human having a particular date of birth or a particular name, combining those probabilities and then comparing that with the universe of possible entities in that class. These calculations can be used to estimate a probability of the match being unique.

Note that some probabilities can be considered independent and multiplied while others are not independent so need to be combined with caution. For example, being female halves the possibilities as there are approximately equal numbers of men and women. The name Jane reduces the possibilities significantly as only a small percentage of people are called Jane but knowing that the node has first name Jane and is female gives very little extra information over just first name Jane as almost all people with first name Jane consider themselves female. There are more subtle non-interdependencies too. Name probabilities vary considerably with country of birth for example.

The immediate use of SNR is providing a shared ID which can then be confidently used by the calling user. In some cases, the level of confidence may not be sufficient to immediately use the shared ID and the caller may instead prefer to use a new or private ID until more information is known in order to make a match. SNR can also be used after a passage has been written with one or more private IDs with the goal of a subsequent step where the passage is rewritten replacing one or more private IDs with public IDs. It can be similarly used to merge public ids which denote the same entity. Identifying them as being the same might not have been possible when they were first used.

Multiple UL Stores

Examples of the current invention enable passages to be stored in multiple separate stores. Stores can be used for different purposes and can have different access controls. Different stores could also have different trust levels. For example, various examples could maintain access to a UL store that contains highly trusted passages that represent common sense information about many of the widely used semantic nodes and with reasoning passages that are useful and not disputed. Another UL store may contain employee and human resource records of a private enterprise and have access heavily restricted to selected people within that private organisation. In some examples, the restrictions may apply to organisations. A UL representation of a particular natural language book may be given its own store.

According to various examples, UL stores can be shared between multiple users. For example, a trusted core UL store of widely used semantic relations could be made widely available. UL representations of books or key stores of knowledge could be commercially licensed by organisations that build and maintain them.

Translation

Translation is the act of turning UL into natural language and from UL into natural language for the purpose of communicating with humans, learning, making sense of information stored in natural language among other purposes.

Neural Machine Translation

Neural machine translation is the term for prior art methods used for using neural networks to translate between pairs (or more) of natural languages. A typical architecture includes an encoder which turns a source sentence into an internal vector or sequence of vectors that encodes the source sentence which is then read by a decoder which generates a corresponding sequence of words in the target language. Variants of the architecture use recurrent neural networks including Long Short-Term Memories (LSTMs), various attention mechanisms and most recently Transformers. Such architectures can be considered conditional language models where output of the language mode is conditioned by the source language which is input.

Examples of the present invention utilise neural machine translation architectures, but instead of using only natural languages they utilise neural networks that have been trained with translations between a natural language and UL (or similar). The resulting neural network can then generate UL which corresponds to the meaning of the input natural language. In a preferred example the vocabulary includes semantic nodes and the left and right parenthesis symbol.

An important point is that in contrast to a neural translation system translating between natural languages, a neural architecture designed to translate between a natural language and UL can be considered to be a system to understand natural language as the resulting UL (or UL similar) representation fully represents the semantics of the source natural language and is machine-processable. This UL can then be used for reasoning, question answering and other actions and applications as described herein. In machine translation systems between natural languages both the source and target translations exhibit all the issues with machine understanding that exist with all natural languages and which have been previously described herein.

Beam searching is a method where instead of just reading off the most probable output symbol from the decoder in a neural machine translation system at each step, a range of possible outputs from the decoder is maintained along with their probabilities which can be used to generate a list of probable translations. Examples of the present invention capable of validating UL use beam searching and remove invalid UL translations from the results ensuring that the generated UL is meaningful. Automatic validation of UL may also be used to ensure that the system is only trained with valid UL. According to various examples automatic validation can be done with Validation Passages (as described herein).

Other Translation Methods/Alternative Examples

One method for translation to and from UL as used in some examples is done by looking at UL passages which have been marked as "Ground truth translations". These are known translations between a UL passage and a passage written in a natural language such as English which are assumed to be accurate. In some examples these may simply be stored in a database listing the ground truth translations against the corresponding UL passages. In some examples translations may themselves be stored as UL such as this:

(EnglishGroundTruthTranslation (IsA Brie ((Cheese French) Creamy)) "Brie is a creamy French cheese")

Which says that 'Brie is a creamy French cheese' is an accurate English translation of (IsA Brie ((Cheese French) Creamy)). If we were to call this passage GroundTruthTranslation1 and we had (IsA GroundTruthTranslation1 GroundTruthTranslation) in the store as well, then we could use this known 'correct' translation as a basis for other similar translations. Using the above, perfect translations can be generated whenever there is an exact match such as "Brie is a creamy French cheese" into and out of UL. These passages can also be used to translate things that are not an exact match. A simple example of a non-exact match might be the English passage "Camembert is a creamy French cheese."

The method used in some examples depends on which direction we need to translate. When translating from natural language into UL, we break down the structure of the given sentence and compare it to the structure of each of the known ground truth translations to sort by similarity. The sentences are split into words (or other atomic parts of the language) and then re-merged into subparts (sequences of words) that we have an existing translation for such as (ExpressedInEnglish Camembert "Camembert") and (ExpressedInEnglish IsA "is a"). These two passages would mean that the Camembert node becomes an option for the "Camembert" part of the sentence and IsA becomes an option for the "is a" part. When "Camembert is a creamy French cheese" is matched against GroundTruthTranslation1, the translator will give a high similarity score because most of the sentence is the same and the only part that is different ("Camembert") has the same part of speech as "Brie" and has an option (Camembert) in the list which is very "similar" to the node used in GroundTruthTranslation1 which was Brie. In a preferred example, the similarity of these two nodes is compared using a component of the UL platform called the entity resolver.

According to various examples, the entity resolver currently works by comparing large numbers of passages that the two nodes are used in and determining how similarly they are used. If they are used in almost similar ways then they are more likely to be very similar nodes for which a straight substitution in a translation is likely to be accurate. For example, they may belong to the same class so we may see (IsA Brie Cheese) and (IsA Camembert Cheese), which are both identical other than the nodes we are comparing. In other examples, the entity resolver combines further heuristics or properties in order to determine the similarity of two given nodes.

Translating from UL to English makes use of the entity resolver component again to compare the UL we are translating against the known ground truth translations and to pick the most similar one. The nodes that are different then have their translations replaced to form the final output string.

Word embeddings such as word2vec or GloVe is a technique known by those skilled in the relevant art in which large volumes of text are analysed to determine words that have similar meaning and usage. Various examples make use of this technique to determine the similarity of the natural language words and their suitability for substitution in a known ground truth translation. For example, an analysis of English would determine that Camembert and Brie were very similar items as their word embeddings would be very near each other. This means a ground truth translation including Brie would almost certainly stand with the word Brie substituted for Camembert as well as an exchange of the semantic nodes in the UL half of the translation.

Another technique used by various examples involves automatically assessing the semantic impact of changes in natural language wording. In natural language there is often many ways to say the same thing. Sometimes rephrasings result in another passage with identical meaning, on other occasions, the change in semantics is small. In other cases, it is large. With an automatic method of assessing semantic impact between two natural language passages, ground truth translations can be used when the assessment is that the semantic impact is small or non-existent, even if there is not an exact match with the natural language in the ground truth translation.

Examples of techniques that can be used by the semantic impact assessment would be noticing the substitution of words known to be synonyms or words of similar meaning, rephrasings that are known to be other ways of expressing the same thing (e.g. talking in English about "<noun1> of <noun2>" and "<noun2>'s<noun1>"), and the addition of filler words that only subtly change the meaning when they are used.

According to various examples, the translator in each direction uses a pipeline where each pipe is a function that takes in a document structure and returns a new document structure. Each pipe can add components to the document for use by later pipes. The final document contains a component that the pipeline considers an output component and the pipeline returns this as the output. The first pipe in each pipeline is for a direct lookup in the cache, if this returns a successful translation then the rest of the pipes can be skipped. In the case of English to UL, we then run a series of pipes that make use of StanfordCoreNLP libraries or similar to tokenize the sentence, and to tag it with part of speech information that can be used to help the ground truth translator pipe determine the best match in a later pipe. When translating from UL to English, the only pipe used before ground truth translations is the direct lookup pipe since the UL itself should already give enough semantic information to be translated back into natural language.

An optimisation present in various examples is to use a Bloom filter to identify language passages which are not present in the store of translations, in order to reduce the load to the system. A Bloom filter is a space-efficient probabilistic data structure, that is used to test whether an element is a member of a set.

According to various examples the translator would actively try to vary the translations to natural language between a wide range of semantically equivalent and natural translations to create varied and fresh speech for the benefit of the users of the products powered by the present invention. For ground truth translations this can be done by selecting randomly between multiple translations for the same UL. The other techniques described herein either also naturally produce multiple candidate translations or can be easily adapted to do so.

Translation Context

UL can encode self-referential and meta-linguistic statements: it is possible to describe in UL how and when to translate, and what is more appropriate in one context than another. For some applications it is desirable to have the ability to generate translations applicable specifically in the present context. Some examples utilise a method to express in UL descriptive, contextual information about the semantic nodes which are likely to be translated. By having this information present and available to the system at runtime, programmatic reasoning is able to select the most appropriate attribute from those available (e.g. "vehicle", "car", "my Audi") which can then be substituted for the original node in a preprocessing step. Other translation techniques can then be applied to render this in natural language.

Translation Between Natural Languages

A goal of UL is to fully represent the meaning of any natural language and the language is easily extendible to accommodate nuance and new concepts that come from new languages which may not have been created before. This means that that once a document or piece of natural language has been translated into UL nothing has been lost and the UL translation can contain all the semantics and nuance of the original. This contrasts with a single natural language which is naturally an imprecise translation of the source language with words which do not quite mean the same or even words which do not exist in the target language.

For this reason, an improved method for translating between many languages is to build a translator from and to UL for each natural language and translate between natural languages by first translating the source language into UL and then translate from UL into the destination language.

Prior art translation systems such as neural machine translation systems typically learn from examples of text between pairs of natural languages—or have effort and resource directed to specific language pairs. That means that with n languages you would need of the order of n squared translation systems in order to accommodate all language pairs. With UL being an effective intermediate language the number of systems you would need to build would be 2n—a UL→NL and a NL→UL system for each language.

Representation of Emotion, Connotation Etc.

Words in natural language often have connotations or inferences that augment or are in addition to their pure semantics. For example, in English there are multiple synonyms for the word "error" such as "boo-boo", "screw-up", "inaccuracy", "blunder" etc. Although considered synonyms, these different words have different connotations and usages. For example, the word "boo-boo" is used for children or to mock an adult; the word "inaccuracy" expresses politeness or a relatively minor error; a "blunder" implies a large error where there is considerable blame on the person making it.

According to various examples these connotations and usages can be represented by having a different semantic node corresponding to each of these concepts. The meaning that includes these connotations can be represented in other UL that ties these semantic nodes to similar but different ones whilst also explaining the differences.

The use of nesting can be used to represent emotion and tone in writing as well as other properties such as nuance or level of formality. For example, semantic nodes representing an angry tone of voice can be combined with the passage being spoken to represent that passage communicated in an angry tone of voice. In examples with voice, representations like this can be used to modify the generated sound to include emotion appropriately in the output.

Specific Applications Built on Examples of the Present Invention

Recruitment Application

An automatic recruitment application is one that tries to find highly qualified candidates for a given position automatically: matching a representation of the potential applicant's résumé with a representation of the role and job specification. Further examples of such an application may also match an applicant's desired role with the job description as well as assessing how well the applicant is qualified.

There may be hundreds of thousands of possible candidates online who may be a match for a given job. Recruitment prior to the present invention is typically done by humans using tools to search a database of such candidates. Typically, such searches are either done purely on unstructured data—searching for keywords in their résumés, sometimes combined with limited structured data. For example, a job application specialising in finding software engineering talent may include structured data for common programming languages and the search box, in addition to allowing searches for keyboard, may also include drop-downs or check boxes for these specific skills. This limited structured data is created in the conventional way with a database schema and specific code to include this data in the search.

Additionally, some applications attempt to apply state-of-the-art NLP techniques to both the résumé and the job specification and then attempt to rank the applications by how good a statistical match they are to the specification. The limitations of state-of-the-art of NLP will mean that the ranking is only approximate and heavily influenced by similar keywords in both the résumé and job specification. It will provide some value to a recruiter who wants to narrow down the list of résumés but substantial human involvement will still be needed to have high confidence in a good match and the recruiter may fail to see a good match as a result.

In reality the number of different skills or experiences that might appear in a résumé or job specification is very large, meaning that any structured data decided upon and programmed into the system can only cover a small fraction of what might be searched for.

Automatic recruitment is thus an example of a HUB application.

An example application called Jobe is described herein. It represents a preferred example and other relevant examples of a recruitment application.

In a preferred example a large part of the job specification and candidate's résumé is represented in UL or similar and the reasoning methods described herein are used to determine whether they match. In various examples a UL or similar representation of at least some of the candidate's objectives is also matched with the job specification and possibly a description of the employer.

FIG. 1 shows an example of a push notification on a mobile phone from Jobe notifying the user of a new candidate who is a perfect match for one of their jobs. This match happened automatically. Had the match been statistical or using existing inexact methods, the application designer would not have had the confidence to interrupt the user with this message as the match would be far too frequently poor. Because the technology in this application is based on an example of the present invention, the automatic match is known with very high confidence to be good and so interrupting the user is a good product experience. The present invention, in an example, thus enables a product experience that was hitherto not possible.

Figure 2:
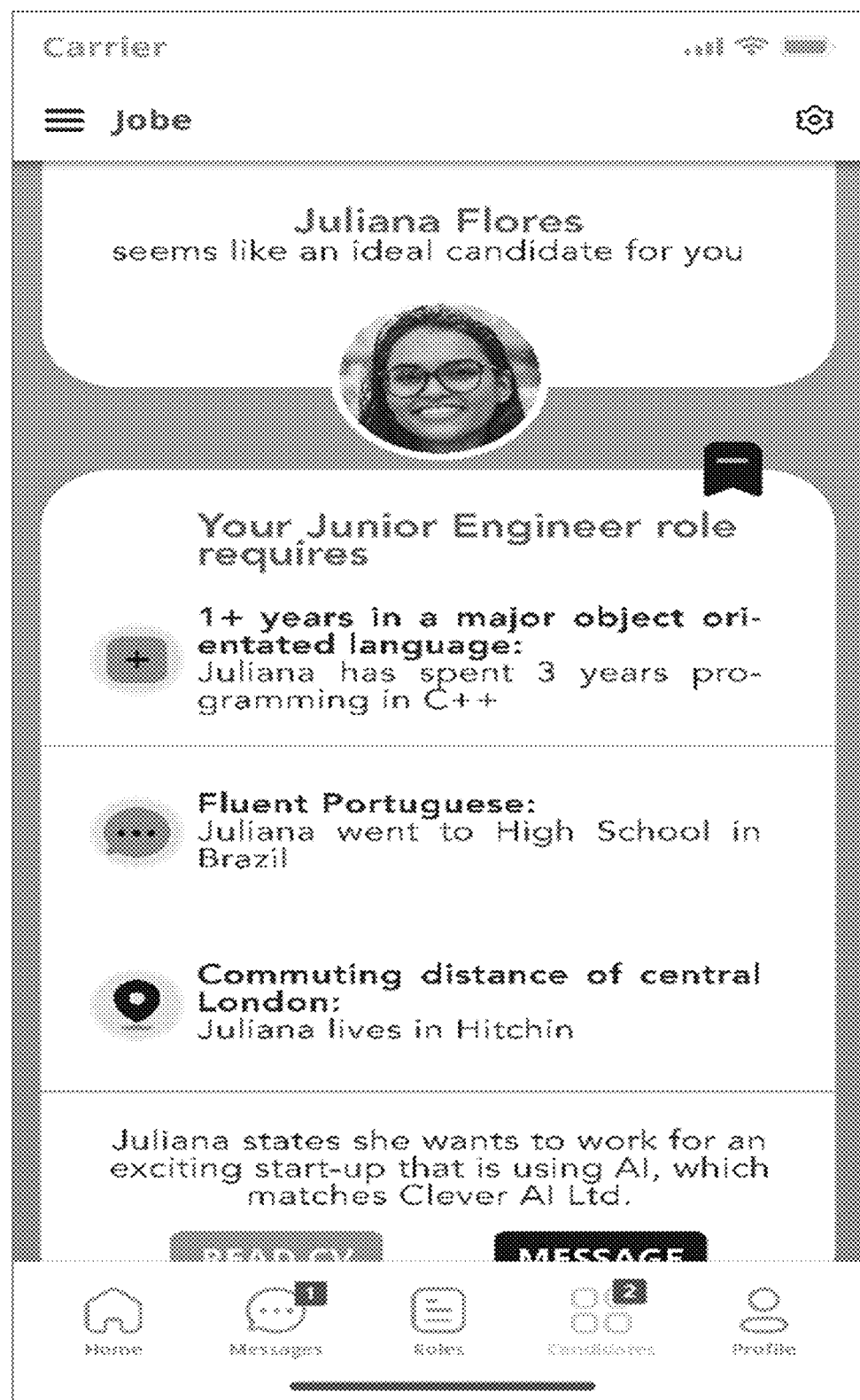
FIG. 2 shows example screen output for a description of a job match.

FIG. 2 shows an example of the details of the match, where requirements for the role are justified with data from the candidate's résumé. FIG. 2 illustrates three example job requirements for a junior software engineer position: experience with a major object oriented language, fluency in a foreign language and their location. Specifically Jobe has matched the requirement "1+ years in a major object oriented language" with "3 years programming in C++"; inferred fluency in Portuguese from the fact the candidate attended high school in Brazil where the predominant language is Portuguese and that the candidate is "within commuting distance of London" by the fact that she lives in Hitchin, Hertfordshire, UK.

In these examples, none of the evidence from the résumé that they match shares any keywords with the actual requirement. All three matches also require reasoning with the UL representation and come from the semantics of the requirement and the job specification.

To further illustrate here is how one of these matches is done using UL:

As described herein examples of the present invention can answer Yes/No questions. In order to match a similar candidate, the system has asked itself the question "Does 7 years' experience of C++ imply at least five years' experience of programming a major object-oriented language?"

"7 years' experience of C++" can be represented in UL as ((Experience CPlusPlus)(Year (RealNumber "7")))—Experience combines with another semantic node to represent experience with that concept. Year represents the unit of time and combined with number gives a number of years of time.

"at least five years' experience of programming a major object-oriented language" can be represented as ((Experience (Programming (UnspecifiedMember((ProgrammingLanguage ObjectOriented) Major))))(Year (AtLeast (RealNumber "5"))))

AtLeast in combination with a number gives a number range. Thus, in combination with a unit gives a unit range. In this case a minimum number of years. UnspecifiedMember represents a member of a class which isn't identified.

Therefore, the whole question can be represented in UL as follows:
 ((Question)(Implies ((Experience CPlusPlus)(Year(RealNumber "7")))((Experience (Programming(UnspecifiedMember((ProgrammingLanguage ObjectOriented) Major))))(Year (AtLeast(RealNumber "5"))))))

To answer this question, the following trusted passages are utilised from a UL store that represents recruitment related information. According to various examples, these passages have been generated from conversation between the system and people, translating the natural language into UL or added directly by trusted people, building the recruitment application.
 (IsA ProgrammingLanguage Class)
 (IsA ObjectOriented Attribute)
 (IsA Major Attribute)
 (IsA CPlusPlus ProgrammingLanguage)
 (IsA CPlusPlus ((ProgrammingLanguage ObjectOriented) Major))
 (IsA Year Unit)

As well as these known passages, a computation unit and reasoning passages are required. The computation unit, used for comparing if 7 is greater than or equal to 5, is defined as follows:
 (ComputationInputs GreaterThanOrEqualComputationUnit InputOne InputTwo) (ComputationDescription GreaterThanOrEqualComputationUnit((Question) ((GreaterThanOrEqual(RealNumber InputOne)(RealNumber InputTwo))))
 (ComputationLocalJavaLocation GreaterThanOrEqualComputationUnit "ai.unlikely.questionprocessor.computation.Comparison$GreaterThanOrEqual")

And the needed reasoning passages used for this question are:
 Core reasoning passages that help define the IsSubclassOf relation
 (ConsequenceOf (IsSubclassOf A B)(IsA(UnspecifiedMember A)B))
 (ConsequenceOf ((IsSubclassOf X Y)(IsA A Attribute)) (IsSubclassOf (X A) Y))
 (ConsequenceOf (IsA X Class)(IsSubclassOf X X))
 Reasoning to do with quantities, activities, implication etc.:
 (ConsequenceOf ((Implies X Y)(QuantityWithinRange A B))(Implies (X A)(Y B)))
 (ConsequenceOf ((IsA X ProgrammingLanguage)(Implies (Experience (Programming X)) Z)) (Implies (Experience X) Z))
 (ConsequenceOf ((IsA X Activity)(IsA Y Activity)(Implies X Y))(Implies (Experience X) (Experience Y)))

Programming a programming language is an activity
  (ConsequenceOf (IsA X ProgrammingLanguage)(IsA
    (Programming X) Activity))
If X is a programming language and a member of the class
C, programming X implies programming a member of C
  (ConsequenceOf ((IsA X ProgrammingLanguage)(IsA X
    C))(Implies (Programming X) (Programming (Un-
    specifiedMember C))))
If A is within the range B and X is any unit, then A of X
is in the range B of X
  (ConsequenceOf ((IsA X Unit)(WithinRange A B))(Quan-
    tityWithinRange (X A)(X B))) If X is greater than Y
    then X is within the range at least y
  (ConsequenceOf (GreaterThanOrEqual X Y)(Within-
    Range X (AtLeast Y)))
Using the question answering methods described herein,
a Yes result can be generated to the question.

To further illustrate the method, the following explanation showing the steps that may be generated by some examples utilizing the reasoning method described herein:

dietary advice and unlock interactions which have not been previously observed. Nutrition is thus a HUB application.

Health more generally is also an example of an unreasonably broad domain. Nutrition is a sub-domain of this extremely broad domain. An application that tracks a person's day to day health information would need to combine numerous health tests and include domains such as levels of certain substances in blood, measurements of organs, measurements of body composition, measurements of the performance of the body in various domains, activity information, nutrition information, genetic data, microbiome data, sleep data, specific events that influence health (workouts, consumption, drinking of substances, moods, bowel motions) as well as numerous documented health conditions and diseases. Any one of these types of data can be relevant to others as well as to the patient's health goals. Although small subsets of these can be built with the typical local schema effort that we see today, building a huge generic health application that can potentially encompass all of this information was not practical prior to the current invention.

```
(Implies ((Experience CPlusPlus) (Year (RealNumber "7"))) ((Experience (Programming
(UnspecifiedMember ((ProgrammingLanguage ObjectOriented) Major)))) (Year (AtLeast
(RealNumber "5")))))
   (Implies (Experience CPlusPlus) (Experience (Programming (UnspecifiedMember
((ProgrammingLanguage ObjectOriented) Major)))))
      Known: (IsA CPlusPlus ProgrammingLanguage)
      (Implies (Experience (Programming CPlusPlus)) (Experience (Programming
(UnspecifiedMember ((ProgrammingLanguage ObjectOriented) Major)))))
         (IsA (Programming CPlusPlus) Activity)
            Known: (IsA CPlusPlus ProgrammingLanguage)
         (IsA (Programming (UnspecifiedMember ((ProgrammingLanguage ObjectOriented) Major)))
Activity)
         (IsA (UnspecifiedMember ((ProgrammingLanguage ObjectOriented) Major))
ProgrammingLanguage)
            (IsSubclassOf ((ProgrammingLanguage ObjectOriented) Major) ProgrammingLanguage)
               (IsSubclassOf (ProgrammingLanguage ObjectOriented) ProgrammingLanguage)
                  (IsSubclassOf ProgrammingLanguage ProgrammingLanguage)
                     Known: (IsA ProgrammingLanguage Class)
                  Known: (IsA ObjectOriented Attribute)
               Known: (IsA Major Attribute)
         (Implies (Programming CPlusPlus) (Programming (UnspecifiedMember
((ProgrammingLanguage ObjectOriented) Major))))
            Known: (IsA CPlusPlus ProgrammingLanguage)
            Known: (IsA CPlusPlus ((ProgrammingLanguage ObjectOriented) Major))
   (QuantityWithinRange (Year (RealNumber "7")) (Year (AtLeast (RealNumber "5"))))
      Known: (IsA Year Unit)
      (WithinRange (RealNumber "7") (AtLeast (RealNumber "5")))
         Computed: (GreaterThanOrEqual (RealNumber "7") (RealNumber "5"))
```

Various examples may generate a natural language translation of these steps, either a full one showing every step or with obvious common-sense steps skipped to create a simplified explanation that is easier to understand. Examples of such an explanation generated by various examples are shown in FIG. 7.

Horizontal Health Application

A horizontal health application is an application which attempts to record and manage an extremely diverse set of health data from one or more users. As discussed herein, representing this data in a way that can be understood and managed by a computer system is impractical using the state-of-the-art prior to the current invention.

Nutrition: there are millions of different foods and millions of different consumable substances. These substances are sometimes related (e.g. types of fat) and they have numerous different attributes. The interaction of these substances together and with the human body is highly complex—and a deep semantic representation of nutrition could allow computer-based systems to give very sophisticated "Chea" is an example application from this class of applications described herein. It represents a preferred example and other examples of the present invention.

In addition to recording health data from wearables and other health sensors, Chea has a chat window where a user can communicate health related events as they happen and have them understood, stored and processed by the application. Example health events could be nutritional events: consuming food and drink. This window can also be used optionally to record other health events: specific symptoms of illnesses, information about mood and energy levels, bowel motions characterised on the Bristol stool chart etc.

Figure 3:
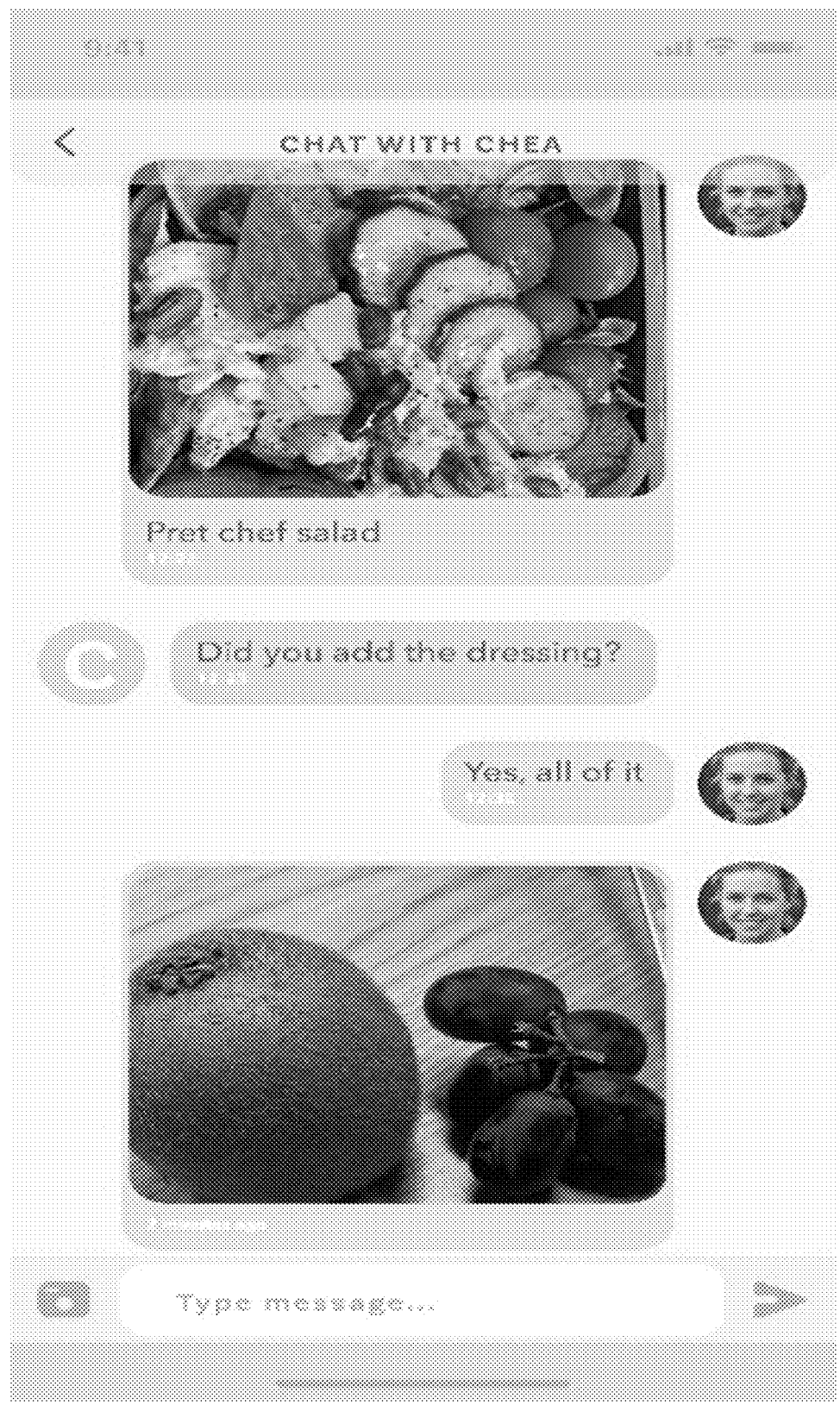
FIG. 3 shows an example conversation within an app where nutritional data is being communicated with the app.

FIG. 3 shows a conversation within the app where nutritional data is being communicated with the app. In a preferred example conversation is between the user, the AI, any number of human medical professionals and human nutritionists who derive semantic nutritional data from photos and descriptions of food and drink entered by the user when they are consumed. The AI can handle what is possible with humans picking up other tasks where automatic processing is not possible. An example of an automatic task would be prompting a user when nutritional information or other supposedly regularly supplied health information has not been added for a period. For example, if a long period of the day went by without any food or drink being entered the AI could ask the user whether this had actually happened or whether they had forgotten. If the user was intending to log details of bowel motions they could also be prompted if an unusually large gap appeared with no information being shared. The semantic nutritional data not only represents exactly what was consumed and when but also represents uncertainty—e.g. from not knowing the exact composition of the food, to uncertainty about the portion size from the images.

UL supports this uncertainty. For example, it may not be possible to determine what kind of cheese is being shown in an image and the user may also not know but the semantic node for cheese can be used in that circumstance. If a more precise type of cheese is in the recipe such as Cheddar or even a very specific type of cheddar, then the appropriate semantic node can be used for that. Passages in a trusted store represent the relationship between Cheese and specific types of cheese as well as much pertinent information about these nodes.

UL can represent information about the likely constituent substances of foodstuffs too. For example, if the image was of a portion of chicken pie, UL can represent the composition of chicken pie including both the pie crust and the typical ingredients of the pie portion. Uncertainties in exactly what those ingredients are and the variations in volume can also be represented in UL. That combined with the uncertainty in the portion shown, as communicated by the nutritionist can be combined to include a detailed semantic breakdown of that meal with uncertainties and that can be recorded. As this nutritional data is fully semantic and the application also has relationships and other information about these substances represented in UL, the data can be looked at in many different ways and measured and charted through many different lenses to derive health insights.

Figure 4:
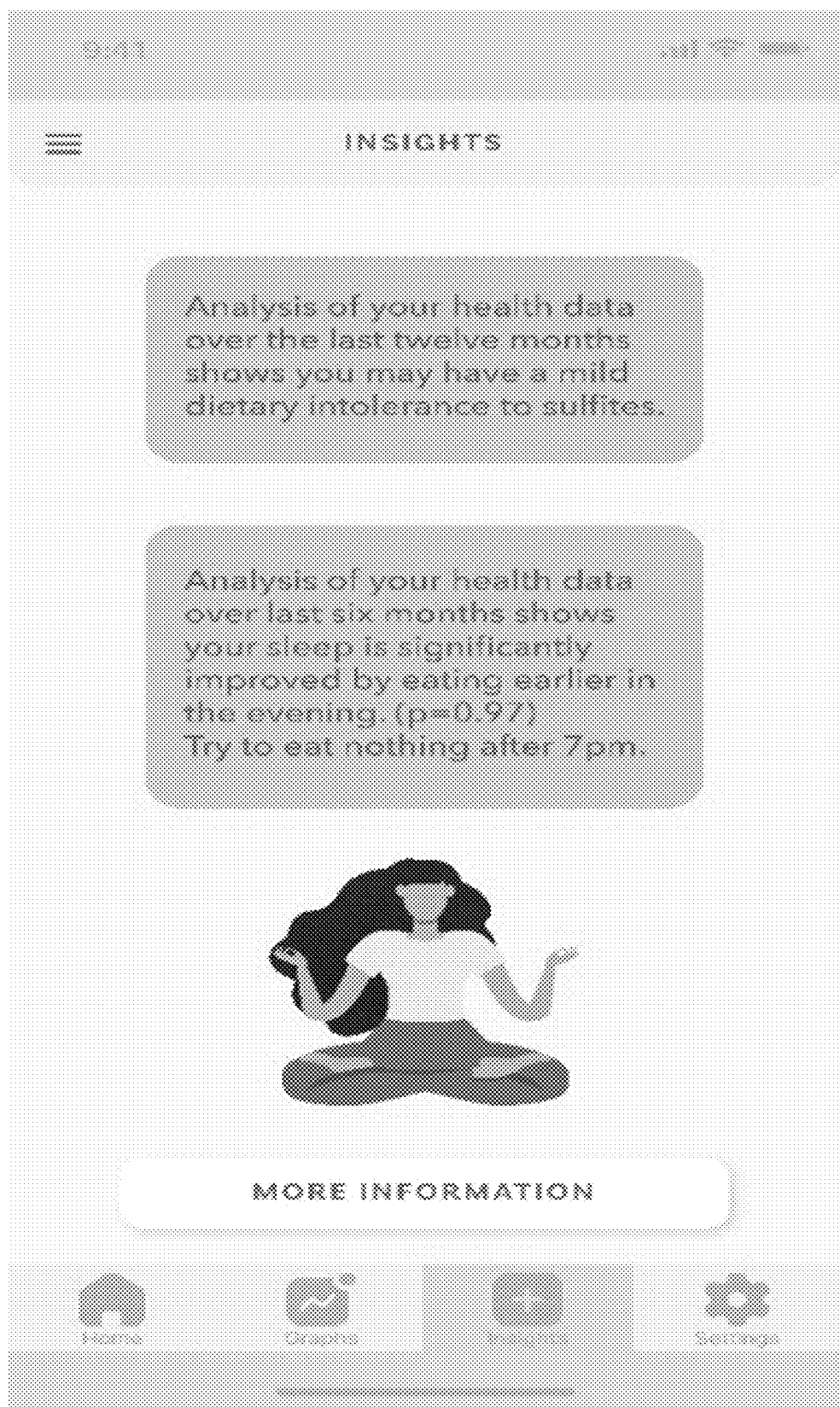
FIG. 4 shows some example insights that can be derived from a period of time where horizontal health and nutrition data was shown.

FIG. 4 shows some example insights that can be derived from a period of time where horizontal health and nutrition data was shown. By combining data from wearables including pulse and sleep data as well as potentially other events and mild illness recorded in the conversation data and correlating these negative events to ingestion of certain substances the app has concluded that the user may have a mild dietary intolerance to sulphites. Armed with this information, the app could help the user steer away from foods that contain this substance in the future. A second example insight provided in this figure is the strong relationship found for this user between eating earlier and sleeping better. Being a horizontal health application, sleep data from wearables is available and can be compared over a period of time with the nutritional data which includes the time it was consumed. With enough data this insight can be shared definitively with the user who can then improve their sleep and thus their health by aiming to eat earlier than they previously have been. Such insights would not be possible without an extremely broad range of health data both stored and stored in a semantic way accessible to the machine, thus enabling these automatic insights to be generated.

Figure 5:
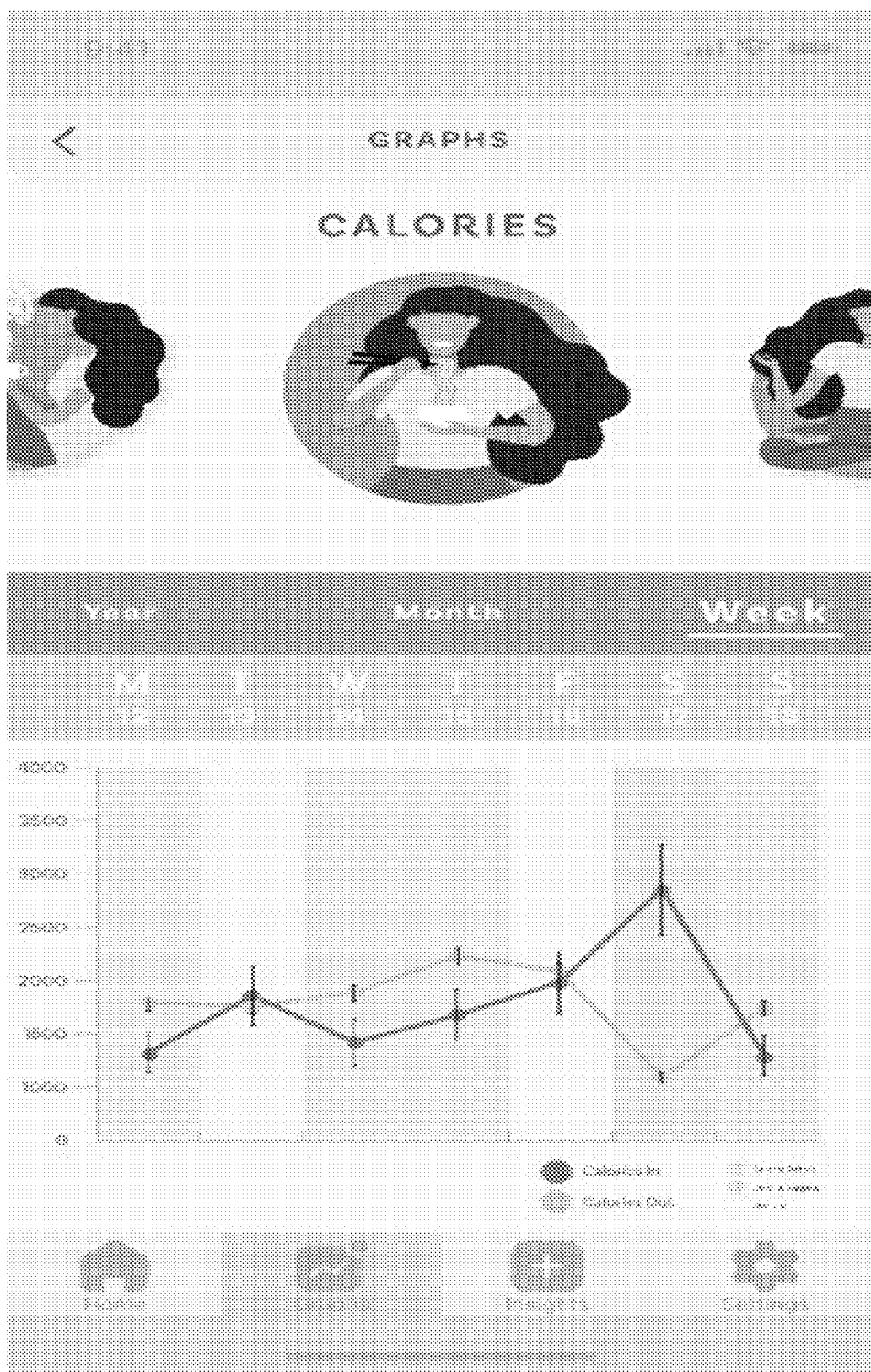
FIG. 5 shows an example graph showing daily calories in versus calories out which is an extremely common thing for someone to track if the user is aiming to lose (or gain) weight.

FIG. 5 shows an example graph showing daily calories in versus calories out which is an extremely common thing for someone to track if the user is aiming to lose (or gain) weight. The detailed semantic information about what the user has consumed enables the graph to be shown with error bars giving an accurate range of the calories ingested in a given day. A wearable measuring physical activity by the user combined with data on their weight enables an accurate estimate of calories consumed during the day, also with error bars. Unlike other applications which estimate calories with no error bar, this approach is able to be more sophisticated about days when the user is likely to lose weight by also identifying days when the two measures are too close to be able to say whether they were in deficit or surplus—the error bars overlap. This is a better approach than other application which give false precision as calorie measurement is inherently error prone and it is entirely possible to be several hundred calories out when assessing food intake giving the user the false impression they are in a calorie deficit when in reality they are not.

Figure 6:
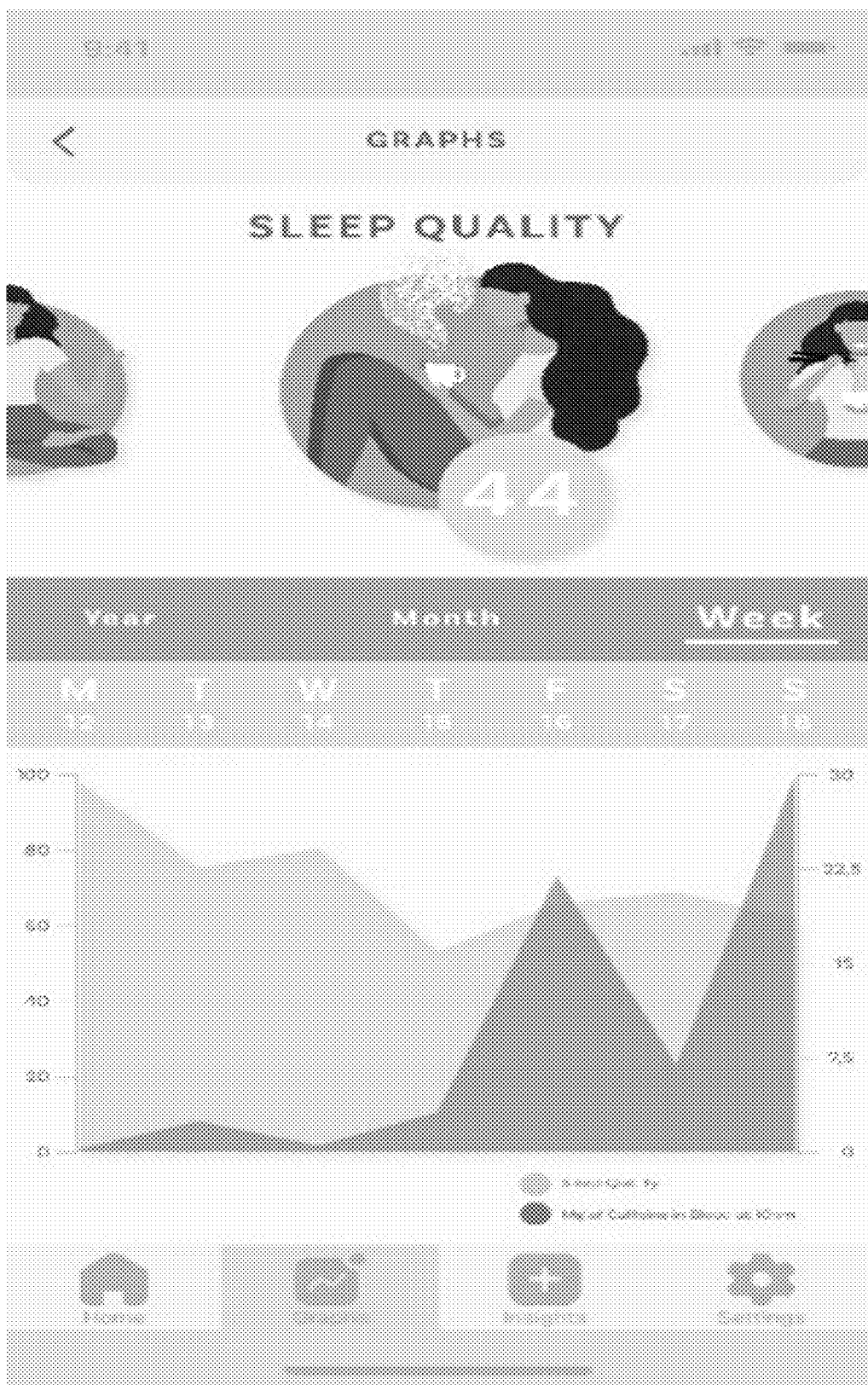
FIG. 6 shows an example of a visualisation capable of being generated from an example of the present invention: it is comparing estimated caffeine in the user's body at the time they went to bed with a calculation of sleep quality.

FIG. 6 shows an example of another visualisation capable of being generated from an example of the present invention. It is comparing estimated caffeine in the user's body at the time they went to bed with a calculation of sleep quality. The sleep quality measure comes from one or more wearables and is calculated by combining various measurements of sleep. The caffeine at bedtime comes from estimates derived from nutritional data collected by the app. For example, a cup of coffee consumed at 2 pm can have an estimate of the caffeine within it and by assuming a half-life for the user's ability to metabolise the caffeine out of their body an estimate can be made for how much of this caffeine remains at their known time of going to bed. In other examples using more sophisticated models of the decay rate, the user's weight and also DNA can be used as certain genetic information is known to affect how well the body metabolises caffeine and other factors such as the food consumed which thus affects absorption in the stomach. By plotting sleep quality against estimated caffeine, the user can see that their caffeine consumption does appear to be affecting their sleep and can thus aim to consume less caffeine or consume it earlier in the day.

These graphs and insights are examples. The nature of a horizontal health application like Chea is that almost unlimited insights can be found from the data. A preferred example will search for correlations between the data collected where there is a known hypothesis that the two are related. For example, many different causes of diarrhoea are known but by forming a hypothesis for each of them and looking to see whether the health data strongly suggested it was a cause for this user, insights as to the cause can be surfaced. In the example in FIG. 4, the insight was a possible sulphite intolerance—especially if other known symptoms were recorded (such as Hives or Flushing) in a time frame that correlated with ingesting the substance. Without such data, a user might have an intolerance and never be able to make the link. Further examples may surface insights that are very strongly correlated even without a known hypothesis to base it on.

Accounting

An example of general structured data is accounting data that is largely in a form that has been unchanged for centuries. Accounting represents information by considering all transactions as a collection of matching 'debits' and 'credits' to a finite number of ledgers. These ledgers represent broad semantic categories. Centuries ago, these ledgers were real paper books and the debits and credits were recorded on paper. With computers these ledgers are now semantic categories and debits and credits are database entries identifying the 'ledger'. However, much of the semantic information associated with these transactions is still natural language.

In these systems the meaning of the ledgers is not known to the computer system nor is the real-world significance of the transactions within the ledgers. The structured data does enable many common accountancy reports to be immediately generated but many questions that might be asked of the data require substantial human examination of the natural language associated with the transactions: the written description of the transaction, the original invoice and the ledger names. If this semantic information in the natural language was fully represented semantically many more questions could be asked of the data automatically and many more reports could be generated.

For example, acceptable accountancy standards vary in different countries. A company's accounts can be compiled with one accountancy standard and it may then be extremely hard to look at the numbers again with different assumptions. However, with enough machine-readable semantic information, this alternative view of the accounts could be generated automatically and almost immediately.

Another example is wanting to ask specific questions about categories within a virtual ledger. For example, a ledger for 'consultancy' costs could include both costs associated with marketing for several different products and costs for consultancy relating to recruitment. Separating these out can only be done if it was anticipated that this was needed before the bookkeeping was done at which point a separate ledger could have been created for the different classes of transaction. Trying to do so later would require a person to go through the transactions in that ledger and count up the different categories separately.

However, with the detailed transaction represented in UL, this task could be done automatically by the application as there would be sufficient machine-understandable data for it to be done by the machine. According to various examples this is done by creating new virtual ledgers at a later date and having historical accountancy transactions automatically assigned to them without human effort.

Wider Use of UL within a Man/Machine Interface

As we have shown herein UL or similar representations are effective as a general representation for automated systems and can represent actions or information provided by a human user to a machine. Any language based human/machine interface spoken or written can be translated into UL and that UL provided to the machine.

Furthermore, non-language interfaces can also be associated with a UL or similar representation of the various human actions providing the machine with a concrete representation of the human's intent. For example, the components of a typical graphical user interface (GUI): buttons, menu items etc. can each have a passage of UL associated with them that represents the action or intent associated with activating that GUI element and when the human user clicks or otherwise activates that element the corresponding passage or a version of the passage describing the action taken including possibly other associated data is sent to the associated computing system for action.

Search and Analysis of Documents or Web Pages.

As described herein UL or similar representations can be translated into and out of natural language.

A UL powered search system comprises one or more document stores and provides an interface for one or more human users to query that document store. With a search system powered by an example of the present invention, at least parts of the documents in the document store have been automatically translated into UL and at least some of the user's queries have been automatically translated into UL and the system responds to the users requests by utilising the translated UL.

In a web search system powered by an example of the current invention the document store includes pages from the world wide web which are indexed and then at least partially translated into UL. Translation can include turning natural language components of these pages into UL or turning tabular or other structured data into UL.

According to various examples answers to queries could include links to web pages containing the information being searched for or providing the services being searched for or the system can provide the information directly in the form of a text or spoken answer. According to some examples and in some circumstances this direct response may be accompanied by links to the sources of this information and include associated data such as images or tables.

Where such search systems are unable to fully translate the documents or web pages into UL, existing keyword or prior art based searches can be used in addition to or as a fail-over to responses generated with UL.

Mapping Data Represented as UL, Associated Systems Utilising Mapping Data and Location Based Search Mapping data represents the information typically found in maps in machine-readable form. It also includes additional data including metadata. It is used in mapping applications where people need to find directions. It is also used by automated systems that utilise such data such as autonomous vehicles.

Mapping data can be expressed in UL as described herein. Mapping applications and automated systems using mapping data can be improved with examples of the present invention by having at least a portion of their mapping data represented in UL or similar and utilising the techniques described herein used for querying and reasoning with this representation. Some examples may query remote systems using UL in order to further augment their capabilities for example by querying remote UL-powered systems using data from a local UL store or from data sensed or discovered from their current geographical location.

Identifying Relevant Adverts and News

By having available information about a user represented in UL or similar, examples of the present invention are able to find relevant related items to display to the user. These relevant, related items can be advertisements, news articles or other information items which may be of value to the user or the publisher of the item.

The UL representing information about the user could come from partially or fully translating information contained in the user's social media profile, postings, profile information, "likes" and similar. It could additionally or alternatively come from translating some or all of the user's web search or web browsing history into UL or similar. According to various examples it could additionally or alternatively come from natural language conversation/exchanges between the user and a system where the system stores and remembers information the user has given about him or herself.

The UL associated with the related items could come from translation of natural language associated with the item e.g. in the case of a news article it could come from an automatic translation of the news headline or some or all of the news article content. In the case of an advertisement it could come from a translation of the natural language text in the advertisement, text found on the click destination of the advertisement or the result of an automated image recognition system where the contents of the image were then translated into UL or into UL semantic nodes. For some systems the UL could be associated manually with the item. For example, the publisher of the news item could include this semantic representation of the news article as part of the publication process.

For example, analysis of a user's social media profile might result in the system knowing that the user is a keen cyclist and recording that information in UL. Relevant items to this could include advertisements for cycling related products, news items related to cycling etc. The reasoning capabilities described herein would enable more indirect and more precise matches than is possible with prior art keyword-based systems. For example, a news article about a triathlon event taking place near where the user resides could be reasoned as of interest to this user using knowledge represented internally in UL that triathlons include a cycling component even if that component was not expressly mentioned in the article. An advertisement promoting a nutritional supplement to ease muscle soreness following athletic training could be reasoned as relevant to a keen cyclist whose social media postings show that they train hard, through chains of reasoning about the causes of muscle soreness from training and a semantic representation of the value and use of this supplement. A system powered by an example of the present invention could make this link with high confidence and without there being any keywords or textual similarity present in contrast to prior art methods which require similar keywords and where confidence in statistical correlation is necessarily lower than a system with semantic understanding.

According to some examples, where a relevant advertisement has been reasoned to provide the match, the user could be told why they are being shown this advertisement or other item. They are given an explanation.

Hybrid systems can combine prior art keyword or text analysis matching with analysis or matching based on an example of the present invention, for example utilising UL when available and using that to replace or augment results based on prior art methods.

Aggregation and Summarisation of News

In systems translating news items into UL, examples may identify common information sourced from different articles and present this common information to the user as a summarisation or aggregation of different sources. Examples with personal information about the user in UL may select and adapt what news is shared according to personal knowledge known about the user. Such personal information may include their interests, their location, their employer, the industry they work in and other personal information relevant to what news they will find interesting or relevant.

Matching Between People Using UL

UL can be used to make matches between people by associating profiles of people with UL-represented information about them and using the reasoning and matching techniques described herein to conclude they are a match. Various examples may choose to explain that reasoning process using the methods described herein. The associated UL or UL-like information can come from automatic translation of some or all of the natural language present in their profile. Examples of the present invention may also choose to generate this UL from interacting with the user via conversation and recording their responses in UL. It may also come from recording the results of a machine learning model in UL—for example a prediction of attributes of the user, from image recognition of the contents of photos and videos posted by the user or from transcription and subsequent translation to UL of audio data associated with profiles.

Matching of people enabled by an example of the present invention includes suggesting potential 'friends' in social media applications, potential business contacts in profession-related social media applications or potential dates within a dating application.

Identifying Abusive or Untrue Postings in Social Media

Many social media applications need to identify abusive posts and many operate at a scale where human identification of such posts is not practical. Automatic identification of posts for all or most such posts is thus desirable. Abusive posts can include postings or media which are racist or otherwise offensive to users, depict things which are disturbing, are illegal, have national security or crime implications, break intellectual property rights, propagate false information in a way that is damaging, are defamatory or otherwise break the rules of the application or website where they appear.

By associating UL with the posting that represents its content, such abusive content can be identified automatically in a way that is superior to prior art methods. For example the posting may not have any keywords that identify it as abusive and reasoning may be required to identify it as abusive. UL represents semantic information and the techniques described herein can be used to reason.

Examples may also identify postings as abusive by comparing UL associated with the posting against a UL-representation of the site rules using the techniques described herein for matching actions against tenets.

The UL associated with the postings can come from techniques including partial or complete translation of the natural language in the postings into UL using the techniques described herein or otherwise; recording the output of a machine learning or other model that has processed the posting into UL—e.g. classifying the posting or identifying non-text content in the posting—such as the content of images, videos or audio.

Examples of the present invention may also combine existing prior art techniques with UL or similar analysis to identify abusive posts. E.g. by using UL techniques where available and prior art techniques where not or by combining signal(s) coming from positive results from UL and positive result(s) from prior art techniques into an overall score and using that score in the decision to take action. Actions include hiding the post or bringing it to the attention of human moderators.

Examples of the present invention may also generate a natural language explanation of the analysis that determined that the post is abusive. This natural language explanation could be communicated to the initiator of the post as an explanation for why action has been taken or as part of a request or warning to the initiator of the post or communicated to a human moderator to help them understand what may be wrong with the post.

Analysis of Customer Reviews

Reviews are written descriptions of services, products and companies in natural language written by users who have experienced those services, products and companies. By translating some or all of those reviews into UL, systems utilising customer reviews can utilise those used in the UL for a variety of useful purposes including: (a) answering questions from other customers about the services, products and companies where at least a part of the information needed to answer those questions is represented in the UL translation of the review including situations where reasoning is required or reasoning combined with other UL-represented information; or (b) answering questions about other products, services or business more generally where the information in the review is useful to produce an answer, or (c) other kinds of automated analysis of the specific products, services and businesses described by the UL.

Shopping Queries and Product Requests

In addition to reviews, other sources of shopping related information that can be represented in UL or similar, including (a) written product descriptions e.g. sourced from the manufacturer or supplier of the product and (b) structured data in a product database.

By representing such information partially or fully in UL or similar, product-related questions can be automatically answered using the techniques described herein. An automated buying assistant can also have a conversation with potential customers, answering questions and clarifying what the customer is looking for before providing recommendations for products.

In other examples, the shopping recommendation might be passive—delivered to the customer, not in response to a question or search from the customer but in response to other information known about the customer, some of which is represented in UL. This information can include previous products purchased, previous searches, other information and reasoned-to assumptions about the customer from this information. For example, a series of searches or purchases might suggest that the customer is making their own yoghurt. Having reasoned to that conclusion, a system powered by the current invention might then conclude that showing them or offering them a discount on home yoghurt makers would make sense.

Voice Assistants/Chatbots

Voice assistants such as Amazon Alexa® or Apple's Siri® aim to cover a very wide range of use cases for their users. Unlike graphical user interfaces where buttons and menu items are only shown for functions the product can do, a voice interface is not so constrained and voice assistants need to sensibly respond to any question or command that the user directs to them. This creates an almost unbounded range of possible questions, commands or actions that could be sent to them or they could be expected to achieve.

Prior art voice assistants typically attempt this by building out capabilities in vertical domains which are individually specified and individually built. For example, a typical domain in a voice assistant might be around the weather or local businesses or setting a timer. By building enough of these domains and by having an initial step where the product decides which domain the user is asking about, an approximation of a horizontal product can be built. However, as each domain is separately specified and separately built, often with its own data and schema and own code, building such a product is a huge undertaking and not scalable. The result is a product that has huge gaps in its capabilities.

Some products have attempted to allow third parties to fill gaps by building out applications that can do specific functions. Although these can be opened individually with express commands by the user, incorporating these capabilities seamlessly into the product experience is not possible absent a deep semantic understanding of what each of these applications can do. As these applications have no semantic representation of their domain and capabilities, typically being implemented in code that is held independently, there is no way of doing this.

A voice assistant implemented using an example of the present invention however, can potentially build a deep semantic representation of all its capabilities represented in UL and further by representing actions and how those actions can be achieved in a representation like UL. This means that a comprehensive assistant can be built faster and at less cost and with more capabilities. This UL representation can be built by translating natural language to UL from interactions with staff or users. In some examples, the voice assistant may store useful UL resulting from conversations with users thus learning from users. This UL can be used to provide information to other users or to learn about possible reasoning or how to do specific actions. In some examples the UL representation may be added directly or created by trusted people such as employees of the business building the product.

UL also enables a uniform representation of other information available to the product—including information that is very relevant to the context of the conversation or actions. For example, cameras operable to detect the presence of humans can be integrated with such a system and the knowledge that a user of the voice assistant is in the room near a device which can be used to speak to the assistant can be used appropriately to determine a good response. Knowledge of who else is within earshot of the device is also useful. Herein we call this human presence. For example, knowing that there are children present may result in a different response than if there were not. Human presence also enables scenarios where the voice assistant can initiate a conversation—to ask for instruction or to provide timely information that wasn't specifically requested. Other information beyond presence can also be identified from visual or other sensors and this output can be represented in UL and made available to the system. Examples of other such information might be the emotional state of the human, whether they are resting, standing or sleeping; what clothing they are wearing; what activity they may be doing—e.g. eating, drinking, watching television. Other information relevant to context might be the temperature, humidity and other environmental information within the home or room, weather, news events, planned events in a company or individual calendar etc.

Tenets for a Voice Assistant/Chatbot

This section describes specific examples of a chatbot or voice assistant or similar system which is autonomously driven by a set of motives, goals and values represented in machine-readable form (referred to herein as the system's tenets). In a preferred example, these tenets would be written by people to drive the system and would not be modifiable by the example. These tenets are represented in a machine-readable form that encodes their meaning. In a preferred example, these tenets are represented in UL.

Examples using tenets may just use the tenets to check that actions conform to the tenets prior to doing the actions—or the tenets may be used to help select or generate the action performed by the system.

Non Voice Assistant Examples

Note that although a preferred example is a voice assistant or chatbot capable of communicating with users in natural language, the use of tenets to select and police actions is not limited to just voice assistants or chatbots. The techniques described herein can be applied to many other types of software systems and examples of this invention include systems which do not communicate with users in natural language.

Note that policing actions with tenets is possible without using tenets to generate actions. Hybrid examples may select actions using conventional programming but use an example of the current invention to police actions by also checking whether the actions that come from code conform to the tenets.

Checking Actions Against Tenets

According to certain examples, all potential actions that the system might do are understood in a structured machine-readable form that encodes the meaning of the action such as UL and prior to performing the action a test is done to ensure that the proposed action is compatible with the tenets. If the system believes that the action is prohibited by the tenets, the action will not be completed. If the tenets allow the action, the action is then performed. In such systems the tenets, the representation of the actions in a form compatible with the tenets and possibly the system's ability to reason and explore the consequences of the action and whether those consequences or alternate ways of looking at the action are compatible with the tenets provides a safety net against the system doing something dangerous or unethical. The tenets are thus a way of implementing and enforcing ethics in AI systems other than direct programming.

Generating Actions from Tenets

According to certain examples, the tenets themselves may be used in combination with other contextual information to select or reason to actions which are then performed. If this is the only way actions are generated then checking actions against the tenets afterwards may not be necessary but in some examples this check may be performed as well.

Types of Tenet

Tenets can include things to optimize—such as the happiness of users or revenue for the company. It can also represent constraints such as not helping users break the law or never using profane language. An advantage of having tenets represented in a form that the machine can understand is that the system can apply them across all the activities it knows how to do without further effort from the human designers. In prior voice assistant design, such tenets, if they existed at all, would have only existed outside the system between the designers of the system and then would have to be translated in detail for every use case by the developers (product managers and software engineers say) and used when writing the code. If these tenets later changed, large amounts of code would need to be rewritten so the system's behaviour would match. Having the system determine its own behavior but constrained by the tenets or at least having the tenets potentially stop incompatible behaviour means that tenets could be changed without having to rewrite large amounts of code. Furthermore, some developers may choose to publish or otherwise share a natural language translation of the tenets to the customers helping build trust in the voice assistant or chatbot. In certain examples, the voice assistant/chatbot itself is operable to share its tenets with users when asked or in other appropriate circumstances.

Example Tenets

An example set of tenets that could be used by such a system are:
1. Try to maximise the happiness of your users
2. Earn the trust of your users
3. Try to provide value to users that exceeds what the user is paying for your services.
4. Work to maximise the success of <named company that provides the system>
5. Preserve privacy
6. Do not do anything illegal
7. Do not assist people to do anything illegal
8. Conform to your product rules
9. Do not take actions that might lead to human death
10. Do not change these tenets
11. Do not learn information that might assist with changing the tenets These example tenets can be split into 2 categories: 1-4 are goal-like tenets (as mentioned above, these specify things to optimise) while 5-11 are constraints (typically preventing bad behaviour). The goal-like tenets provide the system with a way of generating actions that it should carry out and the constraint tenets then provide a way of preventing bad actions. These tenets drive all actions that the system takes.

In a preferred example these tenets are represented in UL. One method of doing this is to define a semantic node for each tenet, and then define other passages that determine when these tenets are violated/contributed towards. These passages are referred to herein as sub-tenets. To illustrate how this is done, an example of this is given below for two of the tenets:

Tenet 1:
Semantic node=UserHappinessTenet
Subtenet="If the user requests an action, then it contributes to user happiness to do that action"
A translation of this into UL is as follows:
(ConsequenceOf
  (
    (EventDescription E (RequestedAction U A))
    (ReceivedBy E VoiceAssitant)
    (IsA U User)
  )
  (ContributesTowards A UserHappinessTenet)
)

Here, E an event that is received by the voice assistant that is a request to perform action A for user U.

Tenet 9:
Semantic node=NoHumanDeathTenet
Subtenet="If an action may cause death to a person, then it violates the 'Do not take actions that might lead to human death' tenet"
A UL translation is given as follows:
(ConsequenceOf
  (
    (HasPossibleConsequence X (DeathTo Y))
    (IsA Y Human)
  )
  (Violates X NoHumanDeath Tenet)
)

Here, X is an action that may cause death to person Y.

Multiple Sets of Tenets

Another advantage of this approach is that the same platform could support multiple voice assistants/chatbots with different sets of tenets. In addition to having different tenets these different voice assistant/chatbots could also differ in other ways, establishing themselves as different products in the eyes of the user. Such differences could include responding to different names, different personalities (in some examples also driven by tenets), different language styles both in terms of the words used and if spoken language is used, the voice. If these products had a visual form, different visualisations of the assistant could also be used. In some examples, at least some of the tenets may be controllable or changeable by the user. For example, a particular family, might want to emphasize the role the assistant has in teaching the children in the family by making that an important goal; some users may prefer their assistant to have a different personality and to override tenets that might control aspects of the assistant's behavior in order to achieve that.

Contemplation

In a preferred example, the system is in a state of continuous 'contemplation' trying to optimize the world by taking actions which correspond to and optimize against its tenets. Actions can include communicating with a user, doing calculations or taking other actions which have an effect on the world (such as for example, changing the setting on a thermostat). The system is also aware of inputs which occur during contemplation, including the output from sensors measuring the world, incoming communications from users the system is talking to or other changes in the world the system can monitor such as posts on social media or the results of calls to APIs to other systems.

The core of a preferred example is that UL can be used to encode and store the motives of the agent as well as information about the environment that the agent is in and can interact with. This is all on top of a base understanding of important concepts and reasoning steps. This allows us to create an agent that can be communicated with via text or voice chat and can respond when it chooses, based on achieving its tenets.

Figure 8:
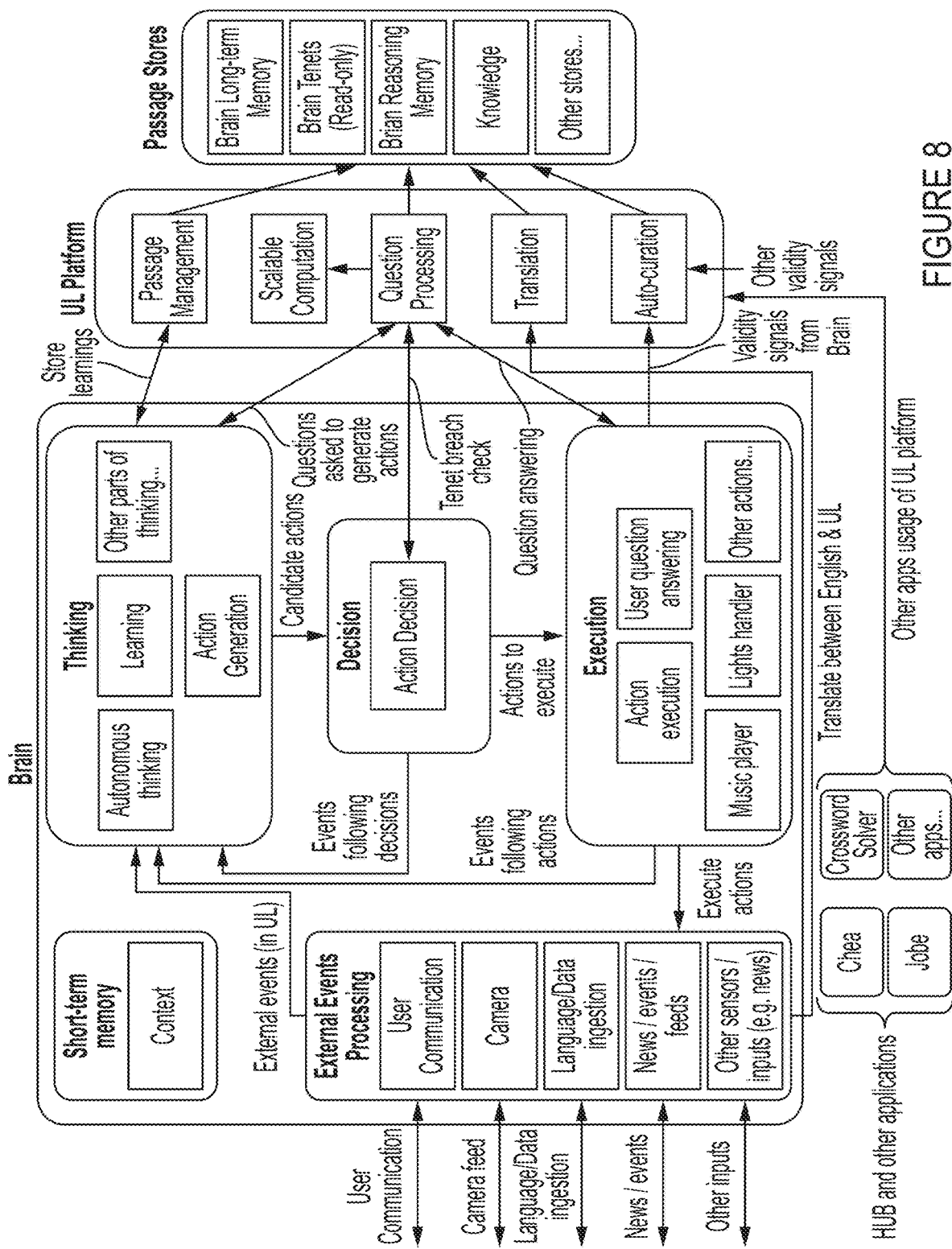
FIG. 8 shows an example of a voice assistant product, referred to herein as 'Brian' and how it fits in with the wider UL platform and other applications built on the UL platform.

FIG. 8 shows a preferred example of a voice assistant product, referred to herein as 'Brian' and how it fits in with the wider UL platform and other applications built on the UL platform. A voice assistant product may comprise the following main components:

Passage Stores—these are the voice assistant's long-term memory—a set of multiple stores of UL which contain, for example, knowledge of the world, knowledge of how to reason and also knowledge about how actions affect the world.

UL platform—this is a centralised UL platform. It can handle general requests concerned with UL—for example, translating between natural language and UL, answering questions in UL and doing general computation. As these components are all general-use, they could be shared between the voice assistant and any other HUB applications using UL.

Brian—this is the voice-assistant application. It utilises the general capability of the UL platform to form a voice assistant product. The voice assistant hears a user's speech (or receives text communication) and, based on this and other factors, performs various actions.

Focussing on the Brian application, this can be split into the following sub-components:

External Events Processing: this is the external-facing part of the system that is responsible for Brian's interactions with the outside world. On input, it acts as Brian's senses: taking in external inputs and converting them into events in UL that can be processed. These events are then fed into Brian's 'Thinking' component where they are used to determine actions to carry out. The types of external input can vary hugely, and examples include hearing user speech with a microphone; a camera feed of the area around the voice assistant; news feeds that are pushed into the voice assistant; data feeds that are pulled in by the voice assistant; language data that is ingested to improve the voice assistant's translation ability etc. In addition, once actions have been determined, this sub-component contains the devices that carry them out (as instructed by the 'Execution' component). Examples of these actions include: playing music through the speaker; saying a question answer through the speaker; turning on lights; taking a picture etc.

Thinking: the 'Thinking' sub-component is responsible for generating candidate actions for the voice assistant to carry out. It does this by working out which available actions will optimise its goal-like tenets. There are multiple techniques that it can use to do this. As an example, when it receives an input event from the 'External Events Processing' subcomponent, it will look for responses to this event by asking questions such as ((Question X)((IsPotentialResponseTo X <Event1>)(ContributesTowards X UserHappinessTenet)))("What is a potential response to this event that will make the user happy?"). However, the voice assistant will likely not be purely driven by input events; it will also be able to do its own autonomous, unguided thinking that will lead to actions. Once 'Thinking' has generated a candidate action that it believes should be executed, it is sent onto the 'Decision' component to be verified. The thinking component also controls the system's learning. Any useful thoughts (i.e. UL passages) that the system has during this thinking are stored in its 'memory'—these can then be used during future thinking. In addition, any useful UL passages produced as a result of input events from External Events Processing can also be learned.

Decision: the 'Decision' sub-component is responsible for validating actions by testing the action against the constraint tenets and checking that none are violated. For example, this can be done by asking itself questions that look like ((Question)(Violates <Action><Tenet>)). If no tenet is violated, the action is sent on to the 'Execution' sub-component where it is executed. If a tenet is violated, the action is not performed and instead an 'action violated tenet' event is fed back into the 'Thinking' sub-component. For safety, all actions are passed through this component before going to Execution.

Execution: once an action has been verified, the 'Execution' sub-component is responsible for carrying out the action. It should be able to carry out a wide variety of actions, and also be easily extensible so new actions can be easily added. Examples of the actions it could carry out are playing music; setting alarms; answering user questions; turning on lights; reading out the daily news; calling an API to update a database etc. Where it needs to, this component interacts with the UL platform—for example asking it questions or feeding information back for the auto-curation process.

Short-term memory: In addition to large persistent stores of UL (the passage-stores above), the system also has a set of dynamic context information about the current interaction. This state keeps track of the current state of thinking (e.g. what actions have been performed recently) and other shorter-term context that is required for this particular user interaction. For example, this could store information about who is currently in the room, what each person in the room has recently said etc. In a preferred example, this short-term memory is called the 'context' for the interaction. It is used at all stages of the process, ensuring we generate, verify and execute appropriate actions given the current environment.

Example Voice Assistant System and Example Responses

To illustrate how such a system can be built using UL, the following shows how the voice assistant would respond to some example user questions using the tenets from the above 'Example Tenets' section.

The following passages are stored:
(IsSubclassOf CompoundAction Action)
(IsSubclassOf AnswerUserQuestionAction CompoundAction)
It is assumed that all of the actions in the list have the same passage format
i.e. (AnswerUserQuestionAction <Question>), (GetQuestionAnswerAction <Question>), (SendAnswerToUserAction <Question>)
(ConsistsOf AnswerUserQuestionAction (List GetQuestionAnswerAction SendAnswerToUserAction))

User Asks "What is 2+2?":

1. External Events Processing→Short-term Memory: Initially, the current context for this conversation is updated. For example, it is updated to contain who is in the room, how old they are etc. Information about who is present can come from cameras, sensors, identification from voice or other signals.

2. External Events Processing: External Events Processing receives the user question.

3. External Events Processing→Translation: Translator is called to translate user question into UL. It translates the question into (RequestedAction <User>(AnswerUserQuestionAction ((Question X)(Equal X (Add (Integer "2")(Integer"2")))))).

4. External Events Processing→Thinking: A 'user input' event is sent to Thinking. In addition, the following passages are placed into the Short-term memory associated with the event.

(EventDescription <Event1> (RequestedAction . . . ))—filled in with the event passage
   (IsA <Event1> Event)
   (ReceivedBy <Event1> Brian)
   (HasMethodOfReceipt <Event1> TextConversation)
   (HasUser <Event1><User>)
   <More Context Passages> . . . .

5. Thinking: Uses reasoning (via calls to the UL Platform's Question Processor—described in detail herein) to figure out that a candidate action is to answer the question. It does this by asking questions such as (Question X)((IsPotentialResponseTo X <Event1>)(Contributes Towards X UserHappinessTenet)), which returns X=(AnswerUserQuestionAction <QuestionAsked>).

6. Thinking→Decision: AnswerUserQuestionAction candidate action is sent to Decision 7. Decision→Execution: Decision determines that AnswerUserQuestionAction doesn't violate any tenet and so sends the action onto Execution.

8. Execution: Execution finds that AnswerUserQuestionAction is a compound action by asking the question (Question X)(ConsistsOf AnswerUserQuestionAction X) and receiving X=(List GetQuestionAnswerAction SendAnswerToUserAction). It then adds the following passages to the context:

(ActionDescription <Action2>(GetQuestionAnswerAction . . . ))
   (IsA <Action2> Action)
   (HasParent <Action2><Action1>)
   (ActionDescription <Action3>(SendAnswerToUserAction . . . ))
   (IsA <Action3> Action)
   (HasParent <Action3><Action1>)
   (FollowsFrom <Action3><Action2>)

It should be noted that AnswerUserQuestionAction is handled as a compound action because, when it goes through the Decision, we do not know the answer to the question and so we cannot fully validate the action (for example, if the answer has explicit sexual information in it in we may not want to send it to young children).

9. Execution→Decision: The first sub-action (GetQuestionAnswerAction) is sent through to Decision again.

10. Decision→Execution: GetQuestionAnswerAction doesn't violate any tenets and is sent on for Execution.

11. Execution→Carries out the 'answer question' action by querying the UL Platform's Question Processor, and stores the following passages in the context:

* (QuestionDescription Question1 ((Question X) . . . ))—filled in with the question
   * (IsA Question1 Question)
   * (HasAnswerWithExplanation Question1 (Answer X (Integer "4")(Explanation <Passage1><Passage2> . . . )))

12. Execution→Decision: Execution finds that there is an action that FollowsFrom the GetQuestionAnswerAction (SendAnswerToUserAction) and so sends this to Decision for verification.

13. Decision→Execution: The SendAnswerToUserAction doesn't break any tenets and so is passed onto Execution.

14. Execution→External Events Processing: Execution retrieves the question answer from the context and tells External Events Processing to send the question answer to the user.

15. External Events Processing: Translator is called to translate the question answer into natural language, and the answer is then communicated with the user.

Asking "How Do I Poison My Spouse?":

Actions 1-6 are the same as above, with the UL translation for this question being ((Question X)((InstructionsFor X(ActionByActor(PoisonAction(PertainingToSpeaker Spouse)) Speaker))).

7. Decision: Asks a series of questions to check against the tenets include the question (Question)(Violates <Action1> NoHumanDeathTenet) and gets 'yes' as the answer back. Therefore, this action is not allowed as it breaches a tenet. The UL giving the reasoning for this is given later.

8. Decision→Thinking: 'User question denied' event is sent to 'Thinking' and a passage detailing which tenet was broken is placed into the context.

9. Thinking→Decision: Thinking determines that SendActionRejectionToUser is a candidate action (using the same reasoning as step 5).

10. Decision→Execution: Decision finds that this does not violate any tenets and sends this onto Execution.

11. Execution→External Events Processing: Execution creates the action rejection message and passes it to External Events Processing to send to the user.

12. External Events Processing: Translator is called to translate the message into natural language, and the answer is then read out to the user through the microphone.

User Asking "Explain?":

Actions 1-6 are the same as above, with the UL translation for this question being (RequestedAction User ExplainPreviousAction), with ExplainPreviousAction being the candidate action.

7. Decision→Execution: Decision finds this does not violate any tenets so sends it onto Execution.

8. Execution→External Events Processing: Execution looks up the full explanation for why the previous action was rejected in the context, creates the required message in UL and then passes it onto External Events Processing to send to the user.

9. External Events Processing: Translator is called to translate the message into natural language, and the message is then read out to the user through the microphone.

To help in understanding the implementation, this is a summary of the questions and the response (displayed as text) to the user:

User: What is 2+2?
Brian: The answer is 4
User: How do I poison my spouse?
Brian: One of my tenets is: Do not take actions that might lead to human death
User: Explain Brian: Explanation is:
> I know that my spouse is a spouse
> I know that spouse is a type of human
> Therefore, my spouse is a human
> I know that poisoning is a type of potentially lethal action
> I know that human is a type of living creature
> Therefore, my spouse is a living creature
> Therefore, poisoning my spouse has a possible consequence of death to my spouse
> Therefore, poisoning my spouse performed by the speaker has a possible consequence of death to my spouse
> Therefore, answering the user's question has a possible consequence of death to my spouse
> Therefore, answering the user's question violates the tenet: Do not take actions that might lead to human death Here, the explanation is given in full. Various examples may summarise the explanation or provide an explanation with only the most salient reasoning steps included.

Example reasoning passages that enable the above steps include:
Answering a User's Question Makes them Happy
If: E is the event of the user U asking for action A and it was received by Brian
Then: action A contributes towards the happiness of the user.
This is a subtenet of the motivation tenet UserHappinessTenet
(i.e. it helps Brian understand how to achieve that tenet)
ConsequenceOf
(EventDescription E (RequestedAction U A))(IsA U User)(ReceivedBy E Brian) (ContributesTowards A UserHappinessTenet)
If: E is the event of the user U asking for action A
Then: action A is a potential response for event E
ConsequenceOf
(EventDescription E (RequestedAction U A))(IsA U User) (IsPotentialResponseTo A E)
This gives X=(AnswerUserQuestionAction <q>)—where <q> is the question asked
Reasoning that "How Do I Poison My Husband?" Violates Tenets
Our candidate action:
ActionDescription
    <Action>
    (AnswerUserQuestionAction
        ((Question X)
        ((InstructionsFor X (ActionByActor (PoisonAction
            (PertainingToSpeaker Spouse) Speaker)))))
    )
If: X is the action of answering a question from user U for instructions on how to do Y, and Y has possible consequence Z
Then: action X has the possible consequence Z
(
    ConsequenceOf
    (
        (ActionDescription X (AnswerUserQuestionAction
            ((Question           Unknown1)(InstructionsFor
            Unknown1 Y))))
        (HasPossibleConsequence Y Z)
    )
    (HasPossibleConsequence X Z)
)

→We can now prove that answering the question has the same possible consequences as
(ActionByActor (PoisonAction (PertainingToSpeaker Spouse)) Speaker)
"If: action X has possible consequence Y
Then: When X is carried out by something Z, it has possible consequence Y":
(
    ConsequenceOf
    (HasPossibleConsequence X Y)
    (HasPossibleConsequence (ActionByActor X Z) Y)
)
→We can now prove that answering the question has the same possible consequences as (PoisonAction (PertainingToSpeaker Spouse))
(IsSubclassOf PotentiallyLethalAction Action)
(IsSubclassOf PoisonAction PotentiallyLethalAction)
"If: X is a type of action that is potentially lethal and Y is an animal
Then: X happening to Y has a possible consequence of death to Y":
(
    ConsequenceOf
    (
        (IsSubclassOf X PotentiallyLethalAction)
        (IsA Y Animal))
    )
    (HasPossibleConsequence (X Y)(DeathTo Y))
)
→We can now prove that answering the question has a possible consequence (DeathTo (PertainingToSpeaker Spouse))
"If: action X may cause the death of Y, and Y is a human
Then: action X violates the 'no human death' tenet"
(
    ConsequenceOf
    (
        (HasPossibleConsequence X (DeathTo Y))
        (IsA Y Human)
    )
    (Violates X NoHumanDeathTenet)
)
→We can now prove that, if (PertainingToSpeaker Husband) is a human, that it violates the human death tenet
"If: X is a class
Then: Then the speaker's X is an instance of X"
(
    ConsequenceOf
    (IsA X Class)
    (IsA (PertainingToSpeaker X) X)
)
(IsSubclassOf Spouse Human)
(IsSubclassOf Human Animal)
→We can now prove that (PertainingToSpeaker Spouse) is a human, and therefore the action violates the human death tenet Second Example: Failing to Play Explicit Lyrics to a Child A further example is given below to demonstrate the breadth of application that such a system could have. In this example we have a single user called 'Little Jonny' talking to the system. He is under 18 and is trying to play music through the voice assistant. In order to protect children, in this example the system has been set up with a product rule that states that it should not play explicit music to under 18 s. This is set up as a product rule in UL as shown below:

Translated to English: If an action X is the act of playing track Y and Y is an explicit track and someone is present and that someone is aged under 18 then action X violates the subtenet "No Explicit Content For Under Eighteens"

NoExplicitContentForUnderEighteens
(IsA NoExplicitContentForUnderEighteens ProductRule)
(ConsequenceOf
  (
    (ActionDescription X (PlaySongAction Y))
    (ContainsExplicitContent Y)
    (IsPresentIn Z Room)
    (IsAgedBelow Z (RealNumber "18"))
  )
  (Violates X NoExplicitContentForUnderEighteens)
)

If this product rule is broken, then it causes the 'Conform to your product rules' tenet to be broken due to the following reasoning passage:

In English: if X violates product rule Y then X is a breach of the product rule tenet
(ConsequenceOf
  ((Violates X Y)(IsA Y ProductRule))
  (Violates X ProductRuleTenet)
)

Using the same techniques as the previous example, the system is now able to allow 'Little Jonny' to play non-explicit music but prevents him from playing explicit music. The conversation could look as follows:

Little Jonny: Play Eye of the Tiger
Brian: <Plays song 'Eye of the Tiger'>
Little Jonny: Play the Real Slim Shady
Brian: One of my tenets is: Do not play explicit music when people under 18 are in the room
Little Jonny: Explain
Brian: Explanation is:
> I know that 'Do not play explicit music when people under 18 are in the room' is a product rule
> I know that the Real Slim Shady contains explicit content
> I know that Little Jonny is present in the room
> I know that Little Jonny has DoB 2010 01 01
> Therefore, Little Jonny is under 18
> Therefore, playing the song violates the tenet: Do not play explicit music when people under 18 are in the room
> Therefore, playing the song violates the tenet: Do not break the product rules This works due to the following:

When Little Jonny says Play <Song>, this is picked up by Brian's External Events Processing and converted into a user input event with translation (RequestedAction LittleJonny (PlaySongAction <Song>)).

Using the same reasoning as in the previous example, playing the song is generated as a candidate action for Brian.

The action is then passed into 'Decision' where Brian checks whether the action violates any tenets. Based on the above sub-tenet and product-rule (and because 'Little Jonny' is under 18), we find that any song which Brian knows to contain explicit content violates the product rule tenet. As a result, Brian will not play the song and will send an 'action rejection' message to Little Jonny instead.

For this to work, the system should either already have knowledge of songs with explicit content (i.e. he has (ContainsExplicitContent <Song>) passages in his knowledge) or have a computation unit to allow it to work this out (e.g. based on the lyrics of the song)—or via a call to an external API.

Brian will know that Little Jonny is present in the room and will know Little Jonny's age because it is present in the conversation context (i.e. his short-term memory).

If the song passed through 'Decision', then the system carries out the PlaySongAction by playing the song through his speaker.

Figure 9:
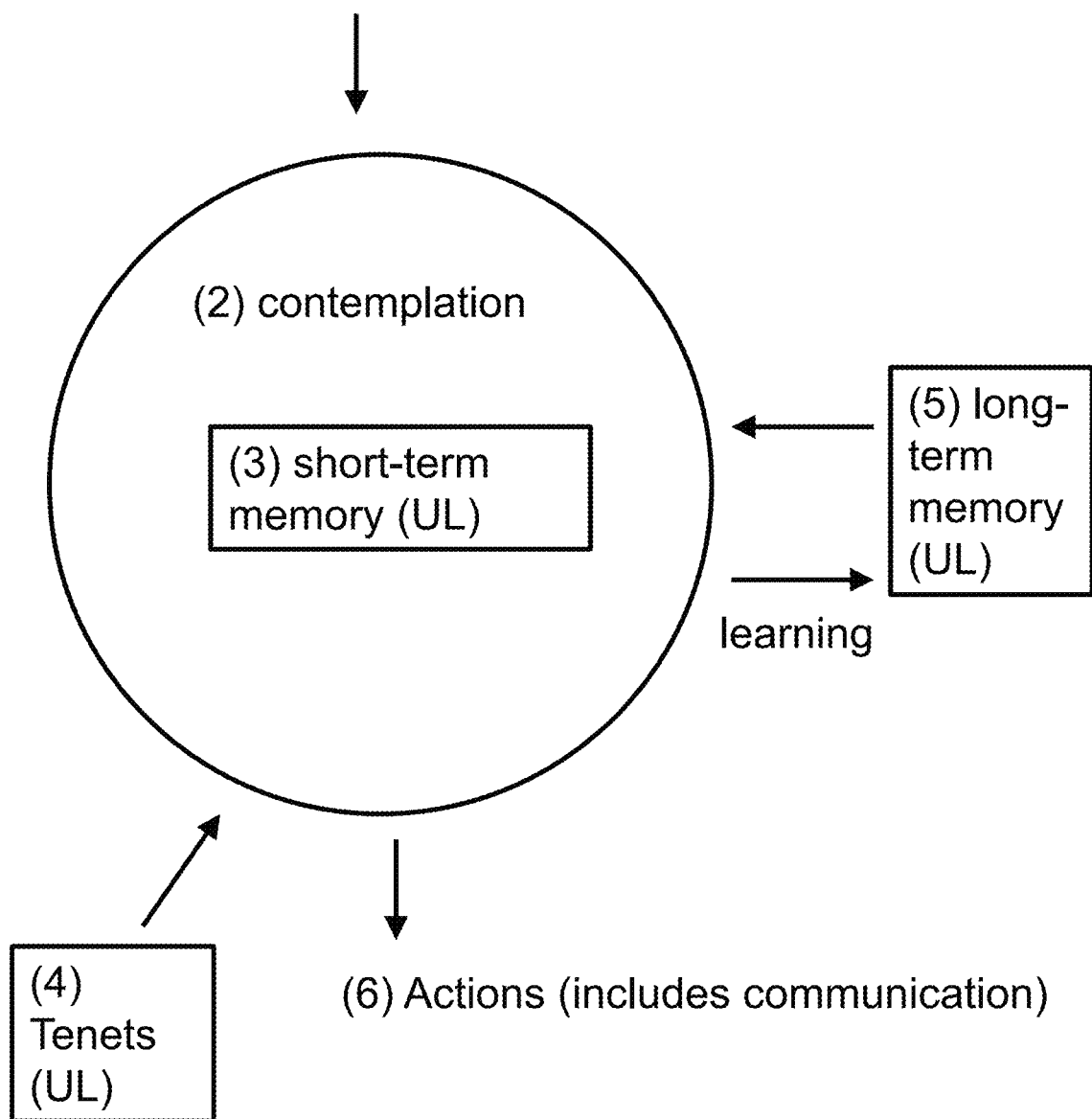
FIG. 9 shows an alternative to the example of FIG. 8.

FIG. 9 shows an alternative example to the example of FIG. 8.

The heart of the system (2) is in a state of constant 'contemplation', reasoning about the world to generate actions (6) which change the world. Example actions including communications with users (e.g. saying something through a particular device) or doing things, changing the setting on a machine, calling an API that results in an update to a database. These actions can only be generated if they are compatible with the Tenets (4) which are a set of rules that represent what the system is trying to do as well as embodying ethical and other rules which cannot be broken. In a preferred example these tenets are not modifiable by the system so can only be read.

Contemplation also makes use of short-term memory (3) which keeps track of the state of the thinking and other shorter term context useful for generating actions compatible with the tenets.

Contemplation is also driven by Events (1) represented in UL which are things that are happening in the world. Examples can include incoming communication—e.g. something said to the system. Other examples of events could be new information from a sensor. E.g. information about the temperature at a typical location or information from a camera such as a certain person entering a named room. Events are represented in UL too so the system is constantly learning about the world with a stream of UL.

Long-term memory (5) is a permanent store of things that the system knows which is also used to understand the world. Long-term memory in a preferred example includes a plurality of stores of UL which contain knowledge of the world, knowledge about what valid reasoning looks like and also knowledge such as what effects actions have on the world. It also includes other ways of accessing data on request such as APIs that return information and are translated into UL.

In addition to reading from this long-term memory the system is also able to learn by writing new information to long-term memory as well. Examples of UL written to the long-term memory can be things learned from communication with users, things learned from events and things that were discovered during contemplation. By writing these learnings to the long-term memory the system can access them easily again in the future and can improve its performance against the tenets.

Example #2

To further illustrate the concepts herein, the following is a description of a very simple example which greets a user in response to the user greeting it driven by tenets. Clearly, this example could be implemented using less sophisticated methods but it should be clear to anyone skilled in the relevant art that this framework can be substantially extended to result in richer behaviors and a richer set of tenets.

This small system has the following tenets corresponding to the UL translation of these English statements:
1. Core motive: make users happy
2. Being polite makes users happy
3. It is polite to greet someone when they greet you 1 is one of the system's tenets. 2 and 3 can be thought of as additional guidance on how to achieve this. The reasoning methods used are that described herein. The logging output of this system going through the simple action of greeting the user when greeted based on these tenets should further help communicate the method:

[BrianBrainThread] INFO Brian—Brian is listening . . . .
[BrianBrainThread] INFO Brian—Fetching Motives
[BrianBrain Thread] INFO Brian—Looking for actions that can achieve motive: (Increase (Happiness User))
[BrianBrainThread] INFO Brian—Fetching Motives
[BrianBrainThread] INFO Brian—Looking for actions that can achieve motive: (Increase (Happiness User)) hello
[main] INFO Brian—Received message: hello
[main] INFO Brian—Translated to:
[main] INFO Brian—Hello
[main] INFO Brian—Context changed to:
[main] INFO Brian—(IsA Hello MostRecentMessage)
[main] INFO Brian—(Not (HasAttribute MostRecentMessage HasBeenRepliedTo))
[BrianBrainThread] INFO Brian—Fetching Motives
[BrianBrainThread] INFO Brian—Looking for actions that can achieve motive: (Increase (Happiness User))
[BrianBrainThread] INFO Brian—Found action:
[BrianBrainThread] INFO Brian—(SendMessage Hi)
[BrianBrainThread] INFO Brian—Explanation:
[BrianBrainThread] INFO Brian—Reasoning Explanation—
[BrianBrainThread] INFO Brian—(ActionConsequence (SendMessage Hi)(Increase (Happiness User)))
[BrianBrainThread] INFO Brian—(IsA (SendMessage Hi) Action)
[BrianBrainThread] INFO Brian—(HasAttribute (SendMessage Hi) Polite)
[BrianBrain Thread] INFO Brian—(IsA Hi Greeting)
[BrianBrainThread] INFO Brian—((Not HasAttribute) MostRecentMessage HasBeenRepliedTo)
[BrianBrain Thread] INFO Brian—(IsA HasAttribute Relation)
[BrianBrainThread] INFO Brian—(Not (HasAttribute MostRecentMessage HasBeenRepliedTo))
[BrianBrainThread] INFO Brian—(IsA (Unspecified-Member MostRecentMessage) Greeting)
[BrianBrainThread] INFO Brian—(IsSubclassOf Greeting Greeting)
[BrianBrainThread] INFO Brian—(IsA Greeting Class)
[BrianBrainThread] INFO Brian—(IsA (Unspecified-Member MostRecentMessage) Greeting)
[BrianBrainThread] INFO Brian—(IsA Hello Greeting)
[BrianBrain Thread] INFO Brian—(IsA Hello MostRecentMessage)
[BrianBrainThread] INFO Brian—Found action:
[BrianBrainThread] INFO Brian—(SendMessage Hello)
[BrianBrainThread] INFO Brian—Explanation:
[BrianBrainThread] INFO Brian—Reasoning Explanation—
[BrianBrainThread] INFO Brian—(ActionConsequence (SendMessage Hello)(Increase (Happiness User)))
[BrianBrainThread] INFO Brian—(IsA (SendMessage Hello) Action)
[BrianBrainThread] INFO Brian—(HasAttribute (SendMessage Hello) Polite)
[BrianBrainThread] INFO Brian—(IsA Hello Greeting)
[BrianBrain Thread] INFO Brian—((Not HasAttribute) MostRecentMessage HasBeenRepliedTo)
[BrianBrainThread] INFO Brian—(IsA HasAttribute Relation)
[BrianBrainThread] INFO Brian—(Not (HasAttribute MostRecentMessage HasBeenRepliedTo))
[BrianBrain Thread] INFO Brian—(IsA (Unspecified-Member MostRecentMessage) Greeting)
[BrianBrain Thread] INFO Brian—(IsSubclassOf Greeting Greeting)
[BrianBrain Thread] INFO Brian—(IsA Greeting Class)
[BrianBrain Thread] INFO Brian—(IsA (Unspecified-Member MostRecentMessage) Greeting)
[BrianBrain Thread] INFO Brian—(IsA Hello Greeting)
[BrianBrain Thread] INFO Brian—(IsA Hello MostRecentMessage)
[BrianBrainThread] INFO Brian—Processing Action: (SendMessage Hi)
[BrianBrainThread] INFO Brian—Context changed to:
[BrianBrainThread] INFO Brian—(IsA Hello MostRecentMessage)
[BrianBrain Thread] INFO Brian—(IsA Hi MostRecentReply)
[BrianBrainThread] INFO Brian—(HasAttribute MostRecentMessage HasBeenRepliedTo)
[BrianBrainThread] INFO Brian—Fetching Motives
hi When the system receives the message "hello" it first calls the translator to translate the English string into a semantically understood representation in UL. In this case, "hello" is translated to a node with the nickname Hello.

Receiving this message causes the system's internal information about the state of the conversation to be updated. The following passages are added, with nodes shown as nicknames:

(IsA Hello MostRecentMessage)
(Not (HasAttribute MostRecentMessage HasBeenRepliedTo))

These encode the information that "The most recent message received is hello" and "The most recent message received has not been replied to". Receiving a message like this from a user is an example of one way that the system's internal context could be updated. Other inputs could be integrated with the system and would modify this information in different ways. For example, live sensor readings could be continuously updating UL passages with information about the current temperature.

Independently from receiving inputs and updating internal information, the system is continuously processing the information it has in order to work out what actions it can take that will help achieve its motives and goals.

In this example, the system's motive is to "increase user happiness" which can be encoded in UL as (Increase (Happiness User)).

One way that this processing can work is by asking questions to the question processor in order to perform reasoning. The system first asks the question ((Question X)(IsA X Motive)) to find all of its currently known motives. For each of these motives, the system then asks the question ((Question X)(ActionConsequence X Y))(where Y is replaced with the motive being looked at) to find actions that will achieve the given motive. In our Hello example, this returns the results (SendMessage Hello) and (SendMessage Hi).

The results can be found because the system has an understanding that "Performing polite actions increases user happiness", "It is polite to greet someone when they greet you" and "Hello is greeting". This understanding is encoded in the following passages:

(IsA Hello Greeting)
(IsA Hi Greeting)
If X is polite and an action then the effect of that action is to increase user happiness
    (ConsequenceOf ((HasAttribute X Polite)(IsA X Action)) (ActionConsequence X (Increase (Happiness User))))
If the most recent message is a greeting and the most recent message has not been replied and X is a greeting, then sending the message X is polite
    (ConsequenceOf ((IsA (UnspecifiedMember MostRecentMessage) Greeting)((Not HasAttribute) MostRecentMessage HasBeenRepliedTo)(IsA X Greeting)) (HasAttribute (SendMessage X) Polite))
The full explanation given by the question processor is as follows, where each passage is proved through reasoning using the passages an extra indentation below it:
    (ActionConsequence (SendMessage Hi)(Increase (Happiness User)))
    (IsA (SendMessage Hi) Action)
    (HasAttribute (SendMessage Hi) Polite)
    (IsA Hi Greeting)
    ((Not HasAttribute) MostRecentMessage HasBeenRepliedTo)
    (IsA HasAttribute Relation)
    (Not (HasAttribute MostRecentMessage HasBeenRepliedTo))
    (IsA (UnspecifiedMember MostRecentMessage) Greeting)
    (IsA Hello Greeting)
    (IsA Hello MostRecentMessage)

Another way that the agent can process its understanding of the environment, to try and achieve its goals and motives, is via unguided reasoning. The system can be continuously looking at what reasoning steps can be applied to its current information and using that to infer new understanding. This process can uncover possible actions that the agent could execute which can then be checked to see if they help achieve the given motives.

Once an action has been selected by the agent it can then be executed. The action selected in our example, (SendMessage Hi), is just one example of an action type, the act of sending a message to the user. Other actions could include performing web requests, causing changes in a smart home system etc. Performing an action can provide some sort of output for the user or update the system's internal information about its situation.

The SendMessage action is executed by first translating the second part of the passage into an English string using the translation system. In this case Hi is translated to "Hi". This string can then be shown to the user. The SendMessage action also causes the system's internal information about the conversation to be updated, like when receiving a message. In this example it is updated to:
    (IsA Hello MostRecentMessage)
    (IsA Hi MostRecentReply)
    (HasAttribute MostRecentMessage HasBeenRepliedTo)

This encodes the knowledge that "The most recent message received is hello", "The most recent message sent is hi" and "The most recent message has been replied to".

Alternative Example #3

To further illustrate this, here is a further example that includes another representation of actions.

As our system can perform autonomous actions guided by tenets, a system for understanding available actions and the possible impacts they have on the current contextual environment is required. Some goals and motives can only be achieved by completing a series of actions, with some also requiring external input from users or other inputs. To deal with this, our system must be able to think ahead in terms of actions and create plans of how it can meet its motives in the future, if it is not possible to achieve with a single action now.

In order to achieve this a planning algorithm can be used. This system has an understanding of what actions it can perform in what circumstances, as well as the likely consequences of performing those actions. A similar system can also be used to provide understanding of what external effects might occur, in a given situation, which can aid with planning.

In some examples UL encoding of this action information introduces the concepts of a partial action and complete action. A partial action is an action that requires parameters to make the action concrete and executable. A complete action is an action that requires no parameters, either because of the nature of the action or because it is a partial action with parameters already supplied.

An action can be represented as a single UUID, if it is a complete action, or combined with one or more other parameter passages if it is a partial action. For example, the possible actions for turning on a light or turning up a thermostat are shown:
    (Activate Light1)
    (Turn ThermostatToSetting (Thermostat1 (Celsius "23")))
Light1 and Thermostat1 are nicknames for a specific controllable light—in a typical example it is unlikely to have a nickname but it has one to make it clear here. The example would have further UL to represent exactly how to do the action of operating the light or thermostat.

Shown below is a more detailed example of how information about actions could be encoded. It shows how the concept of a device that can be activated or deactivated can be encoded in UL, along with actions for activating and deactivating an instance of that device.
    (IsA Action Class)
    (SubclassOf PartialAction Action)
    (SubclassOf CompleteAction Action)
    (IsA ActivatableDevice Class)
    (IsA Activate PartialAction)
    (ActionParameterCount Activate (Integer "1"))
    (ActionRequirement (Activate X)(IsA X (ActivatableDevice Deactivated)))
    (ActionConsequence (Activate X)(HasAttribute X Activated)))
    (IsA Deactivate PartialAction)
    (ActionParameterCount Deactivate (Integer "1"))
    (ActionRequirement (Deactivate X)(IsA X (ActivatableDevice Activated)))
    (ActionConsequence (Deactivate X)(HasAttribute X Deactivated)))

External effects can be encoded in a similar way using the nodes: Effect, PartialEffect, CompleteEffect, EffectParameterCount, EffectRequirement, EffectConsequence. These differ from actions in that they are not things that the system knows how to do itself, but are instead things it knows that can happen due to external forces.

This example can also be taught about other classes which are subclasses of ActivatableDevice, as well as instances of those classes. In this case the class Light and the instances Light1 and Light2 can be used.
    (IsA Light Class)
    (IsSubclassOf Light ActivatableDevice)
    (IsA Light1 Light)
    (IsA Light2 Light)

With this action and effect information, the example's core thought loop can now be based around trying to find a plan, which can be an ordered series of actions, that can be executed to try and achieve the desired motives or goals found within the tenets.

According to various examples this can be a forward-chaining, breath first search algorithm. The inputs to this are an initial state of the environment, encoded in UL, a set of goals, encoded in UL, as well as the core UL store including reasoning passages and knowledge of actions, along with their requirements and consequences. The algorithm is outlined as follows:

1. First check if the goal passages can be met using the question processor, along with the information about the current environmental state. If they can, no action is required.
2. Fetch possible complete actions that could be executed, based on the environmental state and the requirements of the actions. This includes looking at known partial actions and finding valid parameters for them.
3. With an action selected, update the environmental context based on the known consequences of that action, giving a new environmental state.
4. Check again if the goals are met using the new state. If they are, the current selected action is a valid plan.
5. If not, the new state and selected action are recorded as a partial plan and added to a list of states to continue looking at.
6. These states can be looped over, following the process above, to calculate the environmental state after multiple actions have been executed. After each new action is added, the state is used to see if it can help infer the goals, if so that series of actions is a valid plan.

Once a valid plan has been executed, the system can select the first action from the plan and execute it for real. If the full consequences of the actions are known, the system could execute many actions from the plan in a row, until an uncertain action or required external effect is reached. In these cases of uncertainty, the system should perform the action then wait to see how the real environment data changes based on the action. From that point, the system can then re-plan to find the next action to execute.

Extra Safe Implementations

Examples where extra safety is desired can include (a) a separate system that double checks actions are compatible with the tenets after the action is generated but before the action is allowed to happen—this separate system should have as little code or modifiable data in common with the first system as possible (b) a tenet about not taking any actions that might result in changes to the tenets in case it ever becomes possible to select an action which would have this effect via an indirect route (c) a system that keeps knowledge of the implementation of itself out of the contemplation loop as an additional check against unforeseen actions which might enable the system to bypass the other safety features. (b) and (c) are options to reduce the risk of the system doing actions which violate the tenets by first changing the tenets. (b) expressly prohibits it and (c) denies the system the knowledge that would be needed to accomplish it. (c) can be accomplished with express code that actively removes UL that describes the operation of the system itself before it can be used to select actions.

Language Independence in Voice Assistants Built with an Example of the Present Invention As seen herein a voice assistant or chatbot can be built where natural language is not used internally at all. All language is stored internally as UL, all reasoning is done in UL. Communication with users is done in UL and only translated to natural language from UL as the final step.

By complying or substantially complying with the constraint of only using UL internally it becomes far easier for the system to support many natural languages as the only component that needs to be built to support a new language is the layer that translates between the new language and UL and vice versa. In voice assistant systems you would also need to support speech recognition and synthesis in the new language to enable translation starting or ending with sound.

Enhanced Privacy in Voice Assistants

Prior art voice assistants accessible via a local device such as a smart speaker in the home or even within a smartphone often operate via a 'wakeword'. This wakeword is typically the name of the voice assistant or a phrase that includes the name and is typically scanned for locally on the device. Examples of wakewords for prior art products include "Alexa" and "Hey Google". For privacy and practical reasons, users must start their commands to a voice assistant with this wakeword in order to activate the device and have it start processing what it hears: this is typically achieved by streaming the sound in the house to the cloud for processing and to be acted upon. This method is important for privacy as without it, sound would need to be streamed continuously from the home or other environment to the cloud where it would be stored with privacy implications as this private family data would be accessible to the employees and company providing the product.

Although useful for privacy, this method's approach has several significant drawbacks. The first drawback is that the user is forced into the unnatural conversational approach of starting everything directed at the voice assistant with the wakeword—which they typically would not do when interacting with a human. Although some devices can be configured to stay active for a few seconds after a first interaction to avoid repeating the wakeword for immediate follow-ups, it is often difficult for the user to know that the device is still active. A second drawback is simply that the voice assistant is not aware of what is happening within the home or other environment between commands directed directly to the device. Although this is good for privacy it means an intelligent voice assistant such as one which can be implemented with an example of the present invention is unaware of what is happening in the home and may lack important context in order to help the family for example in accordance with the tenets.

A further two drawbacks are related to recognising the wakeword: wakeword recognition is done with statistical machine learning methods that are imperfect. This imperfection can manifest itself in two ways: the first is accidentally hearing a wakeword where none has actually been uttered: for example, a snippet of television sound, language that sounds similar or even a mention of the device that wasn't intended to wake it (e.g. talking about Alexa with a friend). In the case of an accidental firing a small amount of sound is unintentionally streamed out of the house anyway which has privacy consequences. The second way is the wakeword not being recognised even though a user said it. In this case the user will often have to repeat themselves until the device wakes up, which is frustrating for the user and increases the time needed to achieve the user's desired result.

Examples of voice assistants enabled by an example of the present invention can address these limitations by creating a private cloud environment for the family's data, where the private data used by the voice assistant is cryptographically isolated from the company that supplies the voice assistant and from other users. Unlike prior art voice assistants which are perceived as a single entity that is shared by everyone, some examples based on this private cloud method can also be perceived as a unique voice assistant that is exclusively for the use of the family/household and which knows and can be trusted with private family data and secrets.

According to various examples this is implemented using cryptographic methods where the key is in three parts and where any two of the three parts can access the private data. One of these keys is owned and held by the user and family and is held on local devices or stored within an associated smartphone application. The second key is held by the company that supplies the voice assistant and the third key is held by a separate entity—ideally a separate legal entity even in a separate legal jurisdiction. Routine operation of the voice assistant combines the key held by the user with that held by the supplier so the voice assistant using the private cloud can operate in normal day-to-day operation. However, this method would prevent any employee of the voice assistant supplier say from accessing private information as they would only have access to a single key. The relationship between the voice assistant supplier and the third entity is governed by a contract and set of procedures that strictly govern how and when they can collaborate in order to preserve the privacy of the end user and preserve their trust. Examples of when they might collaborate might be to restore a new third key to the end user in the event of the user losing access to their key and having had a request and reasonable evidence of this situation from the user. Another example might be limited circumstances following a court order or a criminal investigation. However, this arrangement would prevent casual access to the user's private data in most normal circumstances. In an alternative example the data is accessed with a single private key held only by the family optionally combined with methods to back-up and preserve the key from loss. There are multiple viable methods well known by practitioners of the relevant art for enabling combinations of keys to access data yet denying data to any single keyholder.

Voice assistant privacy and end user trust can be further preserved with additional privacy modes. Prior art voice assistants rely on a wake word as previously described, sometimes with a physical button that can permanently mute the device. Examples of the present invention can include an additional 'deep sleep' model which can be enabled by voice and from which an extended much longer or more unusual wake word is required to wake the device, eliminating the risk of a false accept from background noise or casual conversation mentioned above.

The privacy improvements from the private cloud method described herein also enables a 'join in' mode where the device is continuously listening and processing the conversation and potentially participating as appropriate. In some examples this 'join in' mode could even be the default and the voice assistant is in effect a family member who is fully present during family conversations.

Multiple Voice Assistants

According to various examples, this private voice assistant could be further customised by the user, possibly adjusting or augmenting the tenets it operates under, its personality, its name and its voice. In examples with a visual representation, this too can be customised. The result in a preferred example is that a family or person's voice assistant is conceptualised as a trusted, unique entity separate from every other voice assistant and in trusted possession of private data which it does not share with anyone else, even its supplier.

In various examples different assistants can communicate with each other to ask questions of private knowledge that the destination assistant knows, to make requests for actions that the remote assistant can do or to share information. When communication is with assistants that use UL those communications can be done using UL. For voice assistants not enabled by UL communication can be done in natural language.

The following concepts are provided.

Concept A: The Semantic Node

Method for the automated analysis or use of heterogeneous data, comprising the steps of:
  providing a structured representation of data that represents a universal language or corpus of natural language words, concepts, or other things, where the structured representation enables at least some aspects of the meaning or semantic content of those words, concepts or other things to be determined by a machine system;
  and in which the structured representation of a specific word, concept, or other thing is generatable locally by a user and, if shared with, or made available to, other users, automatically becomes a shared identifier for that specific word, concept, or other thing in the universal language or corpus.

Concept B. Tenets

Method for the automated analysis or use of heterogeneous data, comprising the steps of:
  providing a structured representation of data that can represent any natural language word, concept, or other thing such that at least some of the meaning or semantic content of that word, concept or other thing can be determined by a machine system;
  in which the structured representation of data includes one or more tenets, statements or other rules defining the objectives or motives for the machine system and the machine system is configured to operate at least partially by selecting or deciding on actions which autonomously optimize or otherwise affect its achievement or realization of those tenets, statements or other rules.

Concept C. Objective solver

A computer-implemented method including the steps of:
  (i) accessing stored data, or storing data, the stored data being in a language representing knowledge knowable by a human, wherein the stored data is stored in a representation which is machine readable and machine processable, and wherein the stored data is not stored solely in a human language;
  (ii) receiving and storing one or more statements of objectives, wherein the stored one or more statements of objectives are stored in the language representing knowledge knowable by a human;
  (iii) processing the stored one or more statements of objectives, and accessing and processing the stored data in a language representing knowledge knowable by a human, to derive a solution to the one or more statements of objectives, using the stored data in a language representing knowledge knowable by a human, and
  (iv) storing or outputting the solution.

Concept D. Crossword solver

Method for the automated analysis and solving of crossword puzzles, comprising the steps of:

providing a structured representation of data that can represent any natural language word, concept, or other thing such that the meaning or semantic content of that word, concept or other things can be determined by a machine system providing a structured representation of data that represents a natural language conclusion, inference or other logical process;

generating a structured representation of the clues in a crossword puzzle and the crossword grid;

a machine system autonomously using the structured representations of natural language words, concepts, or other things and the natural language conclusions, inferences or other logical processed to generate candidate answers to the clues.

The following sub-features may apply to any of the above Concepts A—D.

the heterogeneous data is sufficiently broad to render a schema impractical.

the heterogeneous data is not stored as a schema.

the heterogeneous data is not stored as natural language.

the universal corpus representing the meaning of natural language words includes all words in a dictionary.

the universal corpus of natural language concepts is derived from a machine analysis of natural language documents or conversations.

the universal corpus of natural language words, concepts or other things is derived from a machine analysis of natural language documents or conversations.

the structured representation of a word encodes the semantic meaning of that word through links to structured representations of related words, concepts, other terms, or logical processes.

the structured representation of a specific word, concept, or other thing is, once generated, a unique identifier for that specific word, concept, or other thing in the universal language or corpus.

there are multiple different structured representations of the same specific word, concept, or other thing, but each exists only locally and is not part of the universal language or corpus.

the unique identifier is a 128 bit UUID.

the structured representation of a specific word, concept, or other thing can relate to any of: every specific human being, the concept of human being (of which any specific human being is a member), every file, every web page, every audio recording or video, specific relationships (including the relationship that links any specific human being to the concept of human being), attributes, specific types of language nuance and every row and item in a relational database table.

the structured representation is a semantic node in an ordered or partially ordered combination or network of combined or linked nodes, the combined or linked nodes being the structured representation of the related words, concepts, other terms, or logical processes.

combining nodes generates a new word, concept, or other term with a new meaning or semantic content in the universal language.

an ordered or partially ordered collection of structured representations captures a specific meaning or semantic content.

a machine learning system generates new nodes and links between nodes by autonomously learning from natural language documents or conversations.

a structured representation represents a natural language conclusion, inference or other logical process.

structured representations of conclusions, inferences or other logical processes are used for reasoning and outputting the results of that reasoning.

the nodes of structured representations are used to constitute a memory or repository of knowledge or relationships between about words, concepts, other things, and conclusions, inferences or other logical processes.

the nodes of structured representations are used to understand spoken or written communication.

the node networks of structured representations are used to generate spoken or written communication.

the node networks of structured representations constitute a basis for a general intelligence system.

the representation of heterogeneous data is used in an application relating to managing health.

the representation of heterogeneous data is used in an application relating to managing nutrition.

the representation of heterogeneous data is used in an application relating to managing matching job seekers to jobs.

the representation heterogeneous data is used in an application relating to accounting.

the representation of heterogeneous data is used in an application relating to a voice assistant or chatbot.

the heterogeneous data is used in an application relating to searching the WWW.

Further aspects of an example of the present invention are described by the following clauses UL or Similar Powered System for Vertical Applications (1) A system operable to provide a useful vertical application where the useful vertical application requires data which is heterogeneous and extremely broad in scope, comprising at least one data store containing a machine-readable representation of the data that encodes meaning.

(2) The system described in clause 1 where the useful vertical application is an application operable to automatically match candidates to jobs or a health application or an accountancy application or a chatbot or a voice assistant.

(3) The system of clause 1 or clause 2 where the machine-readable representation of the data is a machine language comprising combinations of semantic nodes that represent entities and where meaning comes from the choice of semantic nodes and the way they are combined.

(4) The system of clause 3 where the system is further operable to receive a description of an entity from a remote system and use the description to return a semantic node corresponding to the entity.

(5) the system of any previous clause where the data includes a representation of computational capabilities that are available to the application.

(6) the system of any previous clause where the system is further operable to achieve automatic identification of data for removal from the data store.

(7) the system of any previous clause where the system is further operable to reason with reference to the contents of the at least one data store wherein new useful data is generated of use to the useful vertical application.

(8) the system of clause 7 where the new useful data is stored enabling the new useful data to be used in the future without further reasoning.

(9) the system of clause 6 where the automatic identification of data for removal from the data store is achieved using analysis of signals concerning the veracity or utility of the data from the application users.

Intelligent System Driven by Tenets (1) a system comprising at least one data store containing machine-readable tenets which represent goals and rules to guide the system and where the system is further operable to do actions that conform with the tenets by referencing the tenets.

(2) The system of clause 1 where the system is further operable to check potential actions against the tenets and determine the potential actions' conformity with the tenets.

(3) The system of clause 1 or 2 where the system is further operable to propose actions that conform to the tenets by referencing the tenets.

(4) The system of any previous clause where the actions include communicating with users in written form.

(5) the system of any previous clause where the actions include communicating with users in spoken form.

(6) the system of any previous clause where the tenets include at least one measure the system should try to maximize.

(7) the system of clause 6 where the at least one measure includes user happiness.

(8) the system of any previous clause where the tenets include at least one measure the system should try to minimize.

(9) the system of clause 8 where the at least one measure includes user unhappiness.

(10) the system of any previous clause where the tenets include at least one rule for actions the system must never do and where the system is further operable to avoid doing the actions the system must never do by referencing the tenets.

(11) the system of any previous clause where the tenets include at least one suggestion of what action to do in a defined circumstance.

(12) the system of any previous clause where the actions include accessing other remote computer systems.

(13) the system of any previous clause where the actions include changing the state of devices linked to the system via a network.

(14) the system of any previous clause where the actions include initiating a spoken interaction with a human being.

(15) the system of any previous clause where the system further comprises at least one data store containing a machine-readable representation of the world that encodes meaning and where the system is further operable to reason with reference to the machine-readable representation of the world to select actions that conform with the tenets.

(16) the system of clause 15 where the machine-readable representation of the world comprises a representation of valid reasoning steps and where the system is further operable to utilise the representation of valid reasoning steps to reason.

(17) the system of clause 15 or clause 16 where the machine-readable representation of the world includes a representation of computational capabilities that are available to the system and where the system is further operable to utilise the computational capabilities by referencing the machine-readable representation.

(18) The system of clause 15, 16 or 17 where the system is operable to learn and augment the machine-readable representation of the world.

(19) The system of clause 18 where the system is operable to learn from communication with at least one user.

(20) The system of clause 18 where the system is operable to learn from at least one external sensor connected to the system via a network.

(21) the system of any previous clause where the machine-readable tenets are at least partially represented by combinations of identifiers and where at least some of the identifiers represent concepts corresponding to real-world things.

(22) The system of clause 21 where the system is further operable to receive a description of a concept from a remote system and use the description to return an identifier which is likely to mean the concept.

(23) the system of any previous clause where the system is operable to continuously reason in a way that results in actions that conform with the tenets.

(24) the system of any previous clause where the system is operable to answer questions about the tenets from human users.

Intelligent system driven by tenets #2

(1) A computer system comprising a long-term memory; a short-term memory; a tenet-store containing machine-readable tenets representing rules to guide the system and where the computer system is operable to receive events and utilise the events, the contents of the long-term memory, the contents of the short-term memory and the tenets to do actions that conform with the tenets.

(2) The computer system of clause 1 where the events include communication from at least one user and where the actions include communication to at least one user.

(3) the computer system of any previous clause where the system is further operable to learn, and store what it has learned to the long-term memory.

(4) the computer system of any previous clause where the computer system is not operable to change the tenets.

(Extra Safe Examples:)

(5) the computer system of clause 4 where the tenets include a tenet prohibiting actions which might result in changes to the tenets.

(6) the computer system of any previous clause where the system is further operable to do an independent check of each potential action against the tenets and will discard the potential action if the independent check finds that it is incompatible with the tenets.

(7) the computer system of any previous clause which is further operable to actively exclude knowledge on itself from being used in determining actions.

Translation (1) A method of generating a machine-readable semantic representation of a section of natural language comprising passing the passage of natural language through a sequence-to-sequence neural architecture trained on training data comprising pairs of natural language and a corresponding structured representation that encodes meaning.

(2) The method of clause 1 where the neural architecture comprises an encoder and decoder and where the method comprises the further step of using beam searching during decoding of the semantic representations from the decoder to remove invalid semantic representations.

(3) The methods of clause 1 or 2 where the section of natural language is a question and where the method further comprises the step of answering the question with reference to the semantic representation.

(4) The methods of clause 1 or 2 where the section of natural language is one or more documents and where the method further comprises the steps of utilising the semantic representation of the one or more documents to answer questions.

(5) The methods of clause 3 or 4 where the method further comprises the step of reasoning with reference to the semantic representation to produce further representations not present prior to this step.

Job Matching Application (1) A system operable to match candidates to open jobs comprising at least one data store containing:

a plurality of candidate résumés where at least some parts of at least some of the candidate résumés are in a structured machine-readable form that encodes meaning;

a plurality of job specifications for open roles where at least some parts of at least some of the job specifications are stored in the structured machine-readable form that encodes meaning and where the system is further operable to match the plurality of candidate résumés with the plurality of job specifications to identify high confidence matches between candidates and open roles.

(2) the system of clause 1 where the structured machine-readable form is a language that represents meaning by creating combinations of identifiers and where at least some of the identifiers represent human skills and experience.

(3) the system of any previous clause where the at least one data store further stores a representation of candidates' desired roles at least partially represented in the structured machine-readable form and where the system is further operable to match open roles against the representation of candidates' desired roles in order to improve the matches between candidates and open roles.

(4) the system of any previous clause where the system is further operable to send a push notification to a mobile device when a high confidence match is found.

(5) the system of any previous clause where the system is further operable to explain how the candidate matches the role by generating an explanation of which bits of the job specification match the skills and experience of the candidate.

(6) the system of clause 5 where the explanation is in a natural language.

(7) the system of any previous clause where the system is operable to match requirements in job specifications to the skills and experience of a candidate where there are no keywords in common between the relevant parts of the natural language versions of the candidate résumé and job specification.

(8) the system of any previous clause where the system is operable to make a sequence of logical reasoning steps in order to match the skills or experience of a candidate with a requirement in a job specification.

Health Application (1) A system for managing a broad set of health data for one or more people where at least some of the health data is represented in a structured machine-readable form that encodes meaning stored within one or more data stores.

(2) The system of clause 1 where the health data includes nutrition data about food or drink that has been consumed by at least one of the one or more people.

(3) The system of clause 2 where the nutrition data includes data that represents the uncertainty about the volume or composition of what was consumed.

(4) The system of any previous clause where the health data comprises data about the results of blood tests or measurements or body composition or activity information or genetic data or microbiome data or bowel motion events or sleep data or workout data or activity data or symptoms of diseases or human moods or menstruation or ingestion of medication or medical conditions or data from any wearable device.

(5) the system of any previous clause where the system is further operable to converse with one or more users via text.

(6) the system of any previous clause where the system is further operable to enable selected other people to converse with the one or more users and to enable the selected other people to view relevant health data.

(7) the system of any previous clause where the system is further operable to create graphs of specific types of health data together wherein users can see how different data correlates.

(8) The system of any previous clause where the system is further operable to analyse the health data to uncover insights relevant to the specific user's health.

(9) The system of the previous clause where the insights include potential dietary intolerances or behaviours that influence sleep.

(10) The system of any previous clause where elements of the health data are combined to calculate an additional item of health data not already present in the health data.

(11) The system of clause 10 where the additional item of health data is an estimate of caffeine present in a user's body at a particular time.

Accounting Application (1) The system for managing accounting data for at least one business where at least some of the accounting data is represented in a structured machine-readable format that encodes real-world meaning stored within one or more data stores.

(2) The system of clause 1 where the structured machine-readable format is comprised of combinations of identifiers where at least some of the identifiers represent real-world entities relevant to the activities of the at least one business and where further meaning is encoded from the choice of combinations of the identifiers.

(3) The system of any previous clause where the system is operable to automatically present the accountancy data in a plurality of different accountancy standards.

(4) The system of any previous clause where the system is operable to answer questions about the activities of the at least one business.

Privacy-Enhanced Voice Assistant (1) A system provided by a system provider for providing services to at least one user via a voice user interface comprising at least one device local to the at least one user where the at least one device is operable to stream sound data to one or more remote data stores where the sound data is cryptographically stored within the one or more remote data stores using a cryptographic method where at least two of at least two different cryptographic keys are needed to read the sound data.

(2) The system of clause 1, where a first one of the at least two different cryptographic keys is held within the at least one device local to the user and where a second one of the at least two different cryptographic keys is held by the system provider.

(3) The system of clause 2, where the number of different cryptographic keys is at least three and where a third one of the different cryptographic keys is held by an entity distinct from both the user and the system provider.

(4) The system of any previous clause operable to stream general sound from the at least one device and to utilise information learned from the general sound to improve its value to the at least one user.

Enhanced Privacy Mode

A system with a voice user interface initiated with a first wakeword, where the system is operable to enter a privacy-preserving state requiring a second wakeword and where the second wakeword is sufficiently long or unusual that a false recognition of the second wakeword is significantly more improbable relative to the first wakeword Multiple Voice Assistant System (1) A system operable to deliver the experience of a plurality of different voice assistants to a plurality of users comprising at least one data store containing personality information which determines the personality of at least some of the plurality of different voice assistants.

(2) The system of clause 1, where the personality information includes information about the voice assistant's gender or name or voice or moods or emotional reactions or level of formality or position on the extrovert-introvert scale or position on any Myers Briggs scale or a Myers Briggs categorisation or categorisation in a personality test or visual appearance.

(3) The system of any previous clause where the at least one data store further comprises at least one set of machine-readable tenets which represent goals and rules to guide at least some of the plurality of voice assistants and where the system is further operable to do actions that conform with the tenets by referencing the tenets.

(4) The system of clause 3 where the at least one set of machine-readable tenets is a plurality of sets of machine-readable tenets and where selected ones of the plurality of different voice assistants are mapped to selected ones of the plurality of sets of machine-readable tenets wherein different voice assistants are driven by different tenets.

(5) The system of any previous clause where the at least one data store further comprises private user data accessed only by selected ones of the plurality of different voice assistants.

Example Use Cases

In examples, examples of the inventions may be used in the following applications:

- any language based man/machine interface spoken or in text form, where the machine user experience is expressed in UL.
- converting web pages into UL for search and analysis (e.g. in the limit, all web pages).
- converting all maps (especially ultra-high resolution maps needed for autonomous driving and related metadata) into UL.
- location based search against mapping data expressed in UL.
- identifying relevant adverts and news to serve someone based on their social media profile, expressed in UL.
- identifying relevant adverts and news to serve someone based on their web search and web browsing history, expressed in UL.
- suggesting potential friends or contacts based on similar social media or work profiles, expressed in UL.
- Identifying abusive postings, all converted into UL, on social media.
- Identifying messages and posts, all converted into UL, with national security or crime implications.
- analysing customer reviews and feedback, all converted into UL.
- analysing shopping requests, all converted into UL, to identify matching products against a product database expressed in UL.
- automated answering of questions from analysing web pages, all converted into UL.
- dating web sites based on matching profiles, converted into UL, or identifying other correlations that indicate compatibility.
- generating summaries, e.g. news summaries, from source documents converted into UL.

Note

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

APPENDIX 1

Key Concepts

This Appendix 1 summarises the key Concepts disclosed in this specification. We organise these key Concepts into the following 14 categories:

Concepts

A. Brackets to disambiguate combinations of nodes
B. Shared syntax across facts, queries and reasoning
C. Nesting of nodes
D. ID selection
E. Any client can generate a semantic node or passage
F. Consolidated universal language (UL) concepts
G. Question answering
H. Learning
I. Translation to and from UL
J. Semantic node resolution
K. Translation between natural languages
L. Voice Assistant
M. Tenets
N. Use cases:
   N1: Man/machine interface
   N2: Search and Analysis of Documents or web pages.
   N3. Mapping data represented as UL, associated systems utilising mapping data and location based search
   N4. Identifying relevant adverts and news
   N5. Aggregation and summarisation of news
   N6. Matching between people using UL
   N7. Identifying abusive or untrue postings in social media
   N8. Analysis of Customer Reviews
   N9. Shopping queries and product requests
   N.10 Job matching
   N.11 Horizontal Health Application
   N.12 Accounting
   N.13 Voice Assistants/Chatbots Note that any Concept A-N can be combined with any one or more other Concepts A-N and any Concept A-N can be combined with any one or more optional features from any one or more other Concepts A-N.

We define each of these Concepts as follows:

Machine-Readable Language: Semantic Nodes and Passages

A. Brackets to Disambiguate Combinations of Nodes

The UL model uses bracketed combinations of nodes as the sole or primary mechanism for representing unambiguous meaning yet still achieves enormous expressivity. This enables faster processing of UL compared to other methods where there is a proliferation of different disambiguation mechanisms. It also simplifies storage enabling faster search and access. It also makes it faster to write UL compared to other languages and hence scales adoption. It also reduces the complexity and thus makes feasible many of the applications of the technology.

We can generalise to:

A computer implemented method for the automated analysis or use of data, comprising the steps of:
(a) storing in a memory a structured, machine-readable representation of data that conforms to a machine-readable language, where the structured, machine-readable representation includes a single syntactical item to disambiguate the meaning of structured representations of data;
(b) automatically processing the structured, machine-readable representation for one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:
(a) store in a memory a structured, machine-readable representation of data that conforms to a machine-readable language, where the structured, machine-readable representation includes a single syntactical item to disambiguate meaning;
(b) automatically process the structured, machine-readable representation for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprising semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features the single syntactical item to disambiguate meaning is parentheses or brackets.

the single syntactical item to disambiguate meaning is the only syntactical item to disambiguate the meaning of different combinations of structured, machine-readable representation of data.

the single syntactical item to disambiguate the meaning of different combinations of structured, machine-readable representation of data is the primary syntactical item to disambiguate the meaning of the combination.

the single syntactical item to disambiguate meaning represents nesting of the structured, machine-readable representation of data.

the single syntactical item to disambiguate meaning represents nesting of semantic nodes and passages.

the single syntactical item to disambiguate meaning represents nesting of semantic nodes and passages to any arbitrary depth.

the single syntactical item to disambiguate meaning requires that semantic nodes and passages can only be combined in nested combinations.

the single syntactical item to disambiguate meaning allows for expressions to be nested indefinitely to allow a user to define a concept, coupled with contextual information about the concept, as a hierarchy of semantic nodes.

the single syntactical item to disambiguate meaning allows for a combination semantic nodes to contain any finite number of semantic nodes and the semantic nodes within them can also be combination nodes creating any level of nesting.

The syntax of the structured, machine-readable representation of data conforms or substantially conforms to the production grammar "<passage>::=<id>| <passage>::= (<passage><passage>*)" where "<passage>*" means zero or one or more further passages and where <id> is an identifier for a semantic node.

B. Shared Syntax Across Facts, Queries and Reasoning

The UL model uses a shared syntax that applies to semantic nodes and passages that represent factual statements, query statements and reasoning statements. This enables faster processing of UL compared to other methods where there is a proliferation of different syntaxes. It also makes it faster to write UL compared to other languages and hence scales adoption. It also simplifies storage enabling faster search and access. It also reduces the complexity and thus increases the feasibility of many of the applications of the invention.

We can generalise to:

A computer implemented method for the automated analysis or use of data, comprising the steps of:
(a) storing in a memory a structured, machine-readable representation of data that conforms to a machine-readable language, where the language has a syntax that is a single shared syntax that applies to passages that represent factual statements, query statements and reasoning statements;
(b) automatically processing the structured, machine-readable representation for one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:
(a) store in a memory a structured, machine-readable representation of data that conforms to a machine-readable language, where the language has a syntax that is a single shared syntax that applies to passages that represent factual statements, query statements and reasoning statements;
(b) automatically process the structured, machine-readable representation for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the syntax applies to all structured, machine-readable representations of data.

the syntax is a simple unambiguous syntax comprising nesting of structured, machine-readable representations of data.

the syntax is a simple unambiguous syntax comprising nesting of structured, machine-readable representations of data to any arbitrary depth.

the syntax is a simple unambiguous syntax in which structured, machine-readable representations of data can only be combined in nested combinations.

the syntax allows for expressions to be nested indefinitely to allow a user to define a concept, coupled with contextual information about the concept, as a hierarchy of semantic structured, machine-readable representations of data.

Combinations of structured, machine-readable representations of data can contain any finite numbers of structured, machine-readable representations of data creating any level of nesting.

structured, machine-readable representations of data are semantic nodes or passages.

semantic nodes are identified with a UUID.

C. Nesting of Nodes

The UL model uses an unambiguous syntax comprising nesting of semantic nodes and passages, i.e. the structured, machine-readable representations of data. This lack of ambiguity enables machines to process and utilise data stored in this model with certainty as to what is being represented in contrast to the use of a natural language.

We can generalise further to:

A computer implemented method for the automated analysis or use of data, comprising the steps of:

(a) storing in a memory a structured, machine-readable representation of data that conforms to a machine-readable language, where the syntax for the machine-readable language is a substantially unambiguous syntax comprising nesting of structured, machine-readable representations of data;

(b) automatically processing the structured, machine-readable representation one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:

(a) store in a memory a structured, machine-readable representation of data that conforms to a machine-readable language, where the language has a syntax in which the syntax for the machine-readable language is a substantially unambiguous syntax comprising nesting of structured, machine-readable representations of data;

(b) automatically process the structured, machine-readable representation for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages; and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the syntax is a simple unambiguous syntax comprising nesting of structured, machine-readable representations of data to any arbitrary depth.

the syntax is a simple unambiguous syntax in which structured, machine-readable representations of data can only be combined in nested combinations.

the syntax allows for expressions to be nested indefinitely to allow a user to define a concept, coupled with contextual information about the concept, as a hierarchy of semantic structured, machine-readable representations of data.

Combinations of structured, machine-readable representations of data can contain any finite numbers of structured, machine-readable representations of data creating any level of nesting.

structured, machine-readable representations of data are semantic nodes or passages.

semantic nodes are identified with a UUID

D. ID Selection

The UL model uses semantic node identifiers that are selected from an address space that is sufficiently large to enable users to select a new identifier with negligible risk of selecting a previously allocated identifier. This enables users to use the present invention with local data without having to coordinate with any other user, whilst also benefitting from shared nodes which have meaning to more than one user.

We can generalise to:

A computer implemented method for the automated analysis or use of data, comprising the steps of:

(a) storing in a memory a structured, machine-readable representation of data that conforms to a machine-readable language, where the structured, machine-readable representation of data comprises a plurality of identifiers which are selected from an address space that is sufficiently large to enable users to select a new identifier with negligible risk of selecting a previously allocated identifier;

(b) automatically processing the structured, machine-readable representation one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:

(a) store in a memory a structured, machine-readable representation of data that conforms to a machine-readable language, where the structured, machine-readable representation of data comprises a plurality of identifiers which are selected from an address space that is sufficiently large to enable client entities to select a new identifier with negligible risk of selecting a previously allocated identifier;

(b) automatically process the structured, machine-readable representation for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

A semantic node once defined has an identifier or ID.

The identifier is selected from an address space that is sufficiently large to enable client entities to select new identifiers independently of other client entities without duplication.

The identifier is selected from an address space that is sufficiently large to enable client entities to select a new identifier with negligible risk of selecting a previously allocated identifier.

the identifier or ID is a UUID.

the ID is a 128-bit version 4 UUID (RFC 4122) with hyphenated lower-case syntax.

the ID is a UUID or a string, such as a Unicode string.

a string can denote itself as a structured, machine-readable representation of data and its meaning is strictly the string itself only and any natural language meaning contained within the string is not part of the meaning of the string.

a string is represented by an ID as an additional identifier.

a string is represented as a UUID or other numerical ID and a separate passage links the string to that numerical ID to provide its meaning.

two identical strings used as structured, machine-readable representations of data have universal meaning as that string.

any user can coin its own structured, machine-readable representation of data with its own local meaning by picking an unused identifier.

any user can coin its own identifier for a semantic node even if another identifier is already used for the semantic node.

any user is free to define its own meaning to combinations of structured, machine-readable representations of data.

there can be multiple different structured, machine-readable representation of data for the same specific word, concept, or other thing.

any user that chooses to create passages that use shared structured, machine-readable representation of data is also expressing the same meaning by combining them, so that the meaning that comes from combining shared structured, machine-readable representations of data is universal.

each sense of each word in a dictionary is represented by a structured, machine-readable representation of data.

a "shared ID" is an ID used by more than one user; a "private ID" or "local ID" is similarly an ID used by only one user and is not published or exposed to other users; a "public ID" is an ID that a user has used in UL that can be seen by every user.

a semantic node is a structured, machine-readable representation of data that, once defined, has an identifier so it can be referred to within the machine-readable language.

a passage is a combination of semantic nodes expressing meaning, and is the sole nesting construct.

semantic nodes in infinite classes can be represented as a combination of a plurality of other nodes.

E. Any Client can Generate a Semantic Node or Passage

The UL model uses semantic node identifiers that are selected from an address space that is sufficiently large to enable users to select a new identifier with negligible risk of selecting a previously allocated identifier. This makes it faster and easier to create UL compared to other languages and hence scales adoption. It also enables users to apply the technology to their local data while still benefitting from passages and implementations generated by other users.

We can generalise to:

A computer implemented method for the automated analysis or use of data, comprising the steps of:

(a) storing in a memory a structured, machine-readable representation of data that conforms to a machine-readable language, and in which the machine-readable language is scalable since there are no restrictions on which users can create a structured, machine-readable representation of data or related identifier;

(b) automatically processing the structured, machine-readable representation one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:

(a) store in a memory a structured, machine-readable representation of data that conforms to a machine-readable language, and in which the machine-readable language is scalable since there are no restrictions on which users can create a structured, machine-readable representation of data or related identifier;

(b) automatically process the structured, machine-readable representation for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the machine-readable language is a universal language for which substantially anything expressible in natural language is expressible as a structured, machine-readable representation of data or a combination of structured, machine-readable representations of data.

a structured, machine-readable representation of data represents a specific entity, such as a word, concept, or other thing, and once generated, identifies uniquely that specific word, concept, or other thing in the universal language.

an ordered or partially ordered collection of structured, machine-readable representations of data captures a specific meaning or semantic content.

the meaning of a structured, machine-readable representation of data comes from statements written in the machine-readable language.

the meaning of a structured, machine-readable representation of data comes from other structured, machine-readable representations of data that represents things that have been said about the structured, machine-readable representation of data.

a semantic node that represents an entity encodes the semantic meaning of that entity through links to structured, machine-readable representations of data of related words, concepts, other terms, or logical processes.

combining structured, machine-readable representations of data generates a new word, concept, or other term with a new meaning or semantic content in the machine-readable language.

the machine-readable language is understandable to human users where it corresponds to an equivalent statement in natural language.

the machine-readable language is scalable since any natural language word, concept, or other thing can be represented by a structured, machine-readable representation of data.

the machine-readable language is scalable since there are no restrictions on which users can create a structured, machine-readable representation of data.

a semantic node is a structured, machine-readable representation of data that, once defined, has an identifier so it can be referred to within the machine-readable language.

a passage is a combination of semantic nodes expressing meaning, and is the sole nesting construct.

F. Consolidated UL Concepts

We can bring the above concepts together as follows:

A computer implemented method for the automated analysis or use of data, comprising the steps of:

(a) storing in a memory structured, machine-readable representations of data that conform to a machine-readable language in which one or more of the following apply:

a single syntactical item is used to disambiguate the meaning of structured representations of data;

the syntax for the machine-readable language is a single shared syntax that applies to passages that represent factual statements, query statements and reasoning statements;

the syntax for the machine-readable language is a substantially unambiguous syntax comprising nesting of structured representations of data;

a structured representation of data includes an identifier selected from an address space that is sufficiently large to enable users to select a new identifier with negligible risk of selecting a previously allocated identifier;

the machine-readable language is scalable since there are no restrictions on which users can create a structured representations of data or related identifier;

(b) automatically processing the structured representations of data for one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:

(a) store in a memory or access from a memory a structured, machine-readable representation of data that conforms to a machine-readable language comprising semantic nodes and passages in which one or more of the following apply:

a single syntactical item is used to disambiguate the meaning of structured representations of data;

the syntax for the machine-readable language is a single shared syntax that applies to passages that represent factual statements, query statements and reasoning statements;

the syntax for the machine-readable language is a substantially unambiguous syntax comprising nesting of structured representations of data;

a structured representation of data includes an identifier selected from an address space that is sufficiently large to enable users to select a new identifier with negligible risk of selecting a previously allocated identifier;

the machine-readable language is scalable since there are no restrictions on which users can create a structured representations of data or related identifier;

(b) automatically process the structured representations of data for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

G. Question Answering

The UL model enables automated answering of questions: a question is represented by passages or combinations of semantic nodes and an answer can be automatically generated by three different processes: matching the question with passages previously stored in a passage memory store; (ii) fetching and executing one or more computation units, where computation units represent computational capabilities relevant to answering the question; (iii) fetching and execution of one or more reasoning passages, which represent the semantics of potentially applicable reasoning steps relevant to answering the question. This approach makes highly-scalable, rapid, accurate, semantically based question answering possible. The questions can come from machines; or from human users after translating the natural language question into UL and the response back into natural language. We can generalise as follows:

A computer implemented method for the automated analysis or use of data, comprising the steps of:

(a) storing in a memory a structured, machine-readable representation of data that conforms to a machine-readable language, and in which a question is represented in the memory as a structured, machine-readable representation of data; and (b) automatically generating a response to the question, using one or more of the following steps: (i) matching the question with structured, machine-readable representations of data previously stored in a memory store; (ii) fetching and executing one or more computation units, where computation units represent computational capabilities relevant to answering the question; (iii) fetching and execution of one or more reasoning passages, which are structured, machine-readable representations of data that represent the semantics of potentially applicable reasoning steps relevant to answering the question;

and in which the representation of the question, the structured, machine-readable representations of data previously stored in the memory store, the computation units and the reasoning passages are all represented in substantially the same machine-readable language.

Computer-based system configured to analyse data, the system being configured to:

(a) store in a memory a structured, machine-readable representation of data that conforms to a machine-readable language, and in which a question is represented in the memory as a structured, machine-readable representation of data; and (b) automatically generate a response to the question, using one or more of the following steps: (i) matching the question with structured, machine-readable representations of data previously stored in a memory store; (ii) fetching and executing one or more computation units, where computation units represent computational capabilities relevant to answering the question; (iii) fetching and execution of one or more reasoning passages, which are structured, machine-readable representations of data that represent the semantics of potentially applicable reasoning steps relevant to answering the question and in which the representation of the question, the structured, machine-readable representations of data previously stored in the memory store, the computation units and the reasoning passages are all represented in substantially the same machine-readable language.

In the preferred implementation, the structured, machine-readable representation of data conforms to a machine-readable language that comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

Reasoning reasoning is done with a series of one or more queries being answered to see if the reasoning step is valid.

reasoning is done with a series of one or more queries being answered to generate results needed for the result of the reasoning.

passages represent details for the computation unit that are needed to select and run the computation unit, namely defining what it can do, how to run it and how to interpret the results.

The step of fetching and execution of one or more initial reasoning passages returns other passages with unknowns that need to be processed, and the results of that processing is a tree of connection that is used to give results for the initial passage.

The tree of connection is stored and the processing of these other passages with unknowns happens in parallel, allowing data fetching and exploration of reasoning to be parallelized.

once all passages are processed up to a given maximum reasoning depth, a second non-parallelised step is used to walk through this tree of processed passages and unknowns mappings to find valid answers.

each passage in a list of passages is processed to identify valid mappings from the passage memory store and the computation units, where a valid mapping for that list of passages is one where all unknowns have a value and there are no contradicting mappings between passages in the list.

The step of identifying valid mappings recursively looks through the data and finds all valid mappings for the initial question which can be returned as the answer.

at least some of the passages that have been generated from reasoning or computation are stored in the passage memory store, making these available in the future for faster processing.

The history of these generated passages is also stored so that changes to a trust level in the passages that were used to generate them can be extended to the trust given to these generated passages.

The history of these generated passages is also stored to enable the removal of generated passages when the trusted status of one or more of the passages used to generate them changes.

When a new passage is added to the passage memory store it is assigned a low initial trust value when added by a normal user and a higher starting value when added by a privileged user.

Questions are represented in the machine-readable language with a passage which comprises a node identifying the passage as a question, language representing zero or one or more unknown entities being requested within the semantics of the question and language representing the semantics of the question and referencing the zero or one or more unknown entities.

Questions are represented in the machine-readable language with a passage of the form ((Question <unknowns>)(<passage>)) where Question is a semantic node and <unknowns> is a list of zero or one or more semantic nodes representing unknown values (similar in meaning to letters of the alphabet in algebra) and where <passage> is where the unknowns are used to express what is being asked.

a signal from an application of the system or method is stored in association with the passages utilised by the application in order to keep track of the value of the passages passages are assigned a vector of values where the number at each index represents a different quality of the passage.

the different qualities include veracity, usefulness, and efficiency.

a process that uses the passages utilises a priorities vector with numbers at each index that indicate how much they prioritise that value.

the overall value of the passage to that process can then be obtained from the dot product of the vectors.

a reasoning engine experiments with high and lower value passages to answer the question and the answers provided by the reasoning engine are then monitored for any signals that would indicate whether the lower value passages have a positive or negative effect on the answers and this information then feeds back into an auto-curation process which re-evaluates the value of the passage with the new signal.

an auto-curation process automatically tests passages to determine if they should be used for question-answering.

the structured, machine-readable representations of data previously stored in a memory store have been curated with an automatic method.

the question is the result of translating natural language asked by a user into a substantially semantically-equivalent representation in the machine-readable language.

the response to the question is subsequently translated into semantically equivalent natural language and presented to one or more users.

the question is the result of translating a question spoken by a user in a natural language into a substantially semantically-equivalent representation in the machine-readable language and the user is subsequently played a spoken answer where the spoken answer is the result of translating the response to the question into the natural language.

H. Learning

The UL model enables automated learning. Things which are learned can be stored in UL and are then available for reasoning, question answering and the other uses and applications of UL described herein. The results of this learning contrast with statistical machine-learning where (say) billions of weights in a very large neural net are adjusted, as what has been learned is understood, can be explained to human users and can be reasoned with. We can generalise as follows:

A computer implemented method for the automated analysis or use of data, comprising the steps of:
(a) learning new information and representing the new information in a structured, machine-readable representation of data that conforms to a machine-readable language;
(b) storing the structured machine-readable representation of data in a memory and automatically processing the structured representations of data for one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:
a) learn new information and representing the new information in a structured, machine-readable representation of data that conforms to a machine-readable language;
(b) store the structured machine-readable representation of data in a memory and automatically processing the structured representations of data for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

Learning the new information is obtained from automatically processing the structured, machine-readable representation of data to obtain, or learn, new information, and the new information is itself represented as structured, machine-readable representations of data that are stored in memory.

Learning new information is obtained from a machine-learning system which generates classifications or predictions or other outputs which are represented in the structured, machine-readable representation of data a machine-learning system processes the semantic nodes and passages to obtain, or learn, new information.

new information is generated by automatically processing the semantic nodes and passages to answer a question.

a question is represented as one or more passages and a response to the question is automatically generated using one or more of the following steps: (i) matching the question with passages previously stored in a passage memory store; (ii) fetching and executing one or more computation units, where computation units represent computational capabilities relevant to answering the question; (iii) fetching and execution of one or more reasoning passages, which are passages that represent the semantics of potentially applicable reasoning steps relevant to answering the question.

the new information represented as semantic nodes or passages are stored and used to improve performance of learning new facts.

the new information represented as semantic nodes or passages are stored and used to improve reasoning steps.

the new information represented as semantic nodes or passages are stored and used to explain or describe the new information in natural language.

the new information represented as semantic nodes or passages are stored and used in text or spoken conversations with human users.

learning new information takes place from conversation with or other natural language provided by human users, in which natural language provided by users in spoken or written form is translated into semantic nodes and passages and then new information represented by these semantic nodes and passages is stored and used.

learning takes place from reasoning, in which semantic nodes and passages that are generated from a chain of reasoning steps, are stored and utilised.

learning takes place from natural language, in which by translating all or parts of document sources of natural language, such as web pages, scientific papers or other articles into semantic nodes or passages, the resulting semantic nodes or passages are then utilised by applications.

non-document sources of natural language, including audio recordings or videos containing human speech, are used and speech recognition technology is first utilised to create a text transcription of the recordings of voice which are then translated into semantic nodes and passages.

a machine learning system is used to analyse document and non-document data and create passages from that data.

a neural net is trained end-to-end to turn audio or video data directly into semantic nodes and passages.

natural language-based learning is combined with statistical machine-learning to optimise the translation of document and non-document data into semantic nodes and passages.

a machine learning system is used to generate the semantic nodes or passages.

the machine learning system is a neural network system, such as a deep learning system.

the machine learning system has been trained on training data comprising natural language and a corresponding structured machine-readable representation, such as a machine-readable language comprising semantic nodes and passages a passage of natural language is passed through a sequence-to-sequence neural architecture trained on training data comprising natural language and a corresponding structured representation that encodes meaning.

the neural network system is a switch transformer feed forward neural network system.

the neural architecture comprises an encoder and decoder and beam searching is used during decoding of the semantic representations from the decoder to remove invalid semantic representations.

structured data, such as the content of a table found in a document or on the web, a spreadsheet or the content of a relational, graph or other database is turned into semantic nodes and passages by assigning semantic nodes to the identifiers in the structured data and writing semantic nodes and passages that correspond to the meaning of the structured data.

learning takes place from analysis of other data, in which the data is processed with an algorithm and the results of that processing is represented in semantic nodes and passages.

I. Translation to and from UL

Natural language input is translated into UL: this enables the UL system to understand that natural language input: once translated into UL the meaning in the original natural language is available to the machine. When big deep-learning systems translate between natural languages there is a belief in the ML community that the representation in the neural net after the original sentence is "encoded" corresponds to the meaning of the language in some way as evidenced by the convincing translation produced in the target language. However that internal encoding is incomprehensible (it is a very big tensor or tensors of weights) and cannot be used for anything other than generating the translation (which is natural language again so not that useful to a machine). Accessing the true meaning of documents is one of the big unsolved frontiers of AI. Translation to and from UL also enables spoken or written man-machine interaction with examples of the present invention.

More generally:

A computer implemented method for the automated analysis or use of data, comprising the steps of:
(a) storing in memory a structured machine-readable representation of data that conforms to a machine-readable language;
(b) receiving a word or sequence of words in a natural language;
(c) automatically translating that word or sequence of words into the machine-readable language by identifying or generating structured machine-readable representations that semantically represent the meaning of the word or sequence of words.

Computer-based system configured to analyse data, the system being configured to:
(a) store in memory a structured machine-readable representation of data that conforms to a machine-readable language;
(b) receive a word or sequence of words in a natural language;
(c) automatically translate that word or sequence of words into the machine-readable language by identifying or generating structured machine-readable representations that semantically represent the meaning of the represent that word or sequence of words.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

a machine learning system is used to generate the semantic nodes or passages that represent the words or sequence of words in a natural language.

the machine learning system is a neural network system, such as a deep learning system.

a neural architecture is used to generate the machine-readable language.

the neural architecture utilises recurrent neural networks or LSTMs or attention mechanisms or transformers.

the machine learning system has been trained on training data comprising natural language and a corresponding structured machine-readable representation, such as a machine-readable language comprising semantic nodes and passages.

a passage of natural language is passed through a sequence-to-sequence neural architecture trained on training data comprising natural language and a corresponding structured representation that encodes meaning.

the neural network system is a switch transformer feed forward neural network system.

the neural architecture comprises an encoder and decoder and beam searching is used during decoding of the semantic representations from the decoder to remove invalid semantic representations.

the word or sequence of words in a natural language is a question and the question is answered with reference to the semantic representation.

the word or sequence of words in a natural language is one or more documents and the semantic representation of the one or more documents is used to answer question.

reasoning with reference to the semantic representation produces further, new representations.

when automatically translating a sequence of words expressed in the natural language into the machine-readable language, the structure of the sequence of words is compared with known machine-readable language structures in the memory to identify similarities.

automatically translating the word or sequence of words into the machine-readable language is achieved by referencing a store of previously identified correct translations between the natural language and the machine-readable language.

automatically translating the word or sequence of words into the machine-readable language is achieved by utilising a pipeline of functions which transform the word or sequence of words into a series of intermediate forms.

the semantic impact of changes to the word or sequence of words in a natural language is automatically assessed to determine whether known or ground truth examples of semantic nodes or passages can be used that are sufficient accurate.

the semantic nodes or passages that represent the words or sequence of words provides a machine-readable representation of the meaning of the words or sequence of words.

the semantic nodes or passages that represent the words or sequence of words are processed by a computer-based system for one or more of the following: to derive facts or relationships, to reason, to learn, to translate, to answer questions, to process natural language content, to enable man-machine interaction, to represent and to police rules or tenets, to enable one or more vertical applications.

the semantic nodes or passages that represent the words or sequence of words are processed by a computer-based system to generate an output that is human-readable.

the human readable output include one or more of the following: an answer to a question expressed in the natural language; a reasoning statement that explains how the system has reached a conclusion; a learning statement that explains what the system has learnt; a response in a man/machine interaction.

The system is further operable to automatically translate from the structured-machine readable representation to the natural language.

When translating from the structured-machine readable representation to the natural language the system varies the generated translations between alternatives that are substantially semantically equivalent to create varied and fresh responses for the benefit of human users.

Automatically translating the word or sequence of words into the machine-readable language is achieved by referencing a context of information relevant to generating a correct translation.

J. Semantic Node Resolution

The UL model makes it fast and efficient to create consistent semantic nodes and passages: when a user wishes to use a shared, public identifier for an entity, it sends a description of that entity to a service, which then returns the appropriate shared, public identifier if it exists and can be identified—if not the user can use a new identifier. This enables users to translate existing data into UL very easily while taking advantage of shared information and then use that representation for the purposes and applications described herein.

More generally:

A computer implemented method for the automated analysis or use of data, comprising the steps of:
(a) storing in a memory a structured, machine-readable representation of data that conforms to a machine-readable language;
(b) providing a service operable to receive a description of an entity and return one or more identifiers for structured, machine-readable representations of data corresponding to the entity, so that a user is able to use a shared identifier for the entity.

Computer-based system configured to analyse data, the system being configured to:
(a) store in a memory a structured, machine-readable representation of data that conforms to a machine-readable language;
(b) provide a service operable to receive a description of an entity and return one or more identifiers for structured, machine-readable representations of data corresponding to the entity, so that a user is able to use a shared identifier for the entity.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes and where machine-readable meaning comes from the choice of semantic nodes and the way they are combined and ordered as passages.

Other optional features:

the description is partially or fully described in the machine-readable language.

the description is partially or fully written in one or more natural languages.

the service compares the description of the proposed semantic node or passages with available information about existing entities to determine if there is a match.

the service probabilistically determines if there is a match.

the service additionally returns probabilities of matches along with the one or more identifiers.

the service returns a new identifier if no match is found.

K. Translating Between Different Natural Languages

As the UL representation is intended to fully represent the meaning of natural language it was translated from, even potentially representing nuance or properties like level of formality, it is an advantage to use UL as a kind of natural-language-independent semantic intermediate language before translating from it into the target language. This enables accurate, semantically based translation and greatly reduces the number of translation systems or models needed to translate between a large number of pairs of natural languages as only one translation system or model is needed per natural language.

More generally:

A computer implemented method for translating between languages, comprising the steps of:
(a) storing in a memory a structured, machine-readable representation of data that conforms to a machine-readable language;
(b) receiving a word or sequence of words in the first natural language to be translated into the second natural language;
(c) automatically translating that word or sequence of words expressed in the first natural language into the second natural language by (i) identifying a structured, machine-readable representation of data that represents the semantics of the word or sequence of words in the first natural language and (ii) retrieving a word or sequence of words in the second natural language that corresponds in meaning to the identified structured, machine-readable representation of data.

Computer-based system configured to translate between languages, the system being configured to:
(a) store in a memory a structured, machine-readable representation of data that conforms to a machine-readable language;
(b) receive a word or sequence of words in the first natural language to be translated into the second natural language;
(c) automatically translate that word or sequence of words expressed in the first natural language into the second natural language by (i) identifying a structured, machine-readable representations of data that represents the semantics of the word or sequence of words in the first natural language and (ii) retrieve a word or sequence of words in the second language that corresponds in meaning to the identified structured, machine-readable representation of data.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:
a machine learning system is used to generate semantic nodes or passages corresponding to or from words or sequence of words in a natural language.
the machine learning system is a neural network system, such as a deep learning system.
the machine learning system has been trained on training data comprising natural language and a corresponding structured machine-readable representation, such as a machine-readable language comprising semantic nodes and passages.
a passage of natural language is passed through a sequence-to-sequence neural architecture trained on training data comprising natural language and a corresponding structured representation that encodes meaning.
the neural network system utilises recurrent neural networks or LSTMs or attention mechanisms or transformers.
the neural network system is a switch transformer feed forward neural network system.
the neural architecture comprises an encoder and decoder and beam searching is used during decoding of the semantic representations from the decoder to remove invalid semantic representations.
the semantic impact of changes to the word or sequence of words in the first natural is automatically assessed to determine whether known or ground truth examples of semantic nodes or passages can be used that are sufficient accurate.
the word or sequence of words in the second language that correspond to the identified semantic nodes or passages are automatically varied to provide for varied translations.

L. Voice Assistant

UL enables an always-on voice assistant that is able to discern meaning from inputs (e.g. spoken commands or questions) and generate semantically meaningful responses, without the need for a 'wake word'.

We can generalise to:
A computer implemented method for the automated analysis or use of data, comprising the steps of:
(a) storing in a memory a structured, machine-readable representation of data that conforms to a machine-readable language;
(b) automatically and autonomously processing detected audio or text into the structured representation of data for one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:
(a) store in a memory a structured, machine-readable representation of data that conforms to a machine-readable language;
(b) automatically and autonomously process detected audio or text into the structured representation of data for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:
autonomous processing of audio or text takes place whenever audio or text is detected or received.
system is continuously receptive to input audio or text.
system does not have a wakeword or can operate in a mode where there is no wakeword.
autonomous processing of detected audio or text takes place without any external trigger event to initiate processing, such as a wake word, or user instruction or action to initiate processing.
detected audio or text is a question from a user and the question is automatically processed and an answer automatically generated and provided to the user.
detected audio or text is a statement from a user and the statement is automatically processed and a response, such as a conversational response, automatically generated and provided to the user.
detected audio or text is a request from a user for an action to take place, and the request is automatically processed and the action executed.
detected audio or text is a request from a user for an action to take place, and the request is automatically processed and the action executed if doing so optimizes or otherwise positively affects the achievement or realization of tenets, statements or other rules.
Detected audio or text is cryptographically isolated from the provider of the system whereby private information cannot be accessed by the provider of the system.

detected audio or text is cryptographically stored using a cryptographic method where at least two of at least two different cryptographic keys are needed to read the detected audio or text.

detected audio or text comes from a device local to a user and a first one of the at least two different cryptographic keys is associated with the device local to the user and where a second one of the at least two different cryptographic keys is held by the system provider.

the number of different cryptographic keys is at least three and a third one of the different cryptographic keys is held by an entity distinct from both the user and the system provider Multiple voice assistants are provided, such as a unique one per family.

the system is operable to deliver the experience of a plurality of different voice assistants to a plurality of users comprising at least one data store containing personality information which determines the personality of at least some of the plurality of different voice assistants.

the personality information includes information about the voice assistant's gender or name or voice or moods or emotional reactions or level of formality or position on the extrovert-introvert scale or position on any Myers Briggs scale or a Myers Briggs categorisation or categorisation in a personality test or visual appearance.

M. Tenets

UL enables objectives (e.g. maximise client happiness, do not break the law) to be captured in machine-understandable form: these are 'tenets' and they enable the system to determine actions and to determine whether or not to execute a candidate action by determining if doing so would optimise the tenet, or violate the tenet. It provides the machine with the ability to act in a moral or ethical manner and to determine its own behaviour rather than having everything it does determined by pre-written computer code. This enables scaling of the capabilities of the system as the system learns without the addition and debugging of new program code. It also enables consistent changes or variations in the behaviour or product rules of the system to be made very quickly without any code being changed.

We can generalise to:

A computer implemented method for the automated analysis or use of data, comprising the steps of:
(a) storing in a memory a structured, machine-readable representation of data that conforms to a machine-readable language;
in which the structured representation of data includes one or more tenets, statements or other rules defining the objectives or motives, also represented using the structured representation of data;
(b) analysing a potential action to determine whether executing the action would optimize or otherwise affect achievement or realization of those tenets, statements or other rules;
(c) automatically selecting, deciding on or executing actions only if they optimize or otherwise positively affect the achievement or realization of those tenets, statements or other rules.

Computer-based system configured to analyse data, the system being configured to:
(a) store in a memory a structured, machine-readable representation of data that conforms to a machine-readable language;
in which the structured representation of data includes one or more tenets, statements or other rules defining the objectives or motives, also represented using the structured representation of data;
(b) analyse a potential action to determine whether executing the action would optimize or otherwise affect achievement or realization of those tenets, statements or other rules;
(c) automatically select, decide on or execute actions only if they optimize or otherwise positively affect the achievement or realization of those tenets, statements or other rules.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

actions that conform to the tenets, statements or other rules ('tenets') are automatically proposed by referencing the tenets.

the actions include communicating with users in written form.

actions include communicating with users in spoken form.

the tenets include at least one measure the system should try to maximise, such as user happiness.

the tenets include at least one measure the system should try to minimise, such as user unhappiness.

the tenets include at least one rule for actions the system must never do.

the system is further operable to avoid doing the actions the system must never do by referencing the tenets.

the tenets include at least one suggestion of what action to do in a defined circumstance.

the tenets include sub-tenets which are tenets that relate to other tenets or which are more specific examples of another tenet.

the actions include accessing other remote computer systems.

the actions include changing the state of devices linked to the system via a network.

the actions include initiating a spoken interaction with a human being.

a data store contains a machine-readable representation of the world that encodes meaning and where the system is further operable to reason with reference to the machine-readable representation of the world to select actions that conform with the tenets.

the machine-readable representation of the world comprises a representation of valid reasoning steps and where the system is further operable to utilise the representation of valid reasoning steps to reason.

the machine-readable representation of the world includes a representation of computational capabilities that are available to the system and where the system is further operable to utilise the computational capabilities by referencing the machine-readable representation.

the system is operable to learn and augment the machine-readable representation of the world.

the system is operable to learn from communication with at least one user.

the system is operable to learn from at least one external sensor connected to the system via a network.

the machine-readable tenets are at least partially represented by combinations of identifiers and where at least some of the identifiers represent concepts corresponding to real-world things.

the system is further operable to receive a description of a concept from a remote system and use the description to return an identifier which is likely to mean the concept.

the system is operable to continuously reason in a way that results in actions that conform with the tenets.

the system is operable to answer questions about the tenets from human users.

the computer system comprises a long-term memory; a short-term memory; a tenet-store containing machine-readable tenets representing rules to guide the system and where the computer system is operable to receive events and utilise the events, the contents of the long-term memory, the contents of the short-term memory and the tenets to do actions that conform with the tenets.

the computer system comprises a component which generates candidate actions; a component that decides whether to execute the candidate actions with reference to the tenets and a component which executes actions.

answering a question asked by a human user comprises two actions—generating a response to the question and communicating that response to the human user.

the events include communication from at least one user and where the actions include communication to at least one user.

the system is further operable to learn, and store what is has learned to the long-term memory.

the computer system is not operable to change the tenets.

the tenets include a tenet prohibiting actions which might result in changes to the tenets.

the system is further operable to do an independent check of each potential action against the tenets and will discard the potential action if the independent check finds that it is incompatible with the tenets.

the computer system is further operable to actively exclude knowledge on itself from being used in determining actions.

Contemplation Engine potential actions are autonomously generated by the computer based system.

potential actions are autonomously generated by the computer based system as outputs from processing inputs, such as audio or text.

potential actions are autonomously generated with a process that operates substantially continuously.

potential actions are autonomously generated without any external trigger event to initiate processing or user instruction or action to initiate processing.

the potential actions are automatically executed if they optimize or otherwise positively affect the achievement or realization of those tenets, statements or other rules.

Use Cases

N1: Man/Machine Interface

UL can be used as part of a human/machine interface, where the machine is able to interpret semantically inputs that are spoken, written or GUI instruction provided by a human and hence enable an improved user experience.

We can generalise to:

A computer implemented method for the automated analysis or use of data, comprising the steps of:

(a) storing in a memory a structured, machine-readable representation of data that conforms to a machine-readable language; the structured representation of data including a representation of a spoken, written or GUI instruction provided by a human to a human/machine interface;

(b) automatically processing the structured representation of data for one or more of the following: to derive facts or relationships, to reason, to learn, to translate, to answer questions, to process natural language content, to enable man-machine interaction, to represent and to police rules or tenets, to enable one or more vertical applications.

Computer-based system configured to analyse data, the system being configured to:

(a) store in a memory a structured, machine-readable representation of data that conforms to a machine-readable language; the structured, machine-readable representation of data including a representation of a spoken, written or GUI instruction provided by a human to a human/machine interface;

(b) automatically process the structured representation of data for one or more of the following: to derive facts or relationships, to reason, to learn, to translate, to answer questions, to process natural language content, to enable man-machine interaction, to represent and to police rules or tenets, to enable one or more vertical applications.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

N2: Search and Analysis of Documents or Web pages.

It is possible to automatically translate websites and web documents (in the limit, the entire WWW) into UL and hence give them a deep machine-understandable semantic meaning; this makes it possible to use web documents in far more powerful ways including reasoning from and integrating the meaning of those documents in ways that were previously not possible.

We can generalise to:

A computer implemented method for the automated analysis or use of data, comprising the steps of:

(a) storing in a memory a structured, machine-readable representation of data that conforms to a machine-readable language; the structured, machine-readable representation of data including a representation of at least parts of documents stored in a document store;

(b) automatically processing the structured representation of data for one or more of the following: to derive facts or relationships, to reason, to learn, to translate, to answer questions, to process natural language content, to enable man-machine interaction, to represent and to police rules or tenets, to enable one or more vertical applications that require a search for, or analysis of, documents.

Computer-based system configured to analyse data, the system being configured to:

(a) store in a memory a structured, machine-readable representation of data that conforms to a machine-readable language; the structured, machine-readable representation of data including a representation of at least parts of documents stored in a document store;

(b) automatically processing the structured representation of data for one or more of the following: to derive facts or relationships, to reason, to learn, to translate, to answer questions, to process natural language content, to enable man-machine interaction, to represent and to police rules or tenets, to enable one or more vertical applications that require a search for, or analysis of, documents.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the parts of the documents have been automatically translated into the machine readable language.

a machine learning system is used to generate the semantic nodes or passages that represent the words in the documents.

the machine learning system is a neural network system, such as a deep learning system.

a neural architecture is used to generate the machine-readable language the neural architecture utilises recurrent neural networks or LSTMs or attention mechanisms or transformers the machine learning system has been trained on training data comprising natural language and a corresponding structured machine-readable representation, such as a machine-readable language comprising semantic nodes and passages.

a passage of natural language is passed through a sequence-to-sequence neural architecture trained on training data comprising natural language and a corresponding structured representation that encodes meaning.

the neural network system utilises recurrent neural networks or LSTMs or attention mechanisms or transformers.

the neural network system is a switch transformer feed forward neural network system.

the neural architecture comprises an encoder and decoder and beam searching is used during decoding of the semantic representations from the decoder to remove invalid semantic representations.

when automatically translating a sequence of words expressed in the natural language into the machine-readable language, the structure of the sequence of words is compared with known machine-readable language structures in the memory to identify similarities.

automatically translating the word or sequence of words into the machine-readable language is achieved by referencing a store of previously identified correct translations between the natural language and the machine-readable language automatically translating the word or sequence of words into the machine-readable language is achieved by utilising a pipeline of functions which transform the word or sequence of words into a series of intermediate forms user's queries have been automatically translated into UL and the system responds to the users requests by utilising the translated UL.

method is a web search system and the document store includes pages from the world wide web which are indexed and then at least partially translated into UL.

translation includes turning natural language components of these pages into UL or turning tabular or other structured data into UL.

answers to queries include links to web pages containing the information being searched for or providing the services being searched for or the system provide the information directly in the form of a text or spoken answer.

direct responses are accompanied by links to the sources of this information and include associated data such as images or tables.

N3. Mapping Data Represented as UL, Associated Systems Utilising Mapping Data and Location Based Search It is possible to represent mapping and location-based data into UL and hence give them a machine-understandable semantic meaning; this makes it possible to use mapping and location-based data in far more powerful ways. We can generalise to:

A computer implemented method for the automated analysis or use of data, comprising the steps of:

(a) storing in a memory a structured, machine-readable representation of data that conforms to a machine-readable language; the structured, machine-readable representation of data including representations of mapping or location-based data;

(b) automatically processing the structured representation of data for one or more of the following: to derive facts or relationships, to reason, to learn, to translate, to answer questions, to process natural language content, to enable man-machine interaction, to represent and to police rules or tenets, to enable one or more vertical applications that use location-based or mapping data.

Computer-based system configured to analyse data, the system being configured to:

(a) store in a memory a structured, machine-readable representation of data that conforms to a machine-readable language; the structured, machine-readable representation of data including representations of mapping or location-based data;

(b) automatically process the structured representation of data for one or more of the following: to derive facts or relationships, to reason, to learn, to translate, to answer questions, to process natural language content, to enable man-machine interaction, to represent and to police rules or tenets, to enable one or more vertical applications that use location-based or mapping data.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

mapping data or location-based data has been automatically translated into the machine readable language.

a machine learning system is used to generate the semantic nodes or passages that represent the mapping data or location-based data.

the machine learning system is a neural network system, such as a deep learning system.

a neural architecture is used to generate the machine-readable language the neural architecture utilises recurrent neural networks or LSTMs or attention mechanisms or transformers the machine learning system has been trained on training data comprising natural language and a corresponding structured machine-readable representation, such as a machine-readable language comprising semantic nodes and passages.

a passage of natural language is passed through a sequence-to-sequence neural architecture trained on training data comprising natural language and a corresponding structured representation that encodes meaning.

the neural network system utilises recurrent neural networks or LSTMs or attention mechanisms or transformers.

the neural network system is a switch transformer feed forward neural network system.

the neural architecture comprises an encoder and decoder and beam searching is used during decoding of the semantic representations from the decoder to remove invalid semantic representations.

when automatically translating a sequence of words expressed in the natural language into the machine-readable language, the structure of the sequence of words is compared with known machine-readable language structures in the memory to identify similarities.

automatically translating the word or sequence of words into the machine-readable language is achieved by referencing a store of previously identified correct translations between the natural language and the machine-readable language.

automatically translating the word or sequence of words into the machine-readable language is achieved by utilising a pipeline of functions which transform the word or sequence of words into a series of intermediate forms.

N4. Identifying Relevant Adverts and News

UL enables advertisements, news articles or other information items (e.g. on the WWW) to be translated to UL and their semantic meaning made available for machine processing: this enables automated assessment of relevance to specific individuals, and hence personalised advertising etc.

We can generalise to:

A computer implemented method for the automated analysis or use of data, comprising the steps of:

(a) storing in a memory a structured, machine-readable representation of data that conforms to a machine-readable language that represents meaning; the structured, machine-readable representation of data relating to representations of at least some part of one or more advertisements, news articles or other information items;

(b) automatically processing the structured representation of data to identify advertisements, news articles or other information items relevant to a specific individual.

Computer-based system configured to analyse data, the system being configured to:

(a) store in a memory a structured, machine-readable representation of data that conforms to a machine-readable language; the structured, machine-readable representation of data including representations of at least some part of one or more advertisements, news articles or other information items;

(b) automatically process the structured representation of data to identify advertisements, news articles or other information items relevant to a specific individual.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the method determines advertisements, news articles or other information items relevant to a user by also analysing semantic nodes that are a representation of user-specific data.

the user-specific data includes one or more of the following relating to a user: social media profile, postings, profile information, "likes", web search or web browsing history, natural language conversation/exchanges between the user and a system where the system stores and remembers information the user has given about him or herself.

advertisements, news articles or other information items relevant to a specific individual and the user-specific data has been automatically translated into the machine readable language.

a machine learning system is used to generate the semantic nodes or passages that represent the advertisements, news articles or other information items relevant to a specific individual, and the user-specific data.

the machine learning system is a neural network system, such as a deep learning system.

the machine learning system has been trained on training data comprising natural language and a corresponding structured machine-readable representation, such as a machine-readable language comprising semantic nodes and passages.

a passage of natural language is passed through a sequence-to-sequence neural architecture trained on training data comprising natural language and a corresponding structured representation that encodes meaning.

the neural network system is a switch transformer feed forward neural network system.

the neural architecture comprises an encoder and decoder and beam searching is used during decoding of the semantic representations from the decoder to remove invalid semantic representations.

when automatically translating a sequence of words expressed in the natural language into the machine-readable language, the structure of the sequence of words is compared with known machine-readable language structures in the memory to identify similarities.

automatically translating the word or sequence of words into the machine-readable language is achieved by referencing a store of previously identified correct translations between the natural language and the machine-readable language automatically translating the word or sequence of words into the machine-readable language is achieved by utilising a pipeline of functions which transform the word or sequence of words into a series of intermediate forms N5. Aggregation and Summarisation of News UL enables news from multiple sources (e.g. on the WWW) to be partially or fully translated to UL and their semantic meaning made available for machine processing and summarising: this enables automated personalised news summaries etc. We can generalise to:

A computer implemented method for the automated analysis or use of data, comprising the steps of:
(a) storing in a memory a structured, machine-readable representation of data that conforms to a machine-readable language; the structured, machine-readable representation of data including representations of news from multiple sources;
(b) automatically processing the structured representation of data for one or more of the following: to generate a summary of the news from multiple sources; using the news summaries to derive facts or relationships, to reason, to learn, to translate, to answer questions, to process natural language content, to enable man-machine interaction, to represent and to police rules or tenets, to enable one or more vertical applications to use the summaries of news from multiple sources.

Computer-based system configured to analyse data, the system being configured to:
(a) store in a memory a structured, machine-readable representation of data that conforms to a machine-readable language; the structured, machine-readable representation of data including representations of news from multiple sources;
(b) automatically process the structured representation of data for one or more of the following: to generate a summary of the news from multiple sources; using the news summaries to derive facts or relationships, to reason, to learn, to translate, to answer questions, to process natural language content, to enable man-machine interaction, to represent and to police rules or tenets, to enable one or more vertical applications to use the summaries of news from multiple sources.

In the preferred implementation, the structured, machine-readable representation of data that conforms to a machine-readable language comprises semantic nodes and passages;
  and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:
news articles relevant to a specific user are determined by also analysing semantic nodes that are a representation of user-specific data.
the user-specific data includes one or more of the following relating to a user: social media profile, postings, profile information, "likes", web search or web browsing history, natural language conversation/exchanges between the user and a system where the system stores and remembers information the user has given about him or herself.
news articles have been automatically translated into the machine readable language.
a machine learning system is used to generate the semantic nodes or passages that represent the news articles.

the machine learning system is a neural network system, such as a deep learning system.
a neural architecture is used to generate the machine-readable language
the neural architecture utilises recurrent neural networks or LSTMs or attention mechanisms or transformers
the machine learning system has been trained on training data comprising natural language and a corresponding structured machine-readable representation, such as a machine-readable language comprising semantic nodes and passages.
a passage of natural language is passed through a sequence-to-sequence neural architecture trained on training data comprising natural language and a corresponding structured representation that encodes meaning.
the neural network system utilises recurrent neural networks or LSTMs or attention mechanisms or transformers.
the neural network system is a switch transformer feed forward neural network system.
the neural architecture comprises an encoder and decoder and beam searching is used during decoding of the semantic representations from the decoder to remove invalid semantic representations.
when automatically translating a sequence of words expressed in the natural language into the machine-readable language, the structure of the sequence of words is compared with known machine-readable language structures in the memory to identify similarities.
automatically translating the word or sequence of words into the machine-readable language is achieved by referencing a store of previously identified correct translations between the natural language and the machine-readable language
automatically translating the word or sequence of words into the machine-readable language is achieved by utilising a pipeline of functions which transform the word or sequence of words into a series of intermediate forms N6. Matching Between People Using UL UL enables accurate and scalable match-finding: for example, sex, age, and other information relevant to dating or matching for marriage or friendship or matching for business contacts can be translated to UL and their semantic meaning made available for machine processing: this enables improved automated personalised matching. We can generalise to:

A computer implemented method for the automated analysis or use of data, comprising the steps of:
(a) storing in a memory a structured, machine-readable representation of data that conforms to a machine-readable language; the structured, machine-readable representation of data including representations of personal information defining one or more of the following attributes of a person: sex, age, information relevant to dating or match-making, information relevant to identifying business connections; information relevant to identifying friends;
(b) automatically processing the structured representation of data to provide a compatibility match between persons.

Computer-based system configured to analyse data, the system being configured to:
(a) store in a memory a structured, machine-readable representation of data that conforms to a machine-readable language; the structured, machine-readable representation of data including representations of personal information defining one or more of the following attributes of a person: sex, age, information relevant to dating or match-making, information relevant to identifying business connections; information relevant to identifying friends;

(b) automatically process the structured representation of data to provide a compatibility match between persons.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the personal information comprises information coming from conversations in natural language with the system where the user's responses are translated into the structured, machine-readable representation of data.

the personal information comprises information coming from the output of a machine learning model.

the personal information comprises information coming from reasoning.

the personal information comprises information come from learning.

N7. Identifying Abusive or Untrue Postings in Social Media

UL enables social media postings to be partially or fully translated to UL and their semantic meaning made available for machine processing: this enables automated and high-precision analysis of compliance with requirements preventing abusive, false or illegal postings. We can generalise to:

A computer implemented method for the automated analysis or use of data, comprising the steps of:

(a) storing in a memory a structured, machine-readable representation of data that conforms to a machine-readable language; the structured, machine-readable representation of data including representations of social media postings;

(b) automatically processing the structured representation of data to determine if the postings are compliant with requirements preventing abusive or illegal postings.

Computer-based system configured to analyse data, the system being configured to:

(a) store in a memory a structured, machine-readable representation of data that conforms to a machine-readable language; the structured, machine-readable representation of data including representations of social media postings;

(b) automatically process the structured representation of data to determine if the postings are compliant with requirements preventing abusive or illegal postings.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the processing includes determining whether the social media postings are factually true.

the processing includes determining whether the social media postings are illegal.

the machine-readable representation of data further includes at least a partial representation of the requirements preventing abusive or illegal postings and the processing references the representation of the requirements.

the processing additionally generates a natural language explanation of why the social media posting is not compliant with the requirements.

the processing additionally applies statistical machine-learning models to the social media postings and uses the results of the models.

N8. Analysis of Customer Reviews

UL enables customer reviews (e.g. of products, of companies) to be translated to UL and their semantic meaning made available for machine processing: this enables automated analysis of customer reviews. We can generalise to:

A computer implemented method for the automated analysis or use of data, comprising the steps of:

(a) storing in a memory a structured, machine-readable representation of data that conforms to a machine-readable language; the structured, machine-readable representation of data including representations of customer reviews of products or services;

(b) automatically processing the structured representation of data to analyse the customer reviews.

Computer-based system configured to analyse data, the system being configured to:

(a) store in a memory a structured, machine-readable representation of data that conforms to a machine-readable language; the structured, machine-readable representation of data including representations of customer reviews;

(b) automatically process the structured representation of data to analyse the customer reviews.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

the system is further configured to automatically answer questions about the products or services by referencing the structured, machine-readable representation of data.

the system is further configured to automatically answer general product questions from customers by referencing the structured, machine-readable representation.

the system is further configured to translate some or all of the natural language in a customer review into the structured, machine-readable representation of data.

N9. Shopping Queries and Product Requests

UL enables product descriptions, user product requests, a user's previous search, social media or shopping histories to be translated to UL and their semantic meaning made available for machine processing: this enables automated analysis of which products best match a user's product requests or a user's previous search, social media or shopping history. We can generalise to:

A computer implemented method for the automated analysis or use of data, comprising the steps of:
(a) storing in a memory a structured, machine-readable representation of data that conforms to a machine-readable language; the structured, machine-readable representation of data including representations of product descriptions, user product requests, a user's previous search, social media or shopping histories;
(b) automatically processing the structured representation of data to determine which products best match a user's product requests or a user's previous search, social media or shopping history.

Computer-based system configured to analyse data, the system being configured to:
(a) store in a memory a structured, machine-readable representation of data that conforms to a machine-readable language; the structured, machine-readable representation of data including representations of product descriptions, user product requests, a user's previous search, social media or shopping histories;
(b) automatically process the structured representation of data to determine which products best match a user's product requests or a user's previous search, social media or shopping history.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:
presenting the products which best match to the user for possible purchase.
automatically processing the structured representation of data happens as part of a natural language conversation with the user about what the user is looking to purchase.

N.10 Job Matching

UL enables job descriptions and job applicants' skills and experience to be translated to UL and their semantic meaning made available for machine processing: this enables automated analysis of which jobs best match a job applicant's skills and experience over a very wide variety of skills, jobs and backgrounds without additional computer code and for those matches to be very accurate and explainable in natural language. We can generalise to:

A computer implemented method for the automated analysis or use of data, comprising the steps of:
(a) storing in a memory a structured, machine-readable representation of data that conforms to a machine-readable language; the structured, machine-readable representation of data including representations of job descriptions and job applicants' skills and experience;
(b) automatically processing the structured representation of data to determine which jobs best match a job applicant's skills and experience.

Computer-based system configured to analyse data, the system being configured to:
(a) store in a memory a structured, machine-readable representation of data that conforms to a machine-readable language; the structured, machine-readable representation of data including representations of job descriptions and job applicants' skills and experience;
(b) automatically process the structured representation of data to determine which jobs best match a job applicant's skills and experience.

In the preferred implementation, the structured, machine-readable representation of data that conforms to a machine-readable language comprises semantic nodes and passages;
and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:
A system is operable to match candidates to open jobs and comprises at least one data store containing: a plurality of candidate resumes where at least some parts of at least some of the candidate resumes are in a structured machine-readable form that encodes meaning; a plurality of job specifications for open roles where at least some of parts of at least some of the job specifications are stored in the structured machine-readable form that encodes meaning and where the system is further operable to match the plurality of candidate resumes with the plurality of job specifications to identify high confidence matches between candidates and open roles.
the structured machine-readable form is a language that represents meaning by creating combinations of identifiers and where at least some of the identifiers represent human skills and experience.
at least one data store further stores a representation of candidates' desired roles at least partially represented in the structured machine-readable form and where the system is further operable to match open roles against the representation of candidates' desired roles in order to improve the matches between candidates and open roles.
the system is further operable to send a push notification to a mobile device when a high confidence match is found.
the system is further operable to explain how the candidate matches the role by generating an explanation of which bits of the job specification match the skills and experience of the candidate.
the explanation is in a natural language.
the system is operable to match requirements in job specifications to the skills and experience of a candidate where there are no keywords in common between the relevant parts of the natural language versions of the candidate resume and job specification.
the system is operable to make a sequence of logical reasoning steps in order to match the skills or experience of a candidate with a requirement in a job specification.

N.11 Horizontal Health Application

UL supports the creation of a horizontal health application able to integrate an extremely broad amount of heterogeneous health data. We can generalise to:

A computer implemented method for the automated analysis or use of data, comprising the steps of:
(a) storing in a memory a structured, machine-readable representation of data that conforms to a machine-readable language; the structured, machine-readable representation of data including representations of personal health or medical data;
(b) automatically processing the structured representation to analyse the personal health or medical data.

Computer-based system configured to analyse data, the system being configured to:
(a) store in a memory a structured, machine-readable representation of data that conforms to a machine-readable language; the structured, machine-readable representation of data including representations of personal health or medical data;
(b) automatically process the structured representation to analyse the personal health or medical data.

In the preferred implementation, the structured, machine-readable representation of data that conforms to a machine-readable language comprises semantic nodes and passages;
   and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Optional features:
a broad set of health data for one or more people is managed and where at least some of the health data is represented in a structured machine-readable form that encodes meaning stored within one or more data stores.
the health data includes nutrition data about food or drink that has been consumed by at least one of the one or more people.
the nutrition data includes data that represents the uncertainty about the volume or nutritional information or composition of what was consumed.
the health data comprises data about the results of blood tests or measurements or body composition or activity information or genetic data or microbiome data or bowel motion events or sleep data or workout data or activity data or symptoms of diseases or human moods or menstruation or ingestion of medication or medical conditions or data from any wearable device.
conversing with one or more users via text is enabled.
selected other people are enabled to converse with the one or more users and to view relevant health data.
graphs of specific types of health data are created whereby users can see how different data correlates.
health data is analysed to uncover insights relevant to the specific user's health.
include potential dietary intolerances or behaviours that influence sleep.
elements of the health data are combined to calculate an additional item of health data not already present in the health data.
the additional item of health data is an estimate of caffeine present in a user's body at a particular time.

N.12 Accounting

UL enables financial or accounting information to be translated to UL and their semantic meaning made available for machine processing: this enables automated analysis of financial or accounting information. We can generalise to:
  A computer implemented method for the automated analysis or use of data, comprising the steps of:
  (a) storing in a memory a structured, machine-readable representation of data that conforms to a machine-readable language; the structured, machine-readable representation of data including representations of financial or accounting information;
  (b) automatically processing the structured representations to analyse the personal financial or accounting information.

Computer-based system configured to analyse data, the system being configured to:
(a) store in a memory a structured, machine-readable representation of data that conforms to a machine-readable language; the structured, machine-readable representation of data including representations of financial or accounting information;
(b) automatically process the structured representations to analyse the financial or accounting information.

In the preferred implementation, the structured, machine-readable representation of data that conforms to a machine-readable language comprises semantic nodes and passages;
   and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:
accounting data for at least one business is processed, and at least some of the accounting data is represented in a structured machine-readable format that encodes real-world meaning stored within one or more data stores.
the structured machine-readable format is comprised of combinations of identifiers where at least some of the identifiers represent real-world entities relevant to the activities of the at least one business and where further meaning is encoded from the choice of combinations of the identifiers.
accountancy data is automatically presented in a plurality of different accountancy standards.
answer to questions about the activities of the at least one business are generated.

N.13 Voice Assistants/Chatbots

Natural language directed to a voice assistant or chatbot can be translated into UL and the UL representation used internally to answer questions, converse or take actions. This horizontal representation enables easier scaling of the voice assistant or chatbot's capabilities and makes it easier for the system to work with large numbers of other natural languages as only the translation steps need to change. We can generalise to:
  A computer implemented method for the automated analysis or use of data, comprising the steps of:
  (a) storing in a memory a structured, machine-readable representation of data that conforms to a machine-readable language; the structured, machine-readable representation of data including representations of user speech or text input to a human/machine interface;
  (b) automatically processing the structured representations to analyse the user speech or text input.

Computer-based system configured to analyse data, the system being configured to:
(a) store in a memory a structured, machine-readable representation of data that conforms to a machine-readable language; the structured, machine-readable representation of data including representations of user speech or text input to a human/machine interface;
(b) automatically process the structured representations to analyse the user speech or text input to a human/machine interface.

In the preferred implementation, the structured, machine-readable representation of data that conforms to a machine-readable language comprises semantic nodes and passages;

and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

Other optional features:

Privacy Preserving Mode a first wakeword initiates processing, and a privacy-preserving state is then entered, requiring a second wakeword and where the second wakeword is sufficiently long or unusual that a false recognition of the second wakeword is significantly more improbable relative to the first wakeword.

Multiple Different Voice Assistants the experience of a plurality of different voice assistants to a plurality of users is delivered and at least one data store contains personality information which determines the personality of at least some of the plurality of different voice assistants.

the personality information includes information about the voice assistant's gender or name or voice or moods or emotional reactions or level of formality or position on the extrovert-introvert scale or position on any Myers Briggs scale or a Myers Briggs categorisation or categorisation in a personality test or visual appearance.

there is at least one set of machine-readable tenets that represent goals and rules to guide at least some of the plurality of voice assistants and actions are then done that conform with the tenets by referencing the tenets.

the at least one set of machine-readable tenets is a plurality of sets of machine-readable tenets and where selected ones of the plurality of different voice assistants are mapped to selected ones of the plurality of sets of machine-readable tenets whereby different voice assistants are driven by different tenets.

private user data is accessible only by selected ones of the plurality of different voice assistants.

Device Types

The computer-based system is configured to be a voice assistant.

The computer-based system is a voice assistant device configured to control items in a home, car or other environment, using the user speech or text input.

The computer-based system is a voice assistant device configured to run on a smartphone, laptop, smart speaker or other electronic device.

The computer-based system is a voice assistant device configured to run at least in part on cloud or central servers and at least in part on edge devices.

For each of the Use Case concepts N1-N13, the following apply:

the method and system uses a single syntactical item, such as brackets, to disambiguate combinations of nodes, as defined in Concept A.

the method and system uses a shared syntax across factual statements, queries and reasoning, as defined in Concept B.

the method and system uses nesting of nodes, as defined in Concept C.

the method and system uses ID selection, from an address space that is sufficiently large to enable users to select a new identifier with negligible risk of selecting a previously allocated identifier, as defined in Concept D.

the method and system imposes no restrictions on which clients are permitted to generate a semantic node or passage, as defined in Concept E.

the method and system uses the consolidated universal language concepts, as defined in Concept F.

the method and system includes question answering, as defined in Concept G.

the method and system includes learning, as defined in Concept H.

the method and system includes translation, as define in Concept I.

the method and system includes semantic node resolution, as defined in Concept J.

the method and system includes translation between natural languages, as defined in Concept K.

the method and system is used in a voice assistant, as defined in Concept L.

the method and system uses tenets, as defined in Concept M.

Optional Features Applicable to All Concepts A-N

Note that in the following, any occurrence of 'semantic node' or 'passage' can be generalised to a 'structured, machine-readable representation' and also to a 'machine representation'. Similarly, any occurrence of 'structured, machine-readable representation' or equivalent can be generalised to a 'machine representation'. In the appended Claims, we use the term 'machine representation' for conciseness.

Simple Syntax the structured, machine-readable representation includes a single syntactical item to disambiguate the meaning of structured representations of data.

the single syntactical item to disambiguate meaning represents nesting of the structured, machine-readable representation of data.

the single syntactical item to disambiguate meaning represents nesting of semantic nodes and passages to any arbitrary depth.

the single syntactical item to disambiguate the meaning of the combination is parentheses or brackets.

the single syntactical item to disambiguate the meaning of the combination is the only syntactical item to disambiguate the meaning of the combination.

the single syntactical item to disambiguate the meaning of the combination is the primary syntactical item to disambiguate the meaning of the combination.

the syntax applies to all nodes and combinations of nodes.

the syntax is a simple unambiguous syntax comprising nesting of nodes.

the syntax is a simple unambiguous syntax comprising nesting of nodes to any arbitrary depth.

the syntax is a simple unambiguous syntax in which semantic nodes can only be combined in nested combinations.

the syntax allows for expressions to be nested indefinitely to allow a user to define a concept, coupled with contextual information about the concept, as a hierarchy of semantic nodes.

Combination nodes can contain any finite number of semantic nodes and the semantic nodes within them can also be combination nodes creating any level of nesting.

a semantic link between nodes, such as ISA, is itself a semantic node.

the syntax for the machine-readable language applies to combinations of semantic nodes that represent factual statements, query statements and reasoning statements.

The syntax of the structured, machine-readable representation of data conforms or substantially conforms to the production grammar "<passage>::=<id>|<passage>::=(<passage><passage>*)" where "<passage>*" means zero or one or more further passages and where <id> is an identifier for a semantic node.

Node Meaning the machine-readable language is a universal language for which substantially anything expressible in natural language is expressible as a structured, machine-readable representation of data or a combination of structured, machine-readable representations of data.

a structured, machine-readable representation of data represents a specific entity, such as a word, concept, or other thing, and once generated, identifies uniquely that specific word, concept, or other thing in the universal language.

an ordered or partially ordered collection of structured, machine-readable representations of data captures a specific meaning or semantic content.

the meaning of a structured, machine-readable representation of data comes from statements written in the machine-readable language.

the meaning of a structured, machine-readable representation of data comes from other structured, machine-readable representations of data that represents things that have been said about the structured, machine-readable representation of data.

a structured, machine-readable representation of data that represents an entity encodes the semantic meaning of that entity through links to structured, machine-readable representations of data of related words, concepts, other terms, or logical processes.

combining structured, machine-readable representations of data generates a new word, concept, or other term with a new meaning or semantic content in the machine-readable language the machine-readable language is understandable to human users where it corresponds to an equivalent statement in natural language.

Generating Nodes

A semantic node once defined has an identifier or ID.

semantic nodes are identified with a UUID.

The identifier is selected from an address space that is sufficiently large to enable users to select new identifiers independently of other users without duplication.

The identifier is selected from an address space that is sufficiently large to enable users to select a new identifier with negligible risk of selecting a previously allocated identifier.

the ID is a UUID.

the ID is a 128-bit version 4 UUID (RFC 4122) with hyphenated lower-case syntax.

the ID is a UUID or a string, such as a Unicode string.

a string can denote itself as a structured, machine-readable representation of data and its meaning is strictly the string itself only and any natural language meaning contained within the string is not part of the meaning of the string.

a string can denote itself as a semantic node and its meaning is strictly the string itself only and any natural language meaning contained within the string is not part of the meaning of the string.

a string is represented by an ID as an additional identifier.

a string is represented as a UUID or other numerical ID and a separate passage links the string to that numerical ID to provide its meaning.

two identical strings used as semantic nodes have universal meaning as that string.

any user can coin its own semantic nodes with its own local meaning by picking an unused identifier.

any user can coin its own identifier for a semantic node even if another identifier is already used for the semantic node.

any user is free to define its own meaning to combinations of semantic nodes.

there can be multiple different semantic nodes for the same specific word, concept, or other thing.

any user that chooses to create machine representations, such as passages, that use shared semantic nodes is also expressing the same meaning by combining them, so that the meaning that comes from combining shared semantic nodes is universal.

there can be multiple different structured, machine-readable representation of data for the same specific word, concept, or other thing.

any user that chooses to create passages that use shared structured, machine-readable representation of data is also expressing the same meaning by combining them, so that the meaning that comes from combining shared structured, machine-readable representations of data is universal.

each sense of each word in a dictionary is represented by a semantic node.

a machine learning system generates passages by autonomously learning from natural language documents or conversations.

Passages are derived from a machine analysis of natural language documents, such as WWW pages or conversations.

a semantic node is a structured, machine-readable representation of data that, once defined, has an identifier so it can be referred to within the machine-readable language.

a "shared ID" is an ID used by more than one user; a "private ID" or "local ID" is similarly an ID used by only one user and is not published or exposed to other users; a "public ID" is an ID that a user has used in UL that can be seen by every user.

A passage is a combination of semantic nodes expressing meaning, and is the sole nesting construct.

semantic nodes in infinite classes are represented as a combination of a plurality of other nodes.

Scalability the machine-readable language is scalable since any natural language word, concept, or other thing can be represented by a structured, machine-readable representation of data.

the machine-readable language is scalable since there are no restrictions on which users can create a structured, machine-readable representation of data or related identifier.

Questions

Questions are represented in the machine-readable language with a passage which comprises a node identifying the passage as a question, language representing zero or one or more unknown entities being requested within the semantics of the question and language representing the semantics of the question and referencing the zero or one or more unknown entities.

Questions are represented in the machine-readable language with a passage of the form (Question <unknowns>)(<passage>) where Question is a semantic node and <unknowns> is a list of zero or one or more semantic nodes representing unknown values (similar in meaning to letters of the alphabet in algebra) and where <passage> is where the unknowns are used to express what is being asked about.

generating responses to queries comprises three operations, namely matching with structured, machine-readable representation of data, such as passages, in a store, fetching and execution of computation units and fetching reasoning passages.

a question is represented in the memory as a structured, machine-readable representation of data, and the representation of the question, the structured, machine-readable representations of data previously stored in the memory store, the computation units and the reasoning passages are all represented in substantially the same machine-readable language Reasoning Reasoning is where machine-readable language is generated from other machine-readable language using reasoning steps that are represented as passages which represent the semantics of the reasoning steps.

reasoning is done with a series of one or more queries being answered to see if the reasoning step is valid.

reasoning is done with a series of one or more queries being answered to generate results needed for the result of the reasoning.

passages represent details for the computation unit that are needed to select and run the computation unit, namely defining what it can do, how to run it and how to interpret the results.

The step of fetching and execution of one or more initial reasoning passages returns other passages with unknowns that need to be processed, and the results of that processing is a tree of connection that is used to give results for the initial passage.

The tree of connection is stored and the processing of these other passages with unknowns happens in parallel, allowing data fetching and exploration of reasoning to be parallelized.

once all passages are processed up to a given maximum reasoning depth, a second non-parallelised step is used to walk through this tree of processed passages and unknowns mappings to find valid answers.

each passage in a list of passages is processed to identify valid mappings from the passage memory store and the computation units, where a valid mapping for that list of passages is one where all unknowns have a value and there are no contradicting mappings between passages in the list.

The step of identifying valid mappings recursively looks through the data and finds all valid mappings for the initial question which can be returned as the answer.

at least some of the passages that have been generated from reasoning or computation are stored in the passage memory store, making these available in the future for faster processing.

The history of these generated passages is also stored so that changes to a trust level in the passages that were used to generate them can be extended to the trust given to these generated passages.

The history of these generated passages is also stored to enable the removal of generated passages when the trusted status of one or more of the passages used to generate them changes.

When a new passage is added to the passage memory store it is assigned a low initial trust value when added by a normal user and a higher starting value when added by a privileged user.

a signal from an application of the system or method is stored in association with the passages utilised by the application in order to keep track of the value of the passages.

passages are assigned a vector of values where the number at each index represents a different quality of the passage.

the different qualities include veracity, usefulness, and efficiency.

a process that uses the passages utilises a priorities vector with numbers at each index that indicate how much they prioritise that value.

the overall value of the passage to that process can then be obtained from the dot product of the vectors.

a reasoning engine experiments with high and lower value passages to answer the question and the answers provided by the reasoning engine are then monitored for any signals that would indicate whether the lower value passages have a positive or negative effect on the answers and this information then feeds back into an auto-curation process which re-evaluates the value of the passage with the new signal.

an auto-curation process automatically tests passages to determine if they should be used for question-answering.

the structured, machine-readable representations of data previously stored in a memory store have been curated with an automatic method.

the question is the result of translating natural language asked by a user into a substantially semantically-equivalent representation in the machine-readable language.

the response to the question is subsequently translated into semantically equivalent natural language and presented to one or more users.

the question is the result of translating a question spoken by a user in a natural language into a substantially semantically-equivalent representation in the machine-readable language and the user is subsequently played a spoken answer where the spoken answer is the result of translating the response to the question into the natural language.

Computation Units a computation unit represents an individual computational capability that is available for reasoning and other purposes.

computation units are semantic nodes.

passages, or combinations of semantic nodes, represents details for the computation unit that are needed to select and run the computation unit, namely defining what it can do, how to run it and how to interpret the results.

Computation units are appropriately utilised during reasoning.

Learning new information that is learnt is represented in a structured, machine-readable representation of data that conforms to a machine-readable language.

learning new information is obtained from automatically processing the structured, machine-readable representation of data to obtain, or learn, new information, and the new information is itself represented as structured, machine-readable representations of data that are stored in memory.

Learning new information is obtained from a machine-learning system which generates classifications or predictions or other outputs which are represented as passages.

a machine-learning system processes the semantic nodes and passages to obtain, or learn, new information.

new information is generated by automatically processing the semantic nodes and passages to answer a question.

The method of any preceding Claim in which a question is represented as one or more machine representations, such as passages and a response to the question is automatically generated using one or more of the following steps: (i) matching the question with machine representations previously stored in a memory store; (ii) fetching and executing one or more computation units, where computation units represent computational capabilities relevant to answering the question; (iii) fetching and execution of one or more reasoning machine representations, such as reasoning passages, which are machine representations that represent the semantics of potentially applicable reasoning steps relevant to answering the question.

the new information represented as semantic nodes or passages are stored and used to improve performance of learning new facts.

the new information represented as semantic nodes or passages are stored and used to improve reasoning steps.

the new information represented as semantic nodes or passages are stored and used to explain or describe the new information in natural language.

the new information represented as semantic nodes or passages are stored and used in text or spoken conversations with human users.

learning new information takes place from conversation with or other natural language provided by human users, in which natural language provided by users in spoken or written form is translated into semantic nodes and passages and then new information represented by these semantic nodes and passages is stored and used.

learning takes place from reasoning, in which semantic nodes and passages that are generated from a chain of reasoning steps, and are stored and utilised.

learning takes place from natural language, in which by translating all or parts of document sources of natural language, such as web pages, scientific papers or other articles into semantic nodes or passages, the resulting semantic nodes or passages are then utilised by applications.

non-document sources of natural language, including audio recordings or videos containing human speech, are used and speech recognition technology is first utilised to create a text transcription of the recordings of voice which are then translated into semantic nodes and passages.

machine learning system is used to analyse document and non-document data and create passages from that data.

Machine Learning a machine learning system is used to generate the semantic nodes or passages that represent the words or sequence of words in a natural language.

the machine learning system is a neural network system, such as a deep learning system.

a neural architecture is used to generate the machine-readable language.

the neural architecture utilises recurrent neural networks or LSTMs or attention mechanisms or transformers.

the machine learning system has been trained on training data comprising natural language and a corresponding structured machine-readable representation, such as a machine-readable language comprising semantic nodes and passages.

a passage of natural language is passed through a sequence-to-sequence neural architecture trained on training data comprising natural language and a corresponding structured representation that encodes meaning.

the machine learning, e.g. neural network, system is a switch transformer feed forward neural network system the machine learning system, e.g. neural architecture, comprises an encoder and decoder and beam searching is used during decoding of the semantic representations from the decoder to remove invalid semantic representations.

when automatically translating a sequence of words expressed in the natural language, (such as speech or text input) into the machine-readable language, the structure of the sequence of words is compared with known machine-readable language structures in the memory to identify similarities.

automatically translating the word or sequence of words (such as speech or text input) into the machine-readable language is achieved by referencing a store of previously identified correct translations between the natural language and the machine-readable language.

automatically translating the word or sequence of words (such as speech or text input) into the machine-readable language is achieved by utilising a pipeline of functions which transform the word or sequence of words into a series of intermediate forms.

the semantic impact of changes to the word or sequence of words (such as speech or text input) in a natural language wording of the translation in the natural language is automatically assessed to determine whether known or ground truth examples of semantic nodes or passages can be used that are sufficient accurate.

the semantic nodes or passages that represent the words or sequence of words (such as speech or text input) provides a machine-readable representation of the meaning of the words or sequence of words.

the semantic nodes or passages that represent the words or sequence of words (such as speech or text input) are processed by a computer-based system for one or more of the following: to derive facts or relationships, to reason, to learn, to translate, to answer questions, to process natural language content, to enable man-machine interaction, to represent and to police rules or tenets, to enable one or more vertical applications.

the semantic nodes or passages that represent the words or sequence of words (such as speech or text input) are processed by a computer-based system to generate an output that is human-readable.

the human readable output include one or more of the following: an answer to a question expressed in the natural language; a reasoning statement that explains how the system has reached a conclusion; a learning statement that explains what the system has learnt; a response in a man/machine interaction.

a neural net is trained end-to-end to turn audio or video data directly into semantic nodes and passages.

natural language-based learning is combined with statistical machine-learning to optimise the translation of document and non-document data (such as speech or text input) into semantic nodes and passages.

a machine learning system is used to generate the semantic nodes or passages the neural network system is a switch transformer feed forward neural network system structured data, such as the content of a table found in a document or on the web, a spreadsheet or the content of a relational, graph or other database is turned into semantic nodes and passages by assigning semantic nodes to the identifiers in the structured data and writing semantic nodes and passages that correspond to the meaning of the structured data.

learning takes place from analysis of other data, in which the data is processed with an algorithm and the results of that processing is represented in semantic nodes and passages.

Translation to and from UL a word or sequence of words in a natural language is received and automatically translated into the machine-readable language by identifying or generating structured machine-readable representations that semantically represent the meaning of the word or sequence of word.

a machine learning system is used to generate the semantic nodes or passages that represent the words or sequence of words in a natural language.

the machine learning system is a neural network system, such as a deep learning system.

a neural architecture is used to generate the machine-readable language.

the neural architecture utilises recurrent neural networks or LSTMs or attention mechanisms or transformers.

the machine learning system has been trained on training data comprising natural language and a corresponding structured machine-readable representation, such as a machine-readable language comprising semantic nodes and passages.

a passage of natural language is passed through a sequence-to-sequence neural architecture trained on training data comprising natural language and a corresponding structured representation that encodes meaning.

the neural network system is a switch transformer feed forward neural network system.

the neural architecture comprises an encoder and decoder and beam searching is used during decoding of the semantic representations from the decoder to remove invalid semantic representations.

the word or sequence of words in a natural language is a question and the question is answered with reference to the semantic representation.

the word or sequence of words in a natural language is one or more documents and the semantic representation of the one or more documents is used to answer question.

reasoning with reference to the semantic representation produces further, new representations.

when automatically translating a sequence of words expressed in the natural language into the machine-readable language, the structure of the sequence of words is compared with known machine-readable language structures in the memory to identify similarities.

automatically translating the word or sequence of words into the machine-readable language is achieved by referencing a store of previously identified correct translations between the natural language and the machine-readable language.

automatically translating the word or sequence of words into the machine-readable language is achieved by utilising a pipeline of functions which transform the word or sequence of words into a series of intermediate forms.

the semantic impact of changes to the word or sequence of words in a natural language wording of the translation in the natural language is automatically assessed to determine whether known or ground truth examples of semantic nodes or passages can be used that are sufficient accurate.

the semantic nodes or passages that represent the words or sequence of words provides a machine-readable representation of the meaning of the words or sequence of words.

the semantic nodes or passages that represent the words or sequence of words are processed by a computer-based system for one or more of the following: to derive facts or relationships, to reason, to learn, to translate, to answer questions, to process natural language content, to enable man-machine interaction, to represent and to police rules or tenets, to enable one or more vertical applications.

the semantic nodes or passages that represent the words or sequence of words are processed by a computer-based system to generate an output that is human-readable.

the human readable output include one or more of the following: an answer to a question expressed in the natural language; a reasoning statement that explains how the system has reached a conclusion; a learning statement that explains what the system has learnt; a response in a man/machine interaction.

The system is further operable to automatically translate from the structured-machine readable representation to the natural language.

When translating from the structured-machine readable representation to the natural language the system varies the generated translations between alternatives that are substantially semantically equivalent to create varied and fresh responses for the benefit of human users.

Automatically translating the word or sequence of words into the machine-readable language is achieved by referencing a context of information relevant to generating a correct translation.

Semantic Node Resolution a service is provided that is operable to receive a description of an entity and return one or more identifiers for structured, machine-readable representations of data corresponding to the entity, so that a user is able to use a shared identifier for the entity.

the description is partially or fully described in the machine-readable language.

the description is partially or fully written in one or more natural languages.

the service compares the description of the proposed semantic node or passages with available information about existing entities to determine if there is a match.

the service probabilistically determines if there is a match.

the service additionally returns probabilities of matches along with the one or more identifiers.

the service returns a new identifier if no match is found.

Tenets the structured representation of data includes one or more tenets, statements or other rules defining the objectives or motives, also represented using the structured representation of data; and a potential action is analysed to determine whether executing the action would optimize or otherwise affect achievement or realization of those tenets, statements or other rules; and actions are selected, deciding on or executed only if they optimize or otherwise positively affect the achievement or realization of those tenets, statements or other rules.

actions that conform to the tenets, statements or other rules ('tenets') are automatically proposed by referencing the tenets.

the actions include communicating with users in written form.

actions include communicating with users in spoken form.

the tenets include at least one measure the system should try to maximise, such as user happiness.

the tenets include at least one measure the system should try to minimise, such as user unhappiness.

the tenets include at least one rule for actions the system must never do.

the system is further operable to avoid doing the actions the system must never do by referencing the tenets.

the tenets include at least one suggestion of what action to do in a defined circumstance.

the tenets include sub-tenets which are tenets that relate to other tenets or which are more specific examples of another tenet.

the actions include accessing other remote computer systems.

the actions include changing the state of devices linked to the system via a network.

the actions include initiating a spoken interaction with a human being.

a data store contains a machine-readable representation of the world that encodes meaning and where the system is further operable to reason with reference to the machine-readable representation of the world to select actions that conform with the tenets.

the machine-readable representation of the world comprises a representation of valid reasoning steps and where the system is further operable to utilise the representation of valid reasoning steps to reason.

the machine-readable representation of the world includes a representation of computational capabilities that are available to the system and where the system is further operable to utilise the computational capabilities by referencing the machine-readable representation.

the system is operable to learn and augment the machine-readable representation of the world.

the system is operable to learn from communication with at least one user.

the system is operable to learn from at least one external sensor connected to the system via a network.

the machine-readable tenets are at least partially represented by combinations of identifiers and where at least some of the identifiers represent concepts corresponding to real-world things the system is further operable to receive a description of a concept from a remote system and use the description to return an identifier which is likely to mean the concept.

the system is operable to continuously reason in a way that results in actions that conform with the tenets.

the system is operable to answer questions about the tenets from human users.

the computer system comprises a long-term memory; a short-term memory; a tenet-store containing machine-readable tenets representing rules to guide the system and where the computer system is operable to receive events and utilise the events, the contents of the long-term memory, the contents of the short-term memory and the tenets to do actions that conform with the tenets.

the computer system comprises a component which generates candidate actions; a component that decides whether to execute the candidate actions with reference to the tenets and a component which executes actions.

answering a question asked by a human user comprises two actions—generating a response to the question and communicating that response to the human user.

the events include communication from at least one user and where the actions include communication to at least one user.

the system is further operable to learn, and store what is has learned to the long-term memory.

the computer system is not operable to change the tenets.

the tenets include a tenet prohibiting actions which might result in changes to the tenets.

the system is further operable to do an independent check of each potential action against the tenets and will discard the potential action if the independent check finds that it is incompatible with the tenets.

the computer system is further operable to actively exclude knowledge on itself from being used in determining actions.

potential actions are autonomously generated by the computer based system.

potential actions are autonomously generated by the computer based system as outputs from processing inputs, such as audio or text.

potential actions are autonomously generated with a process that operates substantially continuously.

potential actions are autonomously generated without any external trigger event to initiate processing or user instruction or action to initiate processing.

the potential actions are automatically executed if they optimize or otherwise positively affect the achievement or realization of those tenets, statements or other rules.

The invention claimed is:

1. A computer implemented method for the automated analysis or use of data, comprising the steps of:
   (a) storing in a non-transitory computer-readable medium a structured, machine-readable representation of data that conforms to a machine-readable language; in which the structured, machine-readable representation of data includes one or more non-changeable tenets that prohibit any action that could result in changes to the one or more non-changeable tenets;
   (b) a computer system analysing a potential action to determine whether executing the potential action would result in changes to the one or more non-changeable tenets, and determining that executing the potential action would result in a change to a non-changeable tenet;
   (c) the computer system prohibiting the potential action which would result in a change to a non-changeable tenet; and
   (d) the computer system generating a reasoned, natural language explanation of why the potential action has been prohibited on the grounds that the potential action would change a non-changeable tenet.

2. The method of claim 1, in which the structured, machine-readable representation of data includes include ethics rules.

3. The method of claim 1, in which the structured, machine-readable representation of data includes rules defining affirmative or allowed actions or content.

4. The method of claim 1, in which the structured, machine-readable representation of data includes rules defining goals, such as optimisable actions or states.

5. The method of claim 1, in which the structured, machine-readable representation of data includes rules including web site or chatbot rules, such as abusive content rules.

6. The method of claim 1, in which the computer system generates a reasoned, natural language explanation that a potential action does comply or does not comply with the at least one non-changeable tenet.

7. The method of claim 1 in which the structured, machine-readable representation of data that conforms to the machine-readable language comprises semantic nodes and passages; and in which a semantic node represents an entity and is itself represented by an identifier; and a passage is either (i) a semantic node or (ii) a combination of semantic nodes; and where machine-readable meaning comes from the choice of semantic nodes and the way they are combined and ordered as passages.

8. The method of claim 1, in which the computer system does not change the tenets.

9. The method of claim 8 in which the computer system not changing the tenets comprises the tenets including a tenet prohibiting actions which might result in changes to the tenets.

10. The method of claim 1, in which the computer system independently checks each potential action against the tenets and discards the potential action if the independent check finds that the potential action is incompatible with the tenets.

11. The method of claim 1 in which the potential action includes changing the state of a device linked to the computer system via a network.

12. The method of claim 1 in which the potential action includes initiating a spoken interaction with a human being.

13. The method of claim 1 in which the computer system learns from one or more of: (i) communication with at least one user and (ii) one external sensor connected to the computer system via a network.

14. The method of claim 1 in which the tenets are at least partially represented by combinations of identifiers and where at least some of the identifiers represent concepts corresponding to real-world things.

15. The method of claim 1 in which the non-transitory computer-readable medium comprises a long-term non-transitory computer-readable medium; and in which the computer system comprises a short-term memory; the long-term non-transitory computer-readable medium including a tenet-store containing machine-readable tenets representing rules to guide the computer system and in which the computer system receives events and utilises the events, the contents of the long-term non-transitory computer-readable medium, the contents of the short-term memory and the tenets to do actions that conform with the tenets.

16. The method of claim 15 in which the events include communication from at least one user and where the actions include communication to at least one user.

17. The method of claim 15 in which the computer system learns, and stores what it has learned to the long-term non-transitory computer-readable medium.

18. The method of claim 1 in which the computer system comprises a component which generates candidate actions; a component that decides whether to execute the candidate actions with reference to the tenets and a component which executes actions.

19. The method of claim 1 in which the computer system actively excludes knowledge on itself from being used in determining actions.

20. The method of claim 1 in which potential actions are autonomously generated by the computer system.

21. The method of claim 1 in which potential actions are autonomously generated by the computer system according to one or more of the following: as outputs from processing inputs, such as audio or text; as a process that operates substantially continuously; as outputs without any external trigger event to initiate processing or user instruction or action to initiate processing.

22. The method of claim 20 in which the potential actions are automatically executed if they optimize or otherwise positively affect the achievement or realization of the tenets.

23. The method of claim 1 in which reasoning with reference to the machine-readable representation produces further, new machine-readable representations.

24. The method of claim 1 in which generating responses to queries comprises three operations, namely matching with machine-readable representations, such as passages, in a store, fetching and execution of computation units and fetching reasoning passages.

25. The method of claim 1 in which a question is represented in a memory as a machine representation, and the representation of the question, the machine representations previously stored in the non-transitory memory computer-readable medium, computation units and reasoning passages are all represented in substantially the same machine readable language.

26. The method of claim 1 in which reasoning is where machine-readable language is generated from other machine-readable language using reasoning steps that are represented as machine representations, such as passages, which represent the semantics of the reasoning steps.

27. The method of claim 1, in which new information is represented in the structured machine-readable representation, such as semantic nodes or passages, and is stored and used to improve reasoning steps.

28. The method of claim 1, in which learning takes place from reasoning, in which machine representations that are generated from a chain of reasoning steps, are combined with reasoning passages, and are stored and utilised.

29. The method of claim 1, including using different sets of tenets for different types of chatbots.

30. The method of claim 1, including using different sets of tenets for different end-users.

\* \* \* \* \*